US010046995B2

(12) United States Patent
Kumar et al.

(10) Patent No.: US 10,046,995 B2
(45) Date of Patent: Aug. 14, 2018

(54) WASTEWATER TREATMENT PLANT ONLINE MONITORING AND CONTROL

(75) Inventors: Aditya Kumar, Niskayuna, NY (US); Anthony John Murray, Niskayuna, NY (US); Ruijie Shi, Niskayuna, NY (US); Zhaoyang Wan, Trevose, PA (US); Mustafa Tekin Dokucu, Niskayuna, NY (US); Vijaysai Prasad, Kamataka (IN)

(73) Assignee: General Electric Company, Schenectady, NY (US)

( * ) Notice: Subject to any disclaimer, the term of this patent is extended or adjusted under 35 U.S.C. 154(b) by 548 days.

(21) Appl. No.: 14/234,955

(22) PCT Filed: Jul. 25, 2012

(86) PCT No.: PCT/US2012/048163
§ 371 (c)(1),
(2), (4) Date: Apr. 22, 2014

(87) PCT Pub. No.: WO2013/016438
PCT Pub. Date: Jan. 31, 2013

(65) Prior Publication Data
US 2015/0034553 A1    Feb. 5, 2015

Related U.S. Application Data

(60) Provisional application No. 61/574,017, filed on Jul. 26, 2011.

(51) Int. Cl.
*C02F 3/00*   (2006.01)
*C02F 3/12*   (2006.01)
(Continued)

(52) U.S. Cl.
CPC ............. *C02F 3/006* (2013.01); *C02F 1/66* (2013.01); *C02F 3/1268* (2013.01); *C02F 3/28* (2013.01);
(Continued)

(58) Field of Classification Search
None
See application file for complete search history.

(56) References Cited

U.S. PATENT DOCUMENTS 4,940,551 A   7/1990  Riggs et al.
5,811,255 A   9/1998  Hunter et al.
(Continued)

FOREIGN PATENT DOCUMENTS

CN   101794117 A   8/2010
EP     2110660 A1  10/2009

OTHER PUBLICATIONS

Alexiou (A Study of Pre-Acidification Reactor Design for Anaerobic Treatment of High Strength Industrial Wastewaters, Thesis, Apr. 1998, 253 pages).*
(Continued)

*Primary Examiner* — Hayden Brewster
(74) *Attorney, Agent, or Firm* — Wegman, Hessler & Vanderburg

(57) ABSTRACT

A method of operating a waste water treatment plant (WWTP) having at least one of an aerobic digester (AD) and a membrane bioreactor (MBR) is described. The method of operating AD is comprised of monitoring and controlling AD in real-time using an online extended Kalman filter (EKF) having a online dynamic model of AD. The EKF uses real-time AD measured data, and online dynamic model of AD to update adapted model parameters and estimate model based inferred variables for AD, which are used for AD control by AD control system having supervisory and low-
(Continued)

level control layers. The method of operating MBR is similar to that of AD. The supervisory control ensures the WWTP satisfying the effluent quality requirement while minimize the operation cost. A WWTP having at least one of AD or MBR is disclosed. The method of operating a WWTP can be implemented using a computer.

45 Claims, 49 Drawing Sheets

(51) Int. Cl.
    *C02F 3/28*     (2006.01)
    *C02F 3/30*     (2006.01)
    *C02F 1/66*     (2006.01)
    *G01N 33/18*     (2006.01)
    *G01N 21/00*     (2006.01)
    *G01N 33/00*     (2006.01)
    *G01N 31/00*     (2006.01)

(52) U.S. Cl.
    CPC ............. *C02F 3/2853* (2013.01); *C02F 3/30* (2013.01); *G01N 33/1826* (2013.01); *G01N 33/1866* (2013.01); *C02F 3/286* (2013.01); *C02F 2209/001* (2013.01); *C02F 2209/006* (2013.01); *C02F 2209/02* (2013.01); *C02F 2209/04* (2013.01); *C02F 2209/06* (2013.01); *C02F 2209/07* (2013.01); *C02F 2209/08* (2013.01); *C02F 2209/10* (2013.01); *C02F 2209/14* (2013.01); *C02F 2209/15* (2013.01); *C02F 2209/20* (2013.01); *C02F 2209/22* (2013.01); *C02F 2209/36* (2013.01); *C02F 2209/38* (2013.01); *C02F 2209/40* (2013.01); *C02F 2209/42* (2013.01); *C02F 2305/06* (2013.01); *Y02A 20/206* (2018.01); *Y02E 50/343* (2013.01); *Y02W 10/15* (2015.05)

(56) References Cited

U.S. PATENT DOCUMENTS

| | | | |
|---|---|---|---|
| 5,888,401 A | 3/1999 | Nguyen | |
| 6,616,843 B1 | 9/2003 | Behmann et al. | |
| 7,314,563 B2 | 1/2008 | Cho et al. | |
| 7,387,723 B2 | 6/2008 | Jordan | |
| 7,455,765 B2 | 11/2008 | Elefritz et al. | |
| 7,481,940 B2 | 1/2009 | Clifford, III et al. | |
| 7,611,632 B1 | 11/2009 | Wang et al. | |
| 7,655,142 B2 | 2/2010 | Liu et al. | |
| 7,718,066 B2 | 5/2010 | Jenkins et al. | |
| 7,862,722 B2 | 1/2011 | Moon | |
| 2008/0308493 A1 | 12/2008 | Amir et al. | |
| 2008/0314841 A1* | 12/2008 | Moon | C02F 3/006 210/746 |
| 2010/0028202 A1* | 2/2010 | Wan | G05B 23/0224 422/62 |
| 2012/0245747 A1* | 9/2012 | Kumar | G05B 13/048 700/288 |

OTHER PUBLICATIONS

Zaher (Modelling and Monitoring the Digestion Process in View of Optimisation and Smooth Operation of WWTP's, Thesis, Jun. 2005, 388 pages).*
Notice of Examination issued in connection with corresponding TW Application No. 101127122 dated Feb. 17, 2016.
Bernard, et al., "State Estimation for Wastewater Treatmente Process", Wastewater Quality Monitoring and Wastewater Quality Monitoring and Treatment, 2006, pp. 248-263.
Gerardi M.H., "The Microbiology of Anaerobic Digesters", Wastewater Microbiology Series, 2003, 170 pages.
International Search Report, dated May 22, 2013, issued in connection with corresponding WO Application PCT/US12/048163.
Jones, R.M. et. al.: "Towards Useful dynamic model of the anaerobic wastewater treatment process: A practical illustration of process identification", Water science and Technology, vol. 25, No. 7, 1992, pp. 61-71, XP002687569, IWA Publishing ISSN: 0273-1223 abstract.
Urrego-Patarroyo D et. al.: "Recurrent Neural Networks Biomass Observer for Anaerobic Processes", Intelligent Control, 2008. ISIC 2008. IEEE International Symposium on, IEEE Piscataway, NJ, USA, Sep. 3, 2008, pp. 183-188, XP031329457, ISBN: 978-1-4244-2224-1 p. 183.
Venkatesh et. al.: "Reduced order model monitoring and control of a membrane bioreactor system via delayed measurements", Water Science and Technology, vol. 64, No. 8, 2011, pp. 1675-1684, XP002696232, Uselmsford, NY. ISBN: 0273-1223, abstract pp. 1677—right hand col. figure 2.
African Journal of Biotechnology, Current Research and Development of Controlling Membrane Fouling of MBR, Da-Wen Gao, Yuan Fu, Yu Tao, Wei-Min Wu, Rui An and Xin-Xin Li Jul. 6, 2009 vol. 8, Issue 13, pp. 2993-2998.
Water Science Technology, Knowledge-Based System for Automatic MBR Control, Comas J, Meabe E, Sancho L, Ferrero G, Sipma J, Monclús H, Rodriguez-Roda I. 2010 vol. 62, Issue 12, pp. 2829-36 Abstract Only.
Jones, R.M. et. al.:Environmental Monitoring and Assessment 12: 271-282, Apr. 1989, Kluwer Academic Publishers.
McCarty, "Anaerobic Waste Treatment Fundamentals", Public Works, vol. No. 95, 19 pages, Sep. 1964.
Lech et al, "Automatic Control of the Activated Sludge Process—II. Efficacy of Control Strategies", Water Research, vol. No. 12, Issue No. 2, pp. 91-99, 1978.
Mosey, "Mathematical Modelling of the Anaerobic Digestion Process: Regulatory Mechanisms for the Formation of Short-Chain Volatile Acids from Glucose", Water Science and Technology, vol. No. 15, Issue No. 8, pp. 209-232, Jan. 1983.
Archer et al., "Hydrogen as a Process Control Index in a Pilot Scale Anaerobic Digester", Biotechnology Letters, vol. No. 8, Issue No. 3, pp. 197-202, 1986.
McCarty et al., "Anaerobic Wastewater Treatment", Environmental Science and Technology, vol. No. 20, Issue No. 12, pp. 1200-1206, 1986.
Jones et al., "State Estimation in Wastewater Engineering: Application to an Anaerobic Process",Environmental Monitoring and Assessment, vol. No. 12, pp. 271-282, 1989.
Dochain et al., "Adaptive Control of the Hydrogen Concentration in Anaerobic Digestion", Industrial and Engineering Chemistry Research, vol. No. 30, Issue No. 1, pp. 129-136, Jan. 1991.
Zwietering et al., "Modeling of Bacterial Growth as a Function of Temperature", Applied and Environmental Microbiology, vol. No. 57, Issue No. 4, pp. 1094-1101, Apr. 1991.
Serra et al., "Development of a Real-Time Expert System for Wastewater Treatment Plants Control", Control Engineering Practice, vol. No. 1, Issue No. 2, pp. 329-335, Apr. 1993.
Castensen et al., "Identification of Wastewater Treatment Processes for Nutrient Removal on a Full-Scale WWTP by Statistical Methods", Water Research, vol. No. 28, Issue No. 10, pp. 2055-2066, Oct. 1994.
Vanrolleghem, "Sensors for Anaerobic Digestion: An Overview", Proceedings Workshop Monitoring and Control of Anaerobic Digesters, pp. 1-7, Dec. 6-7, 1995.
Dochain et al., "Dynamical Modelling, Analysis, Monitoring and Control Design for Nonlinear Bioprocesses", Advances in Biochemical Engineering or Biotechnology, vol. No. 56, pp. 147-197, 1997.
Habtom et al., "Virtual Sensors Based on Recurrent Neural Networks and the Extended Kalman filter", Proceedings of the 1998 IEEE. International Conference on Control Applications, vol. No. 1, pp. 163-167, Sep. 1-4, 1998.
Singh et al., "Nutrient Requirement for UASB process: a Review", Biochemical Engineering, vol. No. 3, Issue No. 1, pp. 35-54, 1999.

(56) References Cited

OTHER PUBLICATIONS

Huang et al., "Hydrogen as a Quick Indicator of Organic Shock Loading in UASB", Water Science and Technology, vol. No. 42, Issue No. 3-4, pp. 43-50, 2000.

Bernard et al., "Dynamical Model Development and Parameter Identification for Anaerobic Wastewater Treatment Process", Biotechnology and Bioengineering, vol. No. 75, Issue No. 4, pp. 424-438, Nov. 20, 2001.

Alcaraz-Gonzalez et al., "Software Sensors for Highly Uncertain WWTPs: a New Approach Based on Interval Observers", Water Research, vol. No. 36, Issue No. 10, pp. 2515-2524, May 2002.

Batstone et al., "IWA Task Group for Mathematical Modelling of Anaerobic Digestion Processes", Water Science and Technology, vol. No. 45, Issue No. 10, pp. 65-73, 2002.

Peter et al., "Models in Advanced Wastewater Treatment Plant Control", Automatic Symposium Agronomy and Montpellier,pp. 1-26, Jan. 2003.

Liu et al., "Monitoring and Control of an Anaerobic Upflow Fixed-Bed Reactor for High-Loading-Rate Operation and Rejection of Disturbances", Biotechnology and Bioengineering, vol. No. 87, Issue No. 1, pp. 43-53, Jul. 5, 2004.

Liu et al., "Control of an Anaerobic Reactor towards Maximum Biogas Production", Water Science and Technology, vol. No. 50, Issue No. 11, pp. 189-198, 2004.

Bernard et al., "An Integrated System to Remote Monitor and Control Anaerobic Wastewater Treatment Plants through the Internet", Water Science and Technology, vol. No. 52, Issue No. 1-2, pp. 457-464, 2005.

Yong et al., "Feedforward-Feedback Control of Dissolved Oxygen Concentration in a Predenitrification System", Bioprocess and Biosystems Engineering, vol. No. 27, Issue No. 4, pp. 223-228, 2005.

Zheng et al., "Monitoring Granule Formation in Anaerobic Upflow Bioreactors Using Oligonucleotide Hybridization Probes", Biotechnology and Bioengineering, vol. No. 94, Issue No. 3, pp. 458-472, Jun. 20, 2006.

Kawail et al., "An Aeration Control for Advanced Wastewater Treatment Processes (SICE-ICCAS 2006)", SICE-ICASE International Joint Conference, Busan, pp. 4078-4082, Oct. 18-21, 2006.

Morel et al., "Design of a Multi-Model Observer-Based Estimator for Anaerobic Reactor Monitoring", Computers & Chemical Engineering, vol. No. 31, Issue No. 2, pp. 78-85, Dec. 1, 2006.

Martinez-Sibaja et al., "Cascade Fuzzy Logic Controller for an Anaerobic Digester", Electronics, Robotics and Automotive Mechanics Conference (CERMA 2007), Morelos, pp. 395-399, Sep. 25-28, 2007.

Benazzi et al., "On-Line Estimation and Detection of Abnormal Substrate Concentrations in WWTPS using a Software Sensor: a Benchmark Study", Environmental Technology, vol. No. 28, Issue No. 8, pp. 8 71-882, 2007.

Castellano et al., "Selection of Variables Using Factorial Discriminant Analysis for the State Identification of an Anaerobic UASB—UAF Hybrid Pilot Plant, Fed With Winery Effluents", Water Science and Technology, vol. No. 56, Issue No. 2, pp. 139-145, 2007.

Lardon et al., "Advances in Diagnosis of Biological Anaerobic Wastewater Treatment Plants", Control and Information Sciences, vol. No. 361, pp. 201-239, 2007.

Jiayu et al.,"Cascade Control of the pH in an Anaerobic Wastewater Treatment System", Bioinformatics and Biomedical Engineering, 3rd International Conference, Beijing, pp. 1-4, Jun. 11-13, 2009.

Kang et al., "Modeling and Control of pH in Pulp and Paper Wastewater Treatment Process", Journal of Water Resource and Protection, vol. No. 1, Issue No. 2, pp. 122-127, Aug. 2009.

Haimi et al., "Process Automation in Wastewater Treatment Plants: the Finnish Experience", E-Water, pp. 1-17, 2010.

Cristea et al., "Aeration Control of a Wastewater Treatment Plant using Hybrid NMPC", Computers and Chemical Engineering, vol. No. 35, Issue No. 4, pp. 638-650, Apr. 7, 2011.

\* cited by examiner

WASTEWATER TREATMENT PLANT ONLINE MONITORING AND CONTROL

CROSS-REFERENCE TO RELATED APPLICATIONS

This application claims the priority under 35 U.S.C. 119 to U.S. Provisional Patent Application Ser. No. 61/574,017 filed Jul. 26, 2011, and entitled "Wastewater Treatment Plant Online Monitoring and Control", which is herein incorporated by reference in its entirety.

GOVERNMENT RIGHTS

This application was funded under Department of Energy Contract DE-FC26-08NT05870. The U.S. Government has certain rights under this application and any patent issuing therefrom.

FIELD OF THE INVENTION

This application relates to wastewater treatment plants, more particularly to the monitoring and control of the key units of a wastewater treatment plant.

BACKGROUND OF THE INVENTION

Soaring fuel prices, shrinking water resources, and increased regulation of wastewater treatment plant effluent are forcing wastewater treatment plant operators to manage their key units more efficiently.

Typically, key units or components of a wastewater treatment plant include a anaerobic digester (AD) and membrane bioreactor (MBR). The AD and MBR operate in a coordinated and an interdependent fashion, hence any upsets or variations in any key unit affect functionality and performance of the rest of the key units. The wastewater feed to the AD, for example, may have significant variations in flow rates, influent chemical oxygen demand (COD), total suspended solids, total soluble COD, temperature, nitrogen, phosphates, sulfates, and pH. The variations in the AD, in turn, impact operations of downstream process units, such as the MBR.

Conventionally, the variations in the key units are monitored periodic manual sampling and off-line laboratory tests to monitor the system performance, identify any abnormal condition due to variations in the wastewater feed, and decide on appropriate remedial action. Unfortunately, these lab tests are time consuming and infrequent manual sampling are not sufficient to detect potentially adverse changes in a timely manner. Also, manual operation is often inadequate in taking timely corrective actions needed to mitigate effects of variations and avoid any upsets. In particular, upsets in the AD can lead to instabilities which, if undetected or not corrected in a timely manner, can eventually cause a washout condition with loss of active biomass requiring costly shutdown and re-seeding. Also, whenever AD performance is hindered, biogas generation is sacrificed and the load on downstream MBR can become overwhelmingly high leading to violations in MBR effluent water quality.

These factors often lead to over-design and very conservative operation of the AD and MBR to avoid any potential upsets that can destabilize the AD and MBR. However, a conservative operation often means inefficient operation involving overdosing chemical additives and over-aerating to allow for unknown process variations, and thus unnecessary high operating costs.

Thus, a need exists for an improved method of operating a wastewater treatment plant through monitoring and controlling the AD and MBR of a wastewater treatment plant.

SUMMARY OF THE INVENTION

In one aspect of the invention, a method of operating an anaerobic digester (AD) was surprisingly discovered, comprising: providing and monitoring an AD, wherein the monitoring comprises:
providing an AD offline extended Kalman filter (EKF) having an offline dynamic model of the AD, providing an AD online EKF having an online dynamic model of the AD; wherein the offline and the online dynamic models of the AD are comprised of states, process material balances, energy balances, bio-chemical reaction kinetics, estimated parameters, and adapted model parameters; wherein the adapted model parameters are a subset of the estimated parameters;
providing historical operation data for the AD, wherein the historical operation data is comprised of historical measured input data, historical measured output data, and historical laboratory analysis data;
identifying the estimated parameters of the offline dynamic model of the AD using the AD offline EKF and the historical operation data for the AD;
importing the estimated parameters from the offline dynamic model of the AD into the online dynamic model of the AD;
providing real time operation data for the AD to the AD online EKF, wherein the real time operational data is comprised of real time measured input data and real time measured output data of the AD;
updating the adapted model parameters of the online dynamic model of the AD and estimating the model based inferred variables of the AD using the AD online EKF, the online dynamic model of the AD, the real time measured input data of the AD, and the real time measured output data of the AD; and
providing one or more of the adapted model parameters of the online dynamic model of the AD and the model based inferred variables of the AD to an operator of the AD.

In another aspect of the method of operating the AD, the AD is comprised of an AD reactor.

In another aspect of the method of operating the AD, the AD reactor is a continuously stirred tank reactor (CSTR), upflow anaerobic sludge blanket reactor (UASB), expanded granular sludge bed reactor (EGSB), mixed bed, moving bed, low-rate, or high-rate reactor.

In another aspect of the method of operating the AD, the AD is further comprised of a pre-acidification (PA) reactor, wherein the AD reactor and the pre-acidification reactor are modeled separately in both of the online and offline dynamic models of the AD.

In another aspect of the method of operating the AD, the AD is comprised of a mixing stage and at least one recycle line.

In another aspect of the method of operating the AD, the at least one recycle line of the AD is a pre-acidification reactor recycle line or an AD reactor recycle line.

In another aspect of the method of operating the AD, materials for the material balances in the online and offline dynamic models of the AD are comprised of insoluble organics, soluble substrates, volatile fatty acids (VFA), biomass, inorganic carbon and alkalinity.

In another aspect of the method of operating the AD, insoluble organics is comprised of carbohydrates, protein and fat; the soluble substrate and VFA include at least one of sugars, LCFA, amino acids, acetate acid, or propionate acid; and the biomass includes biomass for acedogenesis, acetogenesis, acetoclastic methanogenesis and hydrogen methanogenesis bio-chemical processes.

In another aspect of the method of operating the AD, the inorganic carbon is comprised of at least one of carbon dioxide, carbonate, or bicarbonate.

In another aspect of the method of operating the AD, the alkalinity is comprised of alkalinity associated with bicarbonate, VFA, added alkali, and generation of ammonia and hydrogen sulfide.

In another aspect of the method of operating the AD, the bio-chemical reaction kinetics in the online and offline dynamic models of the AD are comprised of at least one of insoluble organics hydrolysis, acedogenesis, acetogenesis, acetoclastic methanogenesis, or hydrogen methanogenesis process.

In another aspect of the method of operating the AD, the historical operation data of the AD and the real time operation data of the AD are comprised of at least one of raw influent pH, raw influent temperature, raw influent flow rate, raw influent total organic carbon (TOC), raw influent total inorganic carbon (TIC), added alkali flow rate, PA reactor fluid level, AD feed flow rate, raw influent soluble chemical oxygen demand (SCOD), raw influent total chemical oxygen demand (TCOD), raw influent soluble bio-chemical oxygen demand (SBOD), raw influent volatile suspended solids (VSS), raw influent total suspended solids, raw influent soluble inorganic nitrogen, raw influent VFA, added alkali concentration, PA reactor pH, PA effluent TOC, PA effluent TIC, AD biogas flow rate, AD biogas methane ($CH_4$) concentration, AD Biogas carbon dioxide ($CO_2$) concentration, AD reactor pH, AD effluent TOC, AD effluent TIC, AD effluent VFA, AD effluent alkalinity, AD reactor mixed liquor volatile suspended solids (MLVSS), AD effluent TCOD, AD effluent SCOD, AD effluent VSS, or AD effluent TSS.

In another aspect of the method of operating the AD, the estimated parameters and the adapted model parameters of the offline dynamic model of the AD and the online dynamic model of the AD are comprised of at least one of PA reactor composite fraction of carbohydrate, PA reactor composite fraction of fat, PA reactor composite fraction of protein, PA reactor fraction of insoluble convertible to SBOD, PA reactor acedogenthese reaction coefficient, PA reactor biomass decay rate, PA reactor insoluble hydrolysis reaction coefficient, PA reactor insoluble flow out coefficient, PA reactor $CO_2$ escape coefficient, AD reactor composite fraction of carbohydrate, AD reactor composite fraction of fat, AD reactor composite fraction of protein, AD reactor fraction of insoluble convertible to SBOD, AD reactor acedogenthese reaction coefficient, AD reactor acetogenesis reaction coefficient, AD reactor acetoclastic methanogenesis reaction coefficient, AD reactor hydrogen methanogenesis reaction coefficient, AD reactor biomass decay rate, PA reactor insoluble hydrolysis reaction coefficient, or PA reactor insoluble flow out coefficient.

In another aspect of the method of operating the AD, at least one of the estimated parameters of the offline dynamic model of the AD and the model based inferred variables of the online dynamic model of the AD are estimated with confidence intervals.

In another aspect of the method of operating the AD, the model based inferred variables of the online dynamic model of the AD are comprised of at least one of the following unmeasured inputs or outputs of the AD: raw influent insoluble COD, raw influent insoluble inert COD, raw influent soluble inert COD, raw influent SBOD saccharide, raw influent SBOD long chain fatty acids (LCFA), raw influent SBOD amino acid, raw influent propionate acid, raw influent acetate acid, raw influent inorganic carbon content, raw influent alkalinity, raw influent inorganic nitrogen, raw influent SCOD, raw influent TCOD, raw influent SBOD, PA reactor alkalinity, PA reactor VFA, PA reactor temperature, PA reactor SCOD, PA reactor TCOD, PA reactor SBOD, AD reactor alkalinity, AD reactor VFA, AD reactor temperature, AD reactor SCOD, AD reactor SBOD, AD reactor acedogenthese biomass, AD reactor acetogenesis biomass, AD reactor acetoclastic methanogenesis biomass, AD reactor hydrogen methanogenesis biomass, AD reactor insoluble COD, AD reactor insoluble inert COD, AD reactor soluble inert COD, AD reactor SBOD saccharide, AD reactor SBOD LCFA, AD reactor SBOD amino acid, AD reactor propionate acid, AD reactor acetate acid, AD reactor inorganic carbon content, AD reactor alkalinity, AD reactor inorganic nitrogen, AD reactor SCOD, AD reactor TCOD, AD reactor SBOD, SCOD conversion rate, $CH_4$ conversion efficiency, or recycle flow rate.

In another aspect of the method of operating the AD, the adapted model parameters of the online dynamic model of the AD are turned using different weights for online measurements and prior knowledge of measurement accuracy.

In another aspect of the method of operating the AD, limits are applied to one or more of the estimated parameters and the adapted model parameters; wherein constraints are applied to one or more of the model based inferred variables.

In another aspect of the method of operating the AD, the adapted model parameters of the online dynamic model of the AD are adjusted by one or both of: calculating model predicted outputs of the AD using the AD online EKF, the online dynamic model of the AD, the real time measured input data of the AD, and the real time measured output data of the AD, comparing the measured output data of the AD and the model predicted outputs of the AD, and updating the adapted model parameters of the online dynamic model of the AD such that the real time measured output data of the AD substantially correspond with the model predicted outputs of the AD; or periodically re-identifying the estimated parameters of the offline dynamic model of the AD using the AD offline EKF and the historical operation data for the AD, and importing the estimated parameters from the offline dynamic model of the AD into the online dynamic model of the AD.

In another aspect of the method of operating the AD, the AD is controlled, wherein the controlling comprises: providing an AD control system; wherein the AD is comprised of an AD reactor and optionally a PA reactor; wherein the AD control system uses one or more of the real time measured input data of the AD, the real time measured output data of the AD, the estimated parameters of the online dynamic model of the AD, or the model based inferred variables of the AD to control at least one of a nutritional additive concentration of the AD reactor, a nutritional additive concentration of the PA reactor, pH of the AD reactor, pH of the PA reactor, biomass concentration of the AD reactor, fluid level of the PA reactor, or a recycle flow rate of the AD.

In another aspect of the method of operating the AD, at least one of the monitoring the AD or the controlling the AD is performed using a computer.

In another aspect of the method of operating the AD, controlling the nutritional additive concentration of the AD prevents biomass overfeeding and starvation, controlling the nutritional additive concentration of the PA reactor prevents biomass overfeeding and starvation, controlling the pH of the AD reactor minimizes alkali dosing, wherein controlling the pH of the PA reactor minimizes alkali dosing, controlling the biomass concentration of the AD reactor offsets biomass inhibition and saves alkali, controlling a recycle flow rate of the PA reactor minimizes alkali dosing and maintains fluid level of the PA reactor, and controlling a recycle flow rate of the AD reactor maximizes COD conversion and biogas generation.

In another aspect of the method of operating the AD, the AD control system is comprised of an AD supervisory control system and an AD low-level control system.

In another aspect of the method of operating the AD, the AD supervisory control system is comprised of at least one of an AD reactor pH supervisory controller, a PA reactor pH supervisory controller, or an PA:AD overall recycle flow ratio supervisory controller.

In another aspect of the method of operating the AD, the AD reactor pH supervisory controller is comprised of an AD reactor nonlinear Proportion-Integration (PI) pH controller and an AD reactor Proportion (P) alkalinity controller in a cascaded configuration.

In another aspect of the method of operating the AD, the PA reactor pH supervisory controller is comprised of a PA reactor nonlinear PI pH controller and a PA reactor P alkalinity controller in a cascaded configuration.

In another aspect of the method of operating the AD, the PA:AD overall recycle flow ratio supervisory controller is comprised of a PA:AD recycle ratio controller, and a PA reactor and AD reactor recycle flow rate controller.

In another aspect of the method of operating the AD, the AD low-level control system is comprised of at least one of an AD reactor biomass controller, a PA reactor fluid level controller, a PA reactor nutritional additive concentration controller, or an AD reactor nutritional additive concentration controller.

In another aspect of the method of operating the AD, at least one of the AD reactor pH supervisory controller or the PA reactor pH supervisory controller uses a model based inferred variable of the AD.

In another aspect of the method of operating the AD, the model based inferred variable of the AD is PA alkalinity or AD alkalinity.

In another aspect of the method of operating the AD, at least one of the AD reactor pH supervisory controller or the PA reactor pH supervisory controller has a feedforward control action; wherein the feedforward control action uses a model based inferred variable of the AD.

In another aspect of the method of operating the AD, the model based inferred variable of the AD is raw influent alkalinity.

In another aspect of the method of operating the AD, at least one of the AD reactor biomass controller, the PA reactor nutritional additive concentration controller, and the AD reactor nutritional additive concentration controller uses at least one of the estimated parameters of the online dynamic model of the AD or the model based inferred variables of the AD.

In another aspect of the method of operating the AD, the estimated parameters of the online dynamic model of the AD or the model based inferred variables of the AD is at least one of reaction coefficients and biomass concentrations for hydrolysis, acedogenthese, acetogenesis, acetoclastic methanogenesis, or hydrogen methanogenesis processes.

In another aspect of the method of operating the AD, the AD reactor pH supervisory controller is comprised of an AD reactor nonlinear PI pH controller and a PA reactor P alkalinity controller in a cascaded configuration.

In yet another aspect of the invention, a method of operating a membrane bioreactor (MBR) was surprisingly discovered, comprising: providing and monitoring a MBR, wherein the monitoring comprises:
  providing a MBR offline extended Kalman filter (EKF) having an offline dynamic model of the MBR, providing a MBR online EKF having an online dynamic model of the MBR; wherein the offline and the online dynamic models of the MBR are comprised of states, process material balances, energy balances, bio-chemical reaction kinetics, estimated parameters, and adapted model parameters; wherein the adapted model parameters are a subset of the estimated parameters;
  providing historical operation data for the MBR, wherein the historical operation data is comprised of historical measured input data, historical measured output data, and historical laboratory analysis data;
  identifying the estimated parameters of the offline dynamic model of the MBR using the MBR offline EKF and the historical operation data for the MBR;
  importing the estimated parameters from the offline dynamic model of the MBR into the online dynamic model of the MBR;
  providing real time operation data for the MBR to the MBR online EKF, wherein the real time operational data is comprised of real time measured input data and real time measured output data of the MBR;
  updating the adapted model parameters of the online dynamic model of the MBR and estimating the model based inferred variables of the MBR using the MBR online EKF, the online dynamic model of the MBR, the real time measured input data of the MBR, and the real time measured output data of the MBR; and
  providing one or more of the adapted model parameters of the online dynamic model of the MBR and the model based inferred variables of the MBR to an operator of the MBR.

In another aspect of the method of operating the MBR, the MBR is comprised of an aerobic tank, a membrane tank, and optionally an anoxic tank; wherein the aerobic tank is located upstream of the membrane tank; wherein the anoxic tank is located either immediately upstream or downstream of the aerobic tank when the anoxic tank is present.

In another aspect of the method of operating the MBR, the aerobic tank and the anoxic tank are modeled separately in both of the online and offline dynamic models of the MBR when both of the aerobic and the anoxic tanks are present.

In another aspect of the method of operating the MBR, the MBR is further comprised of a mixer and at least one recycle line.

In another aspect of the method of operating the MBR, the at least one recycle line of the MBR is an anoxic tank recycle line or an aerobic tank recycle line.

In another aspect of the method of operating the MBR, materials for the material balances in the online and offline dynamic models of the MBR are comprised of at least one of particulate inert, slowly degradable substrate, heterotrophic biomass, autotrophic biomass, decayed biomass, soluble inert, soluble readily degradable substrate, dissolved oxygen, dissolved nitrate-N (Nitrogen), dissolved ammonia-N, particulate bio-degradable-N, or bicarbonate alkalinity.

In another aspect of the method of operating the MBR, the bio-chemical reaction kinetics in the online and offline dynamic models of the MBR are comprised of at least one of aerobic heterotroph, anoxic heterotroph, aerobic autotroph, decay of heterotroph, decay of autotroph, ammonification of soluble organic N, hydrolysis of organics, or hydrolysis of organic N.

In another aspect of the method of operating the MBR, the historical operation data of the MBR and the real time operation data of the MBR are comprised of at least one of raw influent pH, raw influent temperature, raw influent flow rate, raw influent TOC, raw influent TIC, added alkali flow rate, added alkali concentration, effluent flow out rate, raw influent SCOD, raw influent TCOD, raw influent readily biodegradable COD, raw influent slowly biodegradable COD, raw influent VSS, raw influent TSS, raw influent nitrate nitrogen, raw influent ammonia-nitrogen, raw influent soluble biodegradable organic nitrogen, raw influent particulate degradable organic nitrogen, raw influent inorganic inert particulate, membrane permeate flow rate, wasting sludge flow rate, anoxic tank addition biodegradable COD flow, anoxic rank reactor pH, anoxic tank Dissolved Oxygen, anoxic tank temperature, anoxic tank liquid level, anoxic rank MLVSS, anoxic tank MLSS, aerobic rank blower air flow rate, aerobic tank reactor pH, aerobic tank alkalinity, aerobic tank MLVSS, aerobic tank MLSS, aerobic tank Dissolved Oxygen, aerobic tank temperature, aerobic tank liquid level, membrane tank MLSS, membrane tank MLVSS, membrane permeate SCOD, membrane permeate TCOD, membrane permeate TOC, membrane permeate TIC, membrane permeate nitrate nitrogen, membrane permeate ammonia-nitrogen, wasting sludge MLSS, or wasting sludge MLVSS.

In another aspect of the method of operating the MBR, the estimated parameters and the adapted model parameters of the offline dynamic model of the MBR and the online dynamic model of the MBR are comprised of at least one of heterotrophic maximum specific growth rate, anoxic/aerobic hetrotroph growth rate, anoxic/aerobic hydrolysis rate fraction, particulate hydrolysis max specific rate constant, autotrophic maximum specific growth rate, decay constant for heterotrophs, decay constant for autotrophs, yield of heterotrophic biomass, yield of autotrophic biomass, carbon content in soluble substrate, carbon content of particulate substrate, carbon content of soluble inert, carbon content of particulate nondegradable organic, mass transfer coefficient for O2 removal in aerobic tank, or mass transfer coefficient for $CO_2$ removal in anoxic tank.

In another aspect of the method of operating the MBR, at least one of the estimated parameters of the offline dynamic model of the MBR and the model based inferred variables of the online dynamic model of the MBR are estimated with confidence intervals.

In another aspect of the method of operating the MBR, the model based inferred variables of the online dynamic model of the MBR are comprised of at least one of the following unmeasured inputs or outputs of the MBR: raw influent alkalinity, raw influent nitrate nitrogen, raw influent ammonia-nitrogen, raw influent SCOD, raw influent TCOD, raw influent readily biodegradable COD, raw influent slowly biodegradable COD, raw influent VSS, raw influent TSS, raw influent inorganic inert particulate, anoxic rank SCOD, anoxic tank MLVSS, anoxic tank nitrate nitrogen, anoxic tank ammonia-nitrogen, anoxic tank biodegradable COD, aerobic tank SOCD, aerobic tank MLVSS, aerobic tank nitrate nitrogen, aerobic tank ammonia-nitrogen, aerobic tank biodegradable COD, membrane tank MLVSS, membrane permeate SCOD, membrane permeate biodegradable COD, membrane permeate TCOD, membrane permeate nitrate nitrogen, membrane permeate ammonia-nitrogen, wasting sludge MLVSS, COD removal rate, or nitrogen removal rate.

In another aspect of the method of operating the MBR, the adapted model parameters of the online dynamic model of the MBR are tuned using different weights for online measurements and prior knowledge of measurement accuracy.

In another aspect of the method of operating the MBR, limits are applied to one or more of the estimated parameters and the adapted model parameters; wherein constraints are applied to one or more of the model based inferred variables.

In another aspect of the method of operating the MBR, the adapted model parameters of the online dynamic model of the MBR are adjusted by one or both of: calculating model predicted outputs of the MBR using the MBR online EKF, the online dynamic model of the MBR, the real time measured input data of the MBR, and the real time measured output data of the MBR, comparing the measured output data of the MBR and the model predicted outputs of the MBR, and updating the adapted model parameters of the online dynamic model of the MBR such that the real time measured output data of the MBR substantially correspond with the model predicted outputs of the MBR; or periodically re-identifying the estimated parameters of the offline dynamic model of the MBR using the MBR offline EKF and the historical operation data for the MBR, and importing the estimated parameters from the offline dynamic model of the MBR into the online dynamic model of the MBR.

In another aspect of the method of operating the MBR, the MBR is controlled, wherein the controlling comprises: providing an MBR control system; wherein the MBR is comprised of an aerobic tank, a membrane tank, and optionally an anoxic tank; wherein the MBR control system uses one or more of the real time measured input data of the MBR, the real time measured output data of the MBR, the estimated parameters of the online dynamic model of the MBR, or the model based inferred variables of the MBR to control at least one of pH of the anoxic tank, pH of the aerobic tank, fluid level of the aerobic tank, DO concentration of the aerobic tank, MLSS concentration of the membrane tank, bCOD addition flow rate setpoint of the anoxic tank, at least one nutritional additive concentration of the anoxic tank, or at least one recycle flow setpoint of the MBR.

In another aspect of the method of operating the MBR, at least one of the monitoring the MBR or the controlling the MBR is performed using a computer.

In another aspect of the method of operating the MBR, wherein controlling at least one nutritional additive concentration of the anoxic tank prevents biomass overfeeding and starvation, wherein controlling the pH of the anoxic tank minimizes alkali dosing, wherein controlling the pH of the aerobic tank minimizes alkali dosing, wherein controlling the fluid level of the aerobic tank minimizes the affect of fluid perturbations of the aerobic tank, wherein controlling the DO concentration of the aerobic tank ensures that a proper concentration of DO is present in the aerobic tank, wherein controlling the MLSS concentration of the membrane tank maximizes membrane permeability, wherein controlling the bCOD addition flow rate setpoint of the anoxic tank minimizes bCOD usage, wherein controlling at least one recycle flow setpoint of the MBR helps to maintain flow through the MBR.

In another aspect of the method of operating the MBR, the MBR control system is comprised of an MBR supervisory control system and an MBR low-level control system.

In another aspect of the method of operating the MBR, the MBR supervisory control system is comprised of at least one of an aerobic tank DO supervisory controller, an anoxic tank recycle flow supervisory controller, or an anoxic tank bCOD addition flow rate supervisory control scheme.

In another aspect of the method of operating the MBR, the anoxic tank bCOD addition flow supervisory control scheme of the MBR is comprised of an anoxic tank bCOD setpoint supervisory controller, an anoxic tank bCOD addition flow rate supervisory feedback controller, and an anoxic tank bCOD addition flow rate supervisory feedforward controller.

In another aspect of the method of operating the MBR, the MBR low-level control system is comprised of at least one of an aerobic tank fluid level PI controller, an aerobic tank pH controller, an anoxic tank pH controller, an anoxic tank recycle line flow rate controller, an aerobic tank DO concentration controller, an anoxic tank nutritional additive concentration controller, aerobic tank recycle line flow rate PI controller, total MBR recycle flow rate PI controller, an aerobic tank recycle flow rate lookup table, or a membrane tank MLSS concentration controller.

In another aspect of the method of operating the MBR, the MLSS concentration controller uses a model based inferred variable of the MBR.

In another aspect of the method of operating the MBR, the model based inferred variable of the MBR is MLVSS concentration or MLSS concentration.

In another aspect of the method of operating the MBR, the aerobic tank DO supervisory controller, the anoxic tank recycle flow supervisory controller, and the anoxic tank bCOD addition flow rate supervisory control scheme satisfy membrane permeate requirements on COD, nitrate, and ammonia, while minimizing aeration, recycle flow, and bCOD addition.

In another aspect of the method of operating the MBR, at least one of the aerobic tank DO supervisory controller, the anoxic tank recycle flow supervisory controller, or the anoxic tank bCOD addition flow rate supervisory control scheme uses at least one of the estimated parameters of the online dynamic model of the MBR or the model based inferred variables of the MBR.

In yet another aspect of the invention, a method of operating a wastewater treatment plant (WWTP) was surprisingly discovered, comprising:

operating an anaerobic digester (AD) comprising: providing an AD and monitoring the AD, wherein the monitoring comprises:
providing an AD offline extended Kalman filter (EKF) having an offline dynamic model of the AD, providing an AD online EKF having an online dynamic model of the AD; wherein the offline and the online dynamic models of the AD are comprised of states, process material balances, energy balances, bio-chemical reaction kinetics, estimated parameters, and adapted model parameters; wherein the adapted model parameters are a subset of the estimated parameters;
providing historical operation data for the AD, wherein the historical operation data is comprised of historical measured input data, historical measured output data, and historical laboratory analysis data;
identifying the estimated parameters of the offline dynamic model of the AD using the AD offline EKF and the historical operation data for the AD; importing the estimated parameters from the offline dynamic model of the AD into the online dynamic model of the AD;
providing real time operation data for the AD to the AD online EKF, wherein the real time operational data is comprised of real time measured input data and real time measured output data of the AD;
updating the adapted model parameters of the online dynamic model of the AD and estimating the model based inferred variables of the AD using the AD online EKF, the online dynamic model of the AD, the real time measured input data of the AD, and the real time measured output data of the AD; and
providing one or more of the adapted model parameters of the online dynamic model of the AD and the model based inferred variables of the AD to an operator of the AD.

operating a membrane bioreactor (MBR), comprising:
providing a MBR and monitoring the MBR, wherein the monitoring comprises:
providing a MBR offline extended Kalman filter (EKF) having an offline dynamic model of the MBR, providing a MBR online EKF having an online dynamic model of the MBR; wherein the offline and the online dynamic models of the MBR are comprised of states, process material balances, energy balances, bio-chemical reaction kinetics, estimated parameters, and adapted model parameters; wherein the adapted model parameters are a subset of the estimated parameters;
providing historical operation data for the MBR, wherein the historical operation data is comprised of historical measured input data, historical measured output data, and historical laboratory analysis data;
identifying the estimated parameters of the offline dynamic model of the MBR using the MBR offline EKF and the historical operation data for the MBR;
importing the estimated parameters from the offline dynamic model of the MBR into the online dynamic model of the MBR;
providing real time operation data for the MBR to the MBR online EKF, wherein the real time operational data is comprised of real time measured input data and real time measured output data of the MBR;
updating the adapted model parameters of the online dynamic model of the MBR and estimating the model based inferred variables of the MBR using the MBR online EKF, the online dynamic model of the MBR, the real time measured input data of the MBR, and the real time measured output data of the MBR; and
providing one or more of the adapted model parameters of the online dynamic model of the MBR and the model based inferred variables of the MBR to an operator of the MBR.

In another aspect of the method of operating the WWTP, the adapted model parameters of the online dynamic model of the AD are adjusted by one or both of: calculating model predicted outputs of the AD using the AD online EKF, the online dynamic model of the AD, the real time measured input data of the AD, and the real time measured output data of the AD, comparing the measured output data of the AD and the model predicted outputs of the AD, and updating the adapted model parameters of the online dynamic model of the AD such that the real time measured output data of the AD substantially correspond with the model predicted outputs of the AD; or periodically re-identifying the estimated parameters of the offline dynamic model of the AD using the AD offline EKF and the historical operation data for the AD, and importing the estimated parameters from the offline dynamic model of the AD into the online dynamic model of the AD.

In another aspect of the method of operating the WWTP, the adapted model parameters of the online dynamic model of the MBR are adjusted by one or both of: calculating model predicted outputs of the MBR using the MBR online EKF, the online dynamic model of the MBR, the real time measured input data of the MBR, and the real time measured output data of the MBR, comparing the measured output data of the MBR and the model predicted outputs of the MBR, and updating the adapted model parameters of the online dynamic model of the MBR such that the real time measured output data of the MBR substantially correspond with the model predicted outputs of the MBR; or periodically re-identifying the estimated parameters of the offline dynamic model of the MBR using the MBR offline EKF and the historical operation data for the MBR, and importing the estimated parameters from the offline dynamic model of the MBR into the online dynamic model of the MBR.

In another aspect of the method of operating the WWTP, the AD is controlled, wherein controlling the AD comprises: providing an AD control system; wherein the AD control system uses one or more of the real time measured input data of the AD, the real time measured output data of the AD, the estimated parameters of the online dynamic model of the AD, or the model based inferred variables of the AD to control at least one of a nutritional additive concentration of the AD reactor, a nutritional additive concentration of the PA reactor, pH of the AD reactor, pH of the PA reactor, biomass concentration of the AD reactor, fluid level of the PA reactor, or a recycle flow rate of the AD.

In another aspect of the method of operating the WWTP, the MBR is controlled, wherein controlling the MBR comprises: providing an MBR control system; wherein the MBR control system uses one or more of the real time measured input data of the MBR, the real time measured output data of the MBR, the estimated parameters of the online dynamic model of the MBR, or the model based inferred variables of the MBR to control at least one of pH of the anoxic tank, pH of the aerobic tank, fluid level of the aerobic tank, DO concentration of the aerobic tank, MLSS concentration of the membrane tank, bCOD addition flow rate setpoint of the anoxic tank, at least one nutritional additive concentration of the anoxic tank, or at least one recycle flow setpoint of the MBR.

In another aspect of the method of operating the WWTP, the MBR is located upstream of the AD, wherein the MBR online EKF provides model based inferred variables to the AD, wherein the model based inferred variables provided to the AD comprise the composition and flow rate of the MBR effluent; wherein the model based inferred variables provided to the AD enable feed forward control of the AD.

In another aspect of the method of operating the WWTP, the AD is located upstream of the MBR, wherein the AD online EKF provides model based inferred variables to the MBR, wherein the model based inferred variables provided to the MBR comprise the composition and flow rate of the AD effluent; wherein the model based inferred variables provided to the MBR enable feed forward control of the MBR.

In another aspect of the method of operating the WWTP, operating the WWTP is performed using a computer.

In yet another aspect of the invention, a waste water treatment plant (WWTP) comprised of at least one of an aerobic digester (AD) and a membrane bioreactor (MBR) was discovered:

wherein the AD is comprised of an AD reactor, an AD control system, and optionally a pre-acidification (PA) reactor; wherein the PA reactor is located upstream of the AD reactor when the PA reactor is present;

wherein the WWTP is further comprised of an AD online EKF having an online dynamic model of the AD when the AD is present; wherein the online dynamic model of the AD is comprised of states, process material balances, energy balances, and bio-chemical reaction kinetics, estimated parameters, and adapted online model parameters; wherein the adapted model parameters are a subset of the estimated parameters; wherein the AD reactor and the PA reactor are modeled separately when both of the AD reactor and the PA reactor are present;

wherein the MBR is comprised of an aerobic tank, a membrane tank, an MBR control system, and optionally an anoxic tank; wherein the aerobic tank is located upstream of the membrane tank; wherein the anoxic tank is located either immediately upstream or downstream of the aerobic tank when the anoxic tank is present;

wherein the WWTP is further comprised of an MBR online EKF having an online dynamic model of the MBR when the MBR is present; wherein the online dynamic model of the MBR is comprised of estimated parameters, adapted model parameters, states, process material balances, energy balances and bio-chemical reaction kinetics; wherein the adapted model parameters are a subset of the estimated parameters; wherein the aerobic tank and the anoxic tank are modeled separately when both of the aerobic and the anoxic tanks are present.

In another aspect of the WWTP, the AD control system is comprised of an AD supervisory control system and an AD low-level control system.

In another aspect of the WWTP, the AD supervisory control system is comprised of at least one of an AD reactor pH supervisory controller, a PA reactor pH supervisory controller, or an PA:AD overall recycle flow ratio supervisory controller.

In another aspect of the WWTP, the AD reactor pH supervisory controller is comprised of an AD reactor nonlinear PI pH controller and an AD reactor P alkalinity controller in a cascaded configuration; wherein the PA reactor pH supervisory controller is comprised of a PA reactor nonlinear PI pH controller and a PA reactor P alkalinity controller in a cascaded configuration; wherein the PA:AD overall recycle flow ratio supervisory controller is comprised of a AD:PA Recycle ratio controller, and a PA reactor and AD reactor recycle flow rate controller.

In another aspect of the WWTP, the AD low-level control system is comprised of at least one of an AD reactor biomass controller, a PA reactor fluid level controller, a PA reactor nutritional additive concentration controller, or an AD reactor nutritional additive concentration controller.

In another aspect of the WWTP, the MBR control system is comprised of an MBR supervisory control system and an MBR low-level control system.

In another aspect of the WWTP, the MBR supervisory control system is comprised of at least one of an aerobic tank DO supervisory controller, anoxic tank recycle flow supervisory controller, or an anoxic tank bCOD addition flow rate supervisory control scheme.

In another aspect of the WWTP, the anoxic tank bCOD addition flow supervisory control scheme of the MBR is comprised of an anoxic tank bCOD setpoint supervisory controller, an anoxic tank bCOD addition flow rate supervisory feedback controller, and an anoxic tank bCOD addition flow rate supervisory feedforward controller.

In another aspect of the WWTP, the MBR low-level control system is comprised of at least one of an aerobic tank fluid level PI controller, an aerobic tank pH controller, an anoxic tank pH controller, an anoxic tank recycle line flow rate controller, an aerobic tank DO concentration controller, an anoxic tank nutritional additive concentration controller, an aerobic tank recycle line flow rate PI controller, a total MBR recycle flow rate PI controller, an aerobic tank recycle flow rate lookup table, or a membrane tank MLSS concentration controller.

In another aspect of the WWTP, the AD is comprised of a mixing stage and at least one recycle line.

In another aspect of the WWTP, the AD reactor is a CSTR, UASB, EGSB, mixed bed, moving bed, low-rate, or high-rate reactor; wherein the at least one recycle line of the AD is a PA reactor recycle line or an AD reactor recycle line.

In another aspect of the WWTP, the MBR is further comprised of a mixer and at least one recycle line.

In another aspect of the WWTP, at least one recycle line of the MBR is an anoxic tank recycle line or an aerobic tank recycle line.

In another aspect of the WWTP, at least one of the AD online EKF, MBR online EKF, AD control system, or MBR control system is implemented using a computer.

In yet another aspect of the invention, a system for monitoring and controlling a WWTP comprised of at least one of an AD or an MBR was discovered. The system is comprised of memory and a microprocessor operable connected with the memory. Wherein said microprocessor is configured to when said MBR is present: update adapted model parameters of an online dynamic model of said MBR and estimate model based inferred variables of said MBR using an MBR online EKF, said online dynamic model of said MBR, real time measured input data of said MBR, and real time measured output data of said MBR; wherein said MBR online EKF, and said online dynamic model of said MBR are stored in the memory and executed by the microprocessor; and control said MBR using an MBR control system, one or more of said real time measured input data of said MBR, said real time measured output data of said MBR, said adapted model parameters of said online dynamic model of said MBR, or said model based inferred variables of said MBR. Wherein said microprocessor is further configured to when said AD is present: update adapted model parameters of an online dynamic model of said AD and estimate model based inferred variables of said AD using an AD online EKF, said online dynamic model of said AD, real time measured input data of said AD, and real time measured output data of said AD; wherein said AD online EKF, and said online dynamic model of said AD are stored in the memory and executed by the microprocessor; and control said AD using an AD control system, one or more of said real time measured input data of said AD, said real time measured output data of said AD, said adapted model parameters of said online dynamic model of said AD, or said model based inferred variables of said AD.

Advantages of the present invention will become more apparent to those skilled in the art from the following description of the embodiments of the invention which have been shown and described by way of illustration. As will be realized, the invention is capable of other and different embodiments, and its details are capable of modification in various respects.

BRIEF DESCRIPTION OF SEVERAL VIEWS OF THE DRAWINGS

These and other features of the present invention, and their advantages, are illustrated specifically in embodiments of the invention now to be described, by way of example, with reference to the accompanying diagrammatic drawings, in which.

Figure 1A:
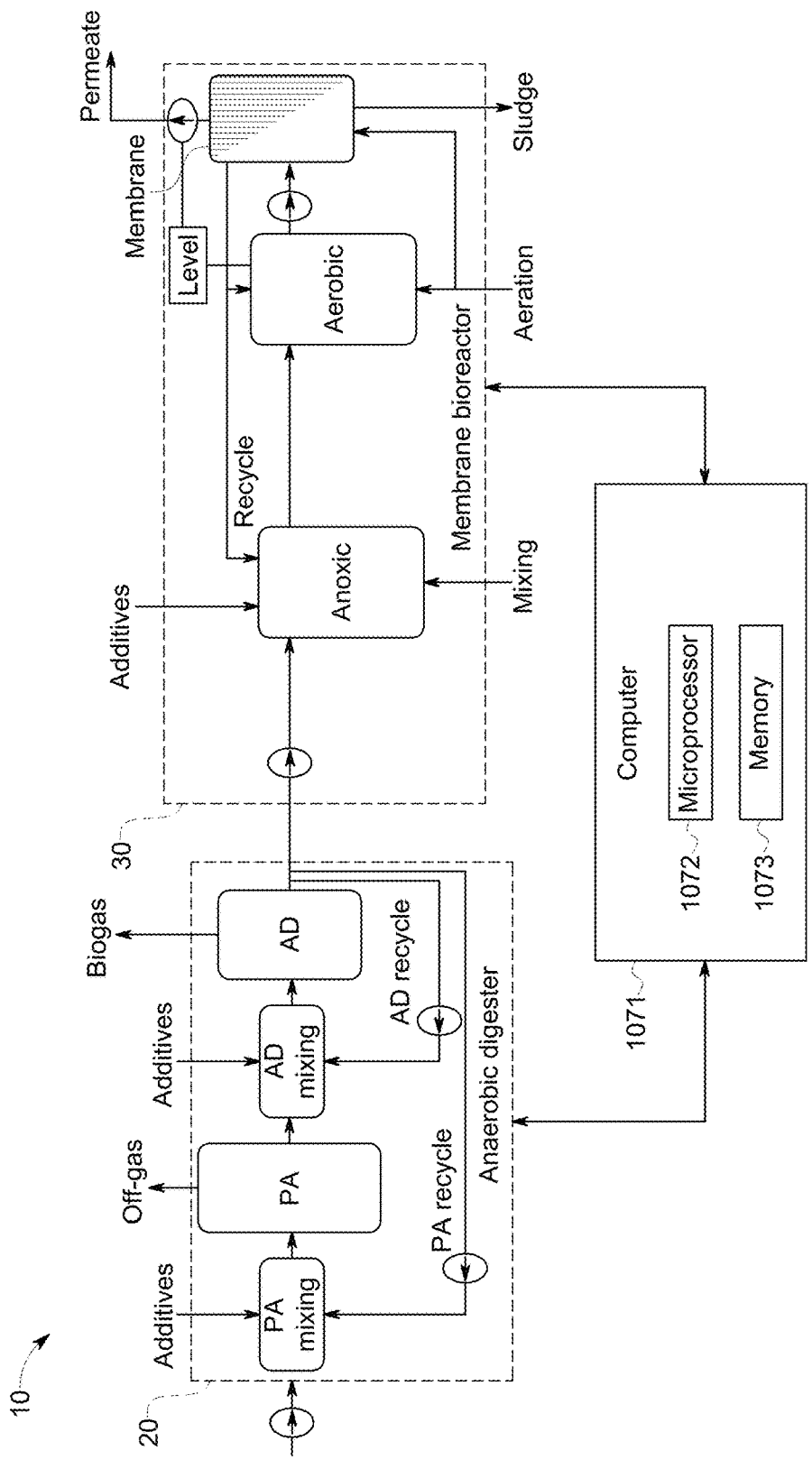
FIG. 1a is a block diagram of an exemplary wastewater treatment plant, in accordance with aspects of the present technique.

It should be noted that all the drawings are diagrammatic and not drawn to scale. Relative dimensions and proportions of parts of these Figures have been shown exaggerated or reduced in size for the sake of clarity and convenience in the drawings. The same reference numbers are generally used to refer to corresponding or similar features in the different embodiments. Accordingly, the drawing(s) and description are to be regarded as illustrative in nature and not as restrictive.

DETAILED DESCRIPTION OF THE PREFERRED EMBODIMENT

Approximating language, as used herein throughout the specification and claims, may be applied to modify any quantitative representation that could permissibly vary without resulting in a change in the basic function to which it is related. Accordingly, a value modified by a term or terms, such as "about", is not limited to the precise value specified. In at least some instances, the approximating language may correspond to the precision of an instrument for measuring the value. Range limitations may be combined and/or interchanged, and such ranges are identified and include all the sub-ranges stated herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about".

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present.

As used herein, the terms "comprises", "comprising", "includes", "including", "has", "having", or any other variation thereof, are intended to cover a non-exclusive inclusion. For example, a process, method, article or apparatus that comprises a list of elements is not necessarily limited to only those elements, but may include other elements not expressly listed or inherent to such process, method, article, or apparatus.

The singular forms "a", "an", and "the" include plural referents unless the context clearly dictates otherwise.

FIG. 1a shows a general integrated wastewater treatment plant (WWTP) 10. The wastewater is fed to the anaerobic digester (AD) 20, where typically 80-90% of the readily biodegradable COD is converted to biogas. The anaerobic digester effluent is then treated in the membrane bioreactor (MBR) 30 to eliminate the remaining COD through aerobic bio-treatment. For wastewater feeds with high solids content, an entrapped air flotation process 48 is used to remove the particulate solid before feeding to the MBR 30. Entrapped air flotation process 48 can be located immediately before MBR 30 or immediately inside MBR 30 upstream of aerobic tank 32 and anoxic tank 31, if present. The MBR 30 removes COD, nitrogen, phosphorus, and total suspended solids (TSS) to yield the clean permeate water. The MBR 30 allows for the recovery of 90-95% of the water in wastewater as cleaned permeate water.

WWTP 10 is further comprised of a computer 1071 containing microprocessor 1072 and memory 1073. The AD online EKF 252, AD offline EKF 251, AD online dynamic model 262, AD offline dynamic model 261, MBR online EKF 352, MBR offline EKF 351, MBR online dynamic model 362, MBR offline dynamic model 361, and methods for operating AD 20 and MBR 30 are contained in the memory 1073 of computer 1071. The real time operation data of AD 20 and MBR 30 and offline laboratory testing results for AD 20 and MBR 30 is also stored in the memory 1073 of computer 1071 and used later as historical operation data. Microprocessor 1072 retrieves from memory 1073 and executes the methods of operating AD 20 and MBR 30 discussed below. It is contemplated that computer 1071 can be any device, or devices, deemed suitable by a person having ordinary skill in the art that has microprocessor 1072 and memory 1073, including, but not limited to, a general purpose computer, a local computer, a remote computer, a cloud based computer, or a PLC. Further, it is also contemplated in some embodiments, computer 1071 also contains operator control panel 1070.

Figure 1B:
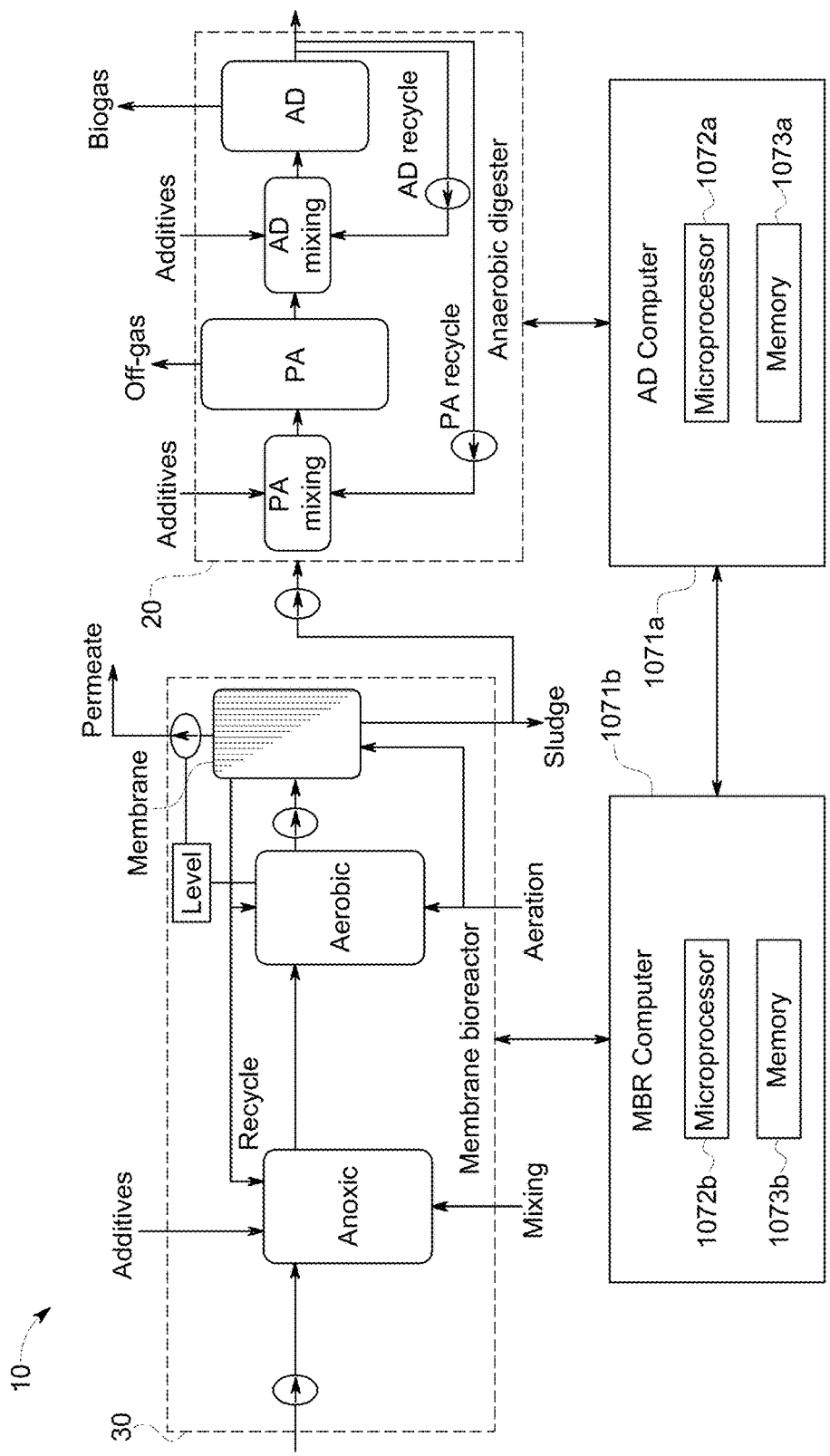
FIG. 1b is a block diagram of an exemplary wastewater treatment plant, in accordance with aspects of the present technique.

FIG. 1b shows an alternative embodiment of WWTP 10 in which MBR 30 is located upstream of AD 20. In this embodiment, AD 20 receives the effluent from membrane tank sludge discharge 43 of MBR 30. It is contemplated that in some embodiments of WWTP 10, AD 20 has an AD computer 1071a and MBR 30 has an MBR computer 1071b, or alternatively only one of AD computer 1071a or MBR computer 1071b is present in WWTP if only one of AD 20 or MBR 30 is present in WWTP 10. When both are present, AD computer 1071a and MBR computer 1071b are networked together to share information. AD computer contains microprocessor 1072a and memory 1073a. MBR computer contains microprocessor 1072b and memory 1073b.

The AD online EKF 252, AD offline EKF 251, AD online dynamic model 262, AD offline dynamic model 261, method for operating AD 20 is contained in the memory 1073a of AD computer 1071a. The real time operation data of AD 20 offline laboratory testing results for AD 20 are also stored in the memory 1073a of AD computer 1071a and used later as historical operation data. Microprocessor 1072a retrieves from memory 1073a and executes a method of operating AD 20 discussed below.

The MBR online EKF 352, MBR offline EKF 351, MBR online dynamic model 362, MBR offline dynamic model 361, and method MBR 30 are contained in the memory 1073b of MBR computer 1071b. The real time operation data of MBR 30 and offline laboratory testing results for MBR 30 are also stored in the memory 1073 of computer 1071 and used later as historical operation data. Microprocessor 1072b retrieves from memory 1073b and executes a method of operating MBR 30 discussed below.

It is contemplated that AD computer 1071a and MBR computer 1071b can be any device, or devices, deemed suitable by a person having ordinary skill in the art that has microprocessor 1072 and memory 1073, including, but not limited to, a general purpose computer, a local computer, a remote computer, a could based computer, a PLC. Further, it is also contemplated in some embodiments, one or both of AD computer 1071a and MBR computer 1071b also contain operator control panel 1070.

In one embodiment, the computer 1071 and the WWTP 10 form a system for monitoring and controlling the WWTP 10 comprised of at least one of an AD 20 or an MBR 30, a memory 1073, and a microprocessor 1072 operable connected with the memory 1073, wherein the microprocessor 1072 is configured to, when the MBR 30 is present, update adapted model parameters of an online dynamic model 362 of the MBR 30 and estimate model based inferred variables of the MBR 30: using an MBR online EKF 352, the online dynamic model 362 of the MBR 30, real time measured input data of the MBR 30, and real time measured output data of the MBR 30. The MBR online EKF 352, and the online dynamic model 362 of the MBR 30 are stored in the memory 1073 and executed by the microprocessor 1072. Microprocessor 1072 is further configured to, when the MBR 30 is present, control the MBR 30 using an MBR control system 300, and one or more of: the real time measured input data of the MBR 30, the real time measured output data of the MBR 30, the adapted model parameters of the online dynamic model of the MBR 30, or the model based inferred variables of the MBR 30.

Wherein the microprocessor 1072 is further configured to, when the AD 20 is present, update adapted model parameters of an online dynamic model 262 of the AD 20 and estimate model based inferred variables of the AD 20 using: an AD online EKF 252, the online dynamic model 262 of the AD 20, real time measured input data of the AD 20, and real time measured output data of the AD 20. The AD online EKF 252, and the online dynamic model 262 of the AD 20 are stored in the memory 1073 and executed by the microprocessor 1072. The microprocessor 1072 is further configured to, when the AD 20 is present, control the AD 20 using an AD control system 200, and one or more of: the real time measured input data of the AD, the real time measured output data of the AD, the adapted model parameters of the online dynamic model of the AD, or the model based inferred variables of the AD.

In another embodiment, one or both of AD computer 1071a and MBR computer 1071b, and the WWTP 10 form a system for monitoring and controlling the WWTP 10. The system is comprised of at least one of an AD 20 or an MBR 30. The system has an AD computer 1071a if the AD 20 is present, and an MBR computer 1071b if the MBR 30 is present. If present, the AD computer 1071a is comprised of memory 1073a and a microprocessor 1072a operable connected with the memory 1073a. If present, the MBR computer 1071*b* is comprised of memory 1073*b* and a microprocessor 1072*b* operable connected with the memory 1073*b*.

Wherein, when the MBR 30 and the MBR computer 1071*b* are present, the microprocessor 1072*b* is configured to update adapted model parameters of an online dynamic model 362 of the MBR 30 and estimate model based inferred variables of the MBR 30: using an MBR online EKF 352, the online dynamic model 362 of the MBR 30, real time measured input data of the MBR 30, and real time measured output data of the MBR 30. The MBR online EKF 352 and the online dynamic model 362 of the MBR 30 are stored in the memory 1073*b* and executed by the microprocessor 1072*b*. MBR microprocessor 1072*b* is further configured to control the MBR 30 using an MBR control system 300, and one or more of: the real time measured input data of the MBR 30, the real time measured output data of the MBR 30, the adapted model parameters of the online dynamic model of the MBR 30, or the model based inferred variables of the MBR 30.

Wherein, when the AD 20 and the AD computer 1071*a* are present, the microprocessor 1072*a* is further configured to update adapted model parameters of an online dynamic model 262 of the AD 20 and estimate model based inferred variables of the AD 20 using: an AD online EKF 252, the online dynamic model 262 of the AD 20, real time measured input data of the AD 20, and real time measured output data of the AD 20. The AD online EKF 252 and the online dynamic model 262 of the AD 20 are stored in the memory 1073*a* and executed by the microprocessor 1072*a*. AD microprocessor 1072*a* is further configured to control the AD 20 using an AD control system 200, and one or more of: the real time measured input data of the AD, the real time measured output data of the AD, the adapted model parameters of the online dynamic model of the AD, or the model based inferred variables of the AD.

One challenge for operating the AD 20 and MBR 30 in a unified and seamless manner is the presence of variations in the wastewater feed flow and composition. For example, operation of AD 20 is sensitive to temperature and pH variations and could go unstable in the presence of sustained excursions in these parameters beyond normal operations conditions. Thus, typically, pH is regulated in an AD 20. Additional controls sometimes found in an AD include active regulation of wastewater feed and effluent flow rates and nutrient addition, and in some cases regulation of AD temperature. However, there is no direct control of COD conversion and often the biogas flow rate and composition are not monitored or regulated.

Figure 2:
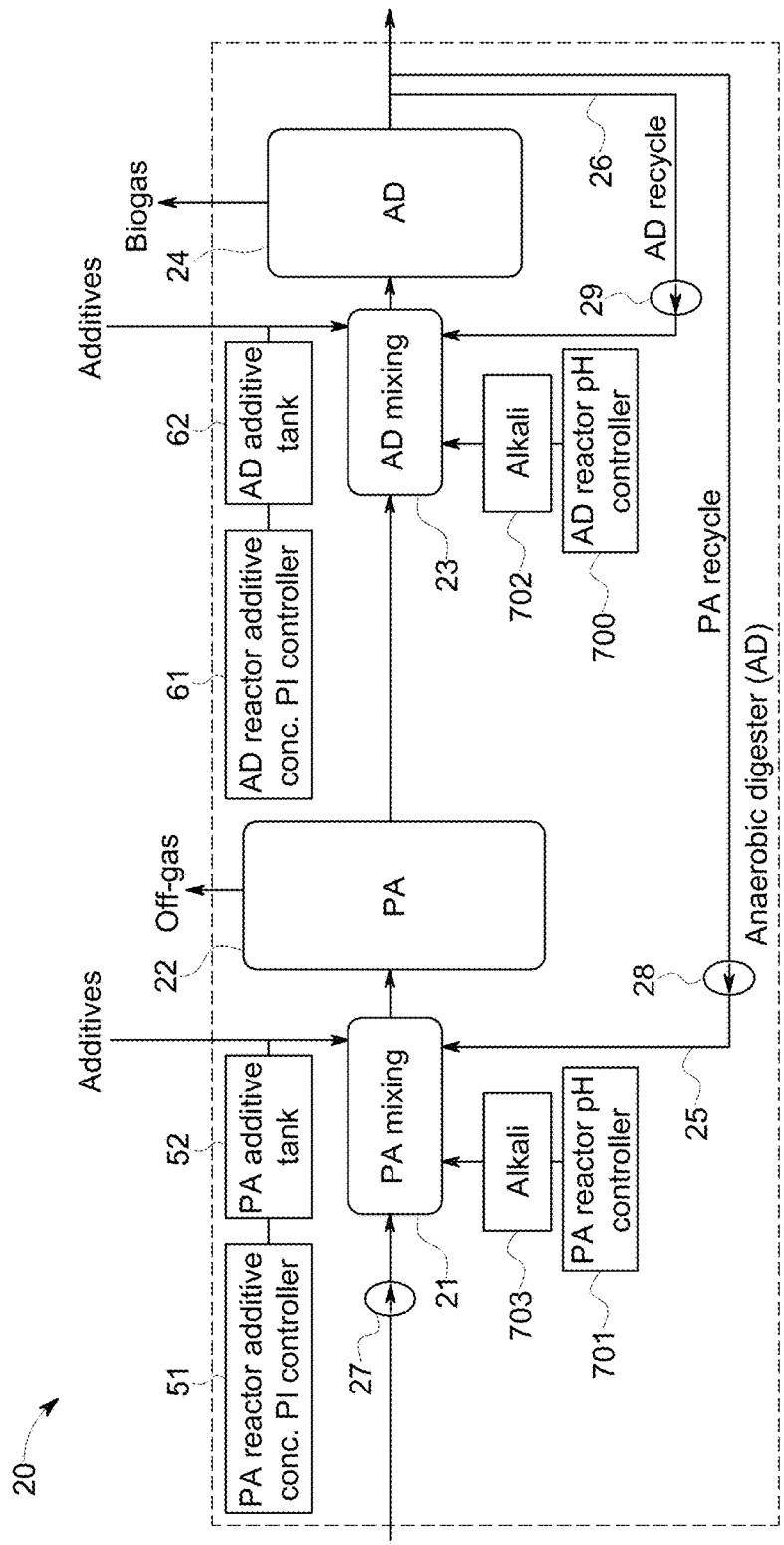
FIG. 2 is a block diagram of an exemplary anaerobic digester (AD) in accordance with aspects of the present technique.

FIG. 2 shows a general anaerobic digester 20 having a pre-acidification (PA) reactor 22, PA reactor mixing stage 21, AD reactor mixing stage 23 and AD reactor 24. The wastewater is fed to AD 20 first enters the PA reactor mixing stage 21 where additives are mixed with the wastewater before it enters the PA reactor 22. The PA effluent enters the AD reactor mixing stage 23 where additives are mixed with the PA effluent before it enters the AD reactor 24. PA reactor 22 acts as an equalization tank and allows a partial acidification of the soluble (primary carbohydrate) COD to yield volatile fatty acids (VFA)s, thus also acting as a pre-acidification tank. The mixed carbohydrate and VFA feed is converted to methane in the AD reactor 24. Due to the acidification and buildup of VFA, the PA reactor 22 operates at a fairly low pH (about 6.0), which is not suitable for methanogenesis. The AD reactor 24 is operated at a higher pH (between about 6.5 to 7.5) to favor the methanogenesis. The pH in the PA reactor 22 and AD reactor 24 are regulated by addition of suitable alkali addition at AD reactor mixing stage 23 and PA reactor mixing stage 21, or PA reactor 22 and AD reactor 24 if the AD reactor mixing stage 23 and PA reactor mixing stage 21 are not present. Such suitable alkali addition may include, but is not limited to, one or more of caustic, sodium bicarbonate, and magnesium hydroxide. It is contemplated that AD reactor pH supervisory controller 700 will control the flow rate of alkali from AD alkali tank 702 to AD reactor 24, either directly to AD reactor 24 or via AD reactor mixing stage 23. Further, it is contemplated that PA reactor pH supervisory controller 701 will control the flow rate of alkali from PA alkali tank 703 to PA reactor 22, either directly to PA reactor 22 or via PA reactor mixing stage 21. In some embodiments, an AD feed pump 27 is present. In some embodiments of AD 20, nutritional additives are provided to PA reactor 22 and AD reactor 24, either directly to PA reactor 22 and AD reactor 24 or via PA reactor mixing stage 21 and AD reactor mixing stage 23. The nutritional additives provided to PA reactor 22 are provided from PA reactor nutritional additive tank 52, whose flow rate is controlled by PA reactor nutritional additive concentration controller 51. The nutritional additives provided to AD reactor 24 are provided from AD reactor nutritional additive tank 62, whose flow rate is controlled by AD reactor nutritional additive concentration controller 61.

It is understood that in some embodiments of AD 20 each nutritional additive for PA reactor 22 will have a PA reactor nutritional additive tank 52 and PA reactor nutritional additive concentration controller 51. Along the same lines, each nutritional additive for AD reactor 24 will have a PA reactor nutritional additive tank 52 and PA reactor nutritional additive concentration controller 51.

However, in other embodiments of AD 20, all of the nutritional additives for PA reactor 22 are combined in a single PA reactor nutritional additive tank 52 and all of the nutritional additives for AD reactor 24 are combined in a single AD reactor nutritional additive tank 62. Accordingly, only one PA reactor nutritional additive tank 52 and corresponding PA reactor nutritional additive concentration controller 51 are present, and only one AD reactor nutritional additive tank 62 and corresponding AD reactor nutritional additive concentration controller 61 are present.

In some embodiments, an PA recycle line 25 having a PA recycle pump 28 is located between the AD reactor 24 and PA reactor 22 to mix a portion of effluent from AD reactor 24 into the influent of PA reactor 22, thereby allowing regulation for hydraulic load variations and also dilution of the incoming wastewater. In one embodiment, this is accomplished by placing a recycle line from the AD reactor 24 effluent to PA reactor mixing stage 21. Further, in some embodiments, such as those using an EGSB AD reactor 24, an AD recycle line 26 having an AD recycle pump 29 is present around the AD reactor 24 itself. In one embodiment, this is accomplished by placing a recycle line from AD reactor 24 effluent to AD reactor mixing stage 23.

PA reactor mixing stage 21 and PA reactor 22 are optional. However, they are often present when AD reactor 24 is a high-rate digester. It is contemplated that AD reactor 24 can be one of several types of reactors, including, but not limited to a be a continuously stirred tank reactor (CSTR), upflow anaerobic sludge blanket reactor (UASB), expanded granular sludge bed reactor (EGSB), mixed bed, moving bed, low-rate, or high-rate reactor.

Anaerobic digesters have been studied quite extensively over the last several decades and have recently attracted efforts on modeling, focusing primarily on offline simulation studies. There is a highly detailed model available for anaerobic digesters, Anaerobic Digesters Model 1 (ADM1), developed by the International Water Association, and is used as a reference standard for describing the dynamic operation of anaerobic digesters. The ADM1 is a comprehensive and detailed model with seven reaction paths, 19 reactions, and 3 inhibition effects, designed for very general waste content and broad operation conditions. While the ADM1 has broad applicability, it is complex and not readily useable for online monitoring and control. In particular, it includes detailed dynamics in liquid and gas phases spanning multiple time-scales leading to a very stiff model with some fast dynamics that are not practically important for the overall bioprocess operation.

In contrast to the detailed ADM1, a "6-state" simple model (6th order model—includes 6 dynamic components) has been proposed and used by Bernard in a paper, *Dynamical Model Development and Parameter Identification for an Anaerobic Wastewater Treatment Process*, Biotechnology and Bioengineering, Vol. 75, pp 424-438, 2001. The 6-state model simplifies the AD process as acidification and methanation in two sequential reaction steps with acidogenesis and methanogenesis microbes converting from COD to volatile fatty acids (VFA), and from VFA to methane, respectively. The six components modeled dynamically are: COD, VFA, inorganic carbon, alkalinity, acidogenesis microbes and methanogenesis microbes. While this model is very simple, it is too restricted in applicability to primary soluble carbohydrates in the wastewater feed COD, and does not account for nitrogen balance or acid-base equilibrium for pH calculations and effects on pH on the bioprocess.

A more reasonable "10-state" model (10th order model—includes 10 dynamic components) of intermediate complexity has been proposed and used as a starting point. This model is described in Dochain, *Dynamical modelling, analysis, monitoring, and control design for nonlinear bioprocesses*, survey chapter in *Advances in Biochemical Engineering*, Vol. 56, Springer-Verlag Berlin Heidelberg, 1997; Dochain, *Adaptive control of the hydrogen concentration in anaerobic digestion*, Industrial and Engineering Chemistry Research, 1991, 30, 129-136; and Mosey, *Mathematical Modelling of the Anaerobic Digestion Process: Regulatory Mechanisms for the Formation of Short-Chain Volatile Acids from Glucose*, Water Science Technology, 1983, 15, 209-232.

The 10-state model has a little more detail on the bioprocess compared to the 6-state model—modeling in more detail the reaction pathways for acedogenesis, acetogenesis and the final methanogenesis. It assumes the process to start with simple carbohydrate (e.g. glucose), and identifies 4 reaction paths: 2 for acidification and 2 for methanation. The 10 components modeled dynamically are: COD, propionate, acetate, hydrogen, inorganic carbon, acidogenic biomass, OHPA (Obligate Hydrogen Producing Acidogens), acetoclastic methanogenic biomass, hydrogenophilic methanogenic biomass, and methane. In total, 26 parameters are used for the bio-reaction kinetics and the yield coefficients. However, this model captures most, but not all, of the important processes and the important components. We have found that it is also necessary to extend the 10-state model to include additional detail to allow more general applicability to ADs beyond brewery/winery applications. In particular, the 10-state model has been extended to (i) include fats (LCFA) and proteins (amino acids) in addition to carbohydrates (glucose) as soluble COD, (ii) include particulate or insoluble biodegradable and non-biodegradable/inert (i.e. refractory) COD, (iii) include biomass decay, (iv) include nitrogen balance, and (v) include alkalinity and inorganic carbon balance for pH calculation and its effect on the bioprocess kinetics. The overall material conversion scheme in the final model used is shown in FIG. 3, and the dynamic material balance is shown in Eq. 3.

Figure 3:
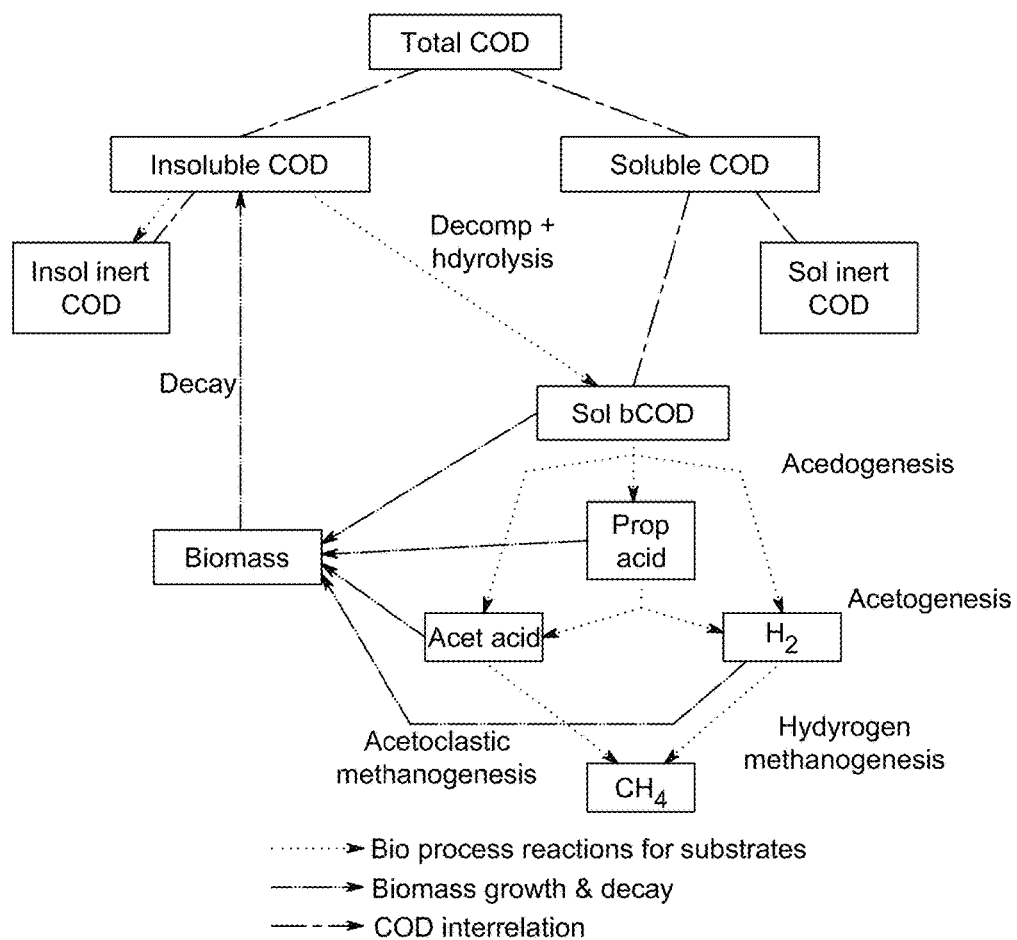
FIG. 3 is a material conversion block diagram in the model of the anaerobic digester to be used for control design and system monitoring accordance with aspects of the present technique.

As can be seen, the scheme of FIG. 3 has been extended to include soluble and insoluble, as well as biodegradable and inert (refractory) COD. Further, insoluble (particulate) COD with first order kinetics for decomposition and hydrolysis has been added to the model. Decomposition yields insoluble inert and insoluble bCOD. Insoluble bCOD undergoes hydrolysis to Sol bCOD. Additionally, decomposition and hydrolysis are both first order reactions—combined together (hydrolysis is an order of magnitude faster than decomposition). Further, bCOD is biodegradable COD, a mixture of carbohydrates (glucose), fat (LCFA) and protein (amino acids)—COD fractions $f_c$, $f_f$ and $f_p$.

Further, in the scheme of FIG. 3, all higher order (than acetic) fatty acids are combined into propionic acid, and biomass decay was added to reduce active biomass. As can be seen in FIG. 3, biomass in the diagram denotes active biomass only. Accordingly, the scheme of FIG. 3 can also include N-balance.

The bio-chemical reactions in AD reactor 24 are modeled starting from soluble biodegradable COD (denoted as SbCOD), the four reactions R1-R4 show below are modeled:

$R1$: SbCOD→Prop acid+Acet acid+$H_2$+$CO_2$ $R2$: Prop acid→Acet acid+$CO_2$+$H_2$ $R3$: Acet acid→Methane+$CO_2$ $R4$: $CO_2$+$H_2$→Methane  Eq 1

SbCOD=mix of glucose, LCFA/alcohol, amino acid

In the above simplified reaction scheme, R1 denotes the acedogenesis reaction from a mixed soluble bCOD, R2 denotes the acetogenesis reaction, R3 denotes the acetoclastic methanogenesis and R4 denotes the methanogenesis from hydrogen. In general, the substrate for the first reaction will be a mix of carbohydrates (glucose), fats (long chain fatty acids—LCFA and alcohol) and proteins (amino acid). To allow the applicability for general processes, the carbohydrates, fats and proteins are modeled distinctly with the respective individual reactions (alcohol can be lumped together with fats owing to similar reaction stoichiometry):

$R1a$: Glucose→Prop acid+Acet acid+$H_2$+$CO_2$ $R1b$: LCFA/Ethanol→Acet acid+$H_2$ $R1c$: Amino acid→Prop acid+Acet acid+$H_2$+$CO_2$(+ IN)  Eq2

The separate modeling for the carbohydrates, fats and proteins was also important to allow a more accurate total carbon balance, which in turn, is used in the inorganic carbon balance for calculation of alkalinity, $CO_2$ and pH. Finally, the model was updated to include the decay of the active biomass, as a first order reaction, wherein the active biomass decays to yield insoluble COD. The insoluble or particulate COD, in turn, undergoes a slow decomposition and hydrolysis through a first order reaction to yield insoluble inert COD and soluble biodegradable COD.

For the above-mentioned bioprocess the overall dynamic model of the digester is given by:

$$\dot{X}_C = D(X_{C,in} - \alpha X_C) + b(X_1 + X_2 + X_3 + X_4) - hX_C \quad \text{Eq 3}$$

$$\dot{X}_I = D(X_{I,in} - \alpha X_I) + (1 - f_B)hX_C$$

$$\dot{X}_1 = D(X_{1,in} - \alpha X_1) + k_1 r_1 X_1 - bX_1$$

$$\dot{X}_2 = D(X_{2,in} - \alpha X_2) + k_2 r_2 X_2 - bX_2$$

$$\dot{X}_3 = D(X_{3,in} - \alpha X_3) + k_3 r_3 X_3 - bX_3$$

$$\dot{X}_4 = D(X_{4,in} - \alpha X_4) + k_4 r_4 X_4 - bX_4$$

$$\dot{S}_I = D(S_{I,in} - S_I)$$

$$\dot{S}_1 = D(S_{1,in} - S_1) - r_1 X_1 + f_B h X_C$$

$$\dot{S}_2 = D(S_{2,in} - S_2) + k_5 r_1 X_1 - r_2 X_2$$

$$\dot{S}_3 = D(S_{3,in} - S_3) + k_6 r_1 X_1 + k_7 r_2 X_2 - r_3 X_3$$

$$\dot{S}_4 = D(S_{4,in} - S_4) + (k_8 r_1 X_1 + k_9 r_2 X_2 - r_4 X_4 - q_{H_2}) * (10^6 / MW_{H_2})$$

$$\dot{S}_5 = D(S_{5,in} - S_5) + (k_{10} r_1 X_1 + k_{11} r_2 X_2 + k_{12} r_3 X_3 - k_{13} r_4 X_4 - q_{CO_2})/MW_{CO_2}$$

$$\dot{Z} = D(Z_{in} - Z) + Z_{gen}$$

$$\dot{S}_{IN} = D(S_{IN,in} - S_{IN}) + N_{gen} - N_{bac}\left(\sum_{i=1}^{4} k_i \mu_i X_i\right)$$

In the above model, $X_C$ denotes the insoluble COD concentration, $X_I$ denotes the insoluble inert COD concentration, $X_i$ (i=1, . . . , 4) denotes the concentration of the biomass for the $i^{th}$ reaction, $S_I$ denotes the soluble inert COD concentration, $S_1$ denotes the soluble biodegradable COD, $S_2$ denotes propionic acid concentration (higher order VFA are ignored and lumped into propionic acid), $S_3$ denotes acetic acid concentration, $S_4$ denotes dissolved $H_2$ concentration, $S_5$ denotes the total inorganic carbon concentration, Z denotes the total alkalinity and $S_{IN}$ denotes the total inorganic nitrogen concentration. All concentrations in the model are expressed in gCOD/l, except $S_4$ is in micromol/l, while $S_5$ and $S_{IN}$ are in mol/l, and Z is expressed as equivalent g $CaCO_3$/l. The variable D denotes the dilution rate, or the inverse of the hydraulic retention time (HRT), the parameter b denotes the rate constant for biomass decay, h denotes the net first-order reaction rate constant for decomposition/hydrolysis, while $f_B$ denotes the fraction of insoluble COD that yields soluble biodegradable COD upon decomposition/hydrolysis—the remaining fraction is insoluble inert COD.

The total inorganic carbon consists of dissolved $CO_2$ and bicarbonate—at the operating pH range of 6.5-7.5 (or lower in the PA reactor) the carbonate concentration is ignored. The total alkalinity includes alkalinity due to dissolved bicarbonate, and due to ionized VFA. At operating pH above 6.5, it is assumed that all VFA is ionized, whereas at lower pH conditions in the PA reactor, VFA is partially ionized depending on the dissociation equilibrium. Finally, total inorganic nitrogen is the nitrogen as $NH_3/NH_4^+$ in the reactor. At pH below 7.5, all inorganic nitrogen is present as $NH_4^+$. The inorganic nitrogen is accumulated in the reactor due to generation from uptake of proteinaceous COD, and simultaneously removed by assimilation into the biomass during their growth ($N_{bac}$ denotes the specific nitrogen uptake during biomass growth). The terms $r_i X_i$ denote the uptake rate of the key substrate in the respective reaction, and the corresponding biomass growth rates are given by $k_i r_i X_i$. Note that the parameter a denotes the ratio of concentration of the biomass/particulate matter in the effluent stream to the concentration in the reactor. For a mixed CSTR, with perfect mixing, this ratio is nominally 1. On the other hand for high-throughput digesters like UASB and EGSB, with preferential retention of biomass and particulate matter, this ratio is less than 1. This parameter allows adapting for varying AD design, and can be also interpreted as the ratio of HRT and solid retention time (SRT), i.e., α=HRT/SRT, a critical design and operation parameter for digester performance. This parameter can be adjusted/adapted for varying design/operating conditions.

The reaction stoichiometry parameters $k_i$, and the reaction rates $r_i$ can also be adjusted/adapted for varying feed and operation conditions. In particular, the reaction rate $r_i$ is given by a standard monod-expression with multiplicative terms for inhibition effects due to pH and $H_2$ concentrations:

$$r_i = r_{i,max}(T)\frac{S_i}{KS_i + S_i} I_{pH} \cdot I_{H_2} \quad \text{Eq 4}$$

$$r_{i,max}(T) = \bar{r}_{i,max} b_3 (T - T_{min})^2 (1 - \exp(c_3(T - T_{max})))$$

In the above relation, the max reaction rate for each substrate and the corresponding biomass growth rate is a function of the operating temperature. For mesophilic bacteria, the optimum temperature is about 35° C., and the peak reaction rate drops gradually at lower temperatures, and very sharply at higher temperatures as given by the two-term function in the above equation. The peak reaction rate parameter $\bar{r}_{i,max}$ can be adapted/adjusted. The inhibition terms $I_{pH}$ and $I_{H2}$ range from 1 (un-inhibited) to 0 (completely inhibited) over respective pH and dissolved $H_2$ concentration ranges, and they are modeled the same as in ADM1.

As mentioned above, the soluble biodegradable COD ($S_1$) is composed of the individual carbohydrates ($S_{1c}$), fats (including alcohol) ($S_{1f}$) and proteins ($S_{1p}$), i.e., $$S_1 = S_{1c} + S_{1f} + S_{1p} \quad \text{Eq 5}$$

and the corresponding reaction rate for R1 is given as:

$$r_1 = r_{1c} + r_{1f} + r_{1p} \quad \text{Eq 6}$$

$$r_{1c} = r_{1c,max}(T)\frac{S_{1c}}{KS_{1c} + S_{1c}} I_{pH} \cdot I_{H_2}$$

$$r_{1f} = r_{1f,max}(T)\frac{S_{1f}}{KS_{1f} + S_{1f}} I_{pH} \cdot I_{H_2}$$

$$r_{1p} = r_{1p,max}(T)\frac{S_{1p}}{KS_{1p} + S_{1p}} I_{pH} \cdot I_{H_2}$$

In the above model, the terms $q_{CO_2}$ and $q_{H_2}$ denote the mass transfer rate of $CO_2$ and $H_2$ from liquid phase to the gas phase. Due to the fast consumption of $H_2$ in the reaction R4, the concentration of dissolved $H_2$ is nominally very low, and thus, $q_{H_2}$ is also low and is ignored. On the other hand, $q_{CO_2}$ needs to be calculated to complete the inorganic carbon balance. This is accomplished by calculating the mass transfer of methane as:

$$q_{CH_4} = \frac{k_{14} r_3 X_3 + k_{15} r_4 X_4}{MW_{CH_4} COD2M_{CH_4}} \text{ (mol/l/day)} \quad \text{Eq 7}$$

i.e., all methane produced in $R_3$ and $R_4$ is assumed to transfer to gas phase due to the very low solubility of methane in water, and imposing vapor-liquid equilibrium. Assuming the gas phase is a mixture of methane, water vapor, and $CO_2$, and the partial pressure for $CO_2$ is given by Henry's law:

$$p_{CO_2} = k_H(T)CO_{2,aq} \text{ (atm)} \qquad \text{Eq 8}$$

$$CO_{2,aq} = (S_5 - B) \text{ (mol/l)}$$

$$B = \left[\frac{2Z}{MW_{CaCO_3}} - \frac{S_2}{COD2M_{S_2}MW_{S_2}} - \frac{S_3}{COD2M_{S_3}MW_{S_3}}\right]$$

the mass transfer rate for $CO_2$ can be calculated as:

$$q_{CH_4} = \left[\frac{p_{CO_2}(q_{CH_4}/MW_{CH_4})}{P_{CO_2} - P_{H_2O}}\right] \text{ (mol/l/day)} \qquad \text{Eq 9}$$

Finally, an important output for the digester model is the operating pH, which needs to be regulated in the desired operating range 6.5-7.5. In this operation range, the bicarbonate equilibrium is the dominant equilibrium that determines the buffer capacity of the holdup and the resulting pH given by:

$$pH = pK_1 + \log_{10}(B) - \log_{10}(CO_{2,aq}) \qquad \text{Eq 10}$$

where B denotes the concentration of dissolved bicarbonate (in mol/l). The above set of equations complete the model for the AD reactor. However, this model is very stiff, necessitating the use of variable step-size stiff solvers for numerical computation. This is not desirable for real-time implementation in a PLC for monitoring and control. A key source of the stiffness is the fast kinetics for the consumption of dissolved $H_2$ in R4, yielding very low concentration of $H_2$. In essence $H_2$ is an intermediate product from R1 & R2, which is consumed in R4 as fast as it is produced. This fast reaction and corresponding dynamics can be approximated by a quasi-steady-state condition:

$$0 = (k_8 r_1 X_1 + k_9 r_2 X_2 - r_4 X_4) \qquad \text{Eq 11}$$

which is solved iteratively for $S_4$.

The PA reactor model is similar to the AD model described above, except that R2, R3 and R4 are eliminated—these reactions are suppressed at the low operation pH in the PA reactor. Also, due to the suppressed methanogenesis reaction, the reaction stoichiometry for R1 is modified to convert all the $H_2COD$ into propionic acid COD—this is to account for the fact that owing to suppression of the $H_2$ consuming methanogenesis reaction, the acidification reactions will yield higher order VFAs. Additionally, owing to the typical operation pH of the PA reactor below 6, the inorganic carbon balance, and alkalinity, pH calculation is modified to include partial ionization of the VFAs. The ionization of the VFAs is given by the respective equilibriums for their dissociation, which is a function of pH, i.e., $$CO_{2,aq} = (S_5 - B) \text{ (mol/l)} \qquad \text{Eq 12}$$

$$B = \left[\frac{2Z}{MW_{CaCO_3}} - \left(\frac{Ka_2}{Ka_2 - 10^{-pH}}\right)\frac{S_2}{COD2M_{S_2}MW_{S_2}} - \left(\frac{Ka_3}{Ka_3 - 10^{-pH}}\right)\frac{S_3}{COD2M_{S_3}MW_{S_3}}\right] \text{ (mol/l)}$$

This leads to an iterative calculation for pH unlike in the digester, where at pH above 6.5, all of the VFA is assumed to be completely ionized. Also, the mass transfer of $CO_2$ from liquid to gas phase is calculated through a mass transfer correlation:

$$q_{CO_2} = k_{1a}(CO_{2,aq} - CO^*_2)(\text{mol/l/day}) \qquad \text{Eq 13}$$

where $CO_2^*$ denotes the equilibrium composition of dissolved $CO_2$ in gas phase corresponding to the off-gas from the PA reactor consisting primarily of $CO_2$.

Finally, the model includes chemical additives like NaOH, $Na_2CO_3$, $NaHCO_3$, $NH_3$, $NH_4Cl$, $Mg(OH)_2$. Each of these chemical additives is modeled as equivalent (in molar concentration) addition of inorganic carbon, alkalinity and/or inorganic nitrogen.

As can be seen, PA reactor 22 and AD reactor 24 are modeled separately in dynamic model 260 of AD 20, which serves as the basis for offline dynamic AD model 261 and online dynamic AD model 262. Accordingly, PA reactor 22 and AD reactor 24 are modeled separately in offline dynamic AD model 261 and online dynamic AD model 262.

Figure 4A:
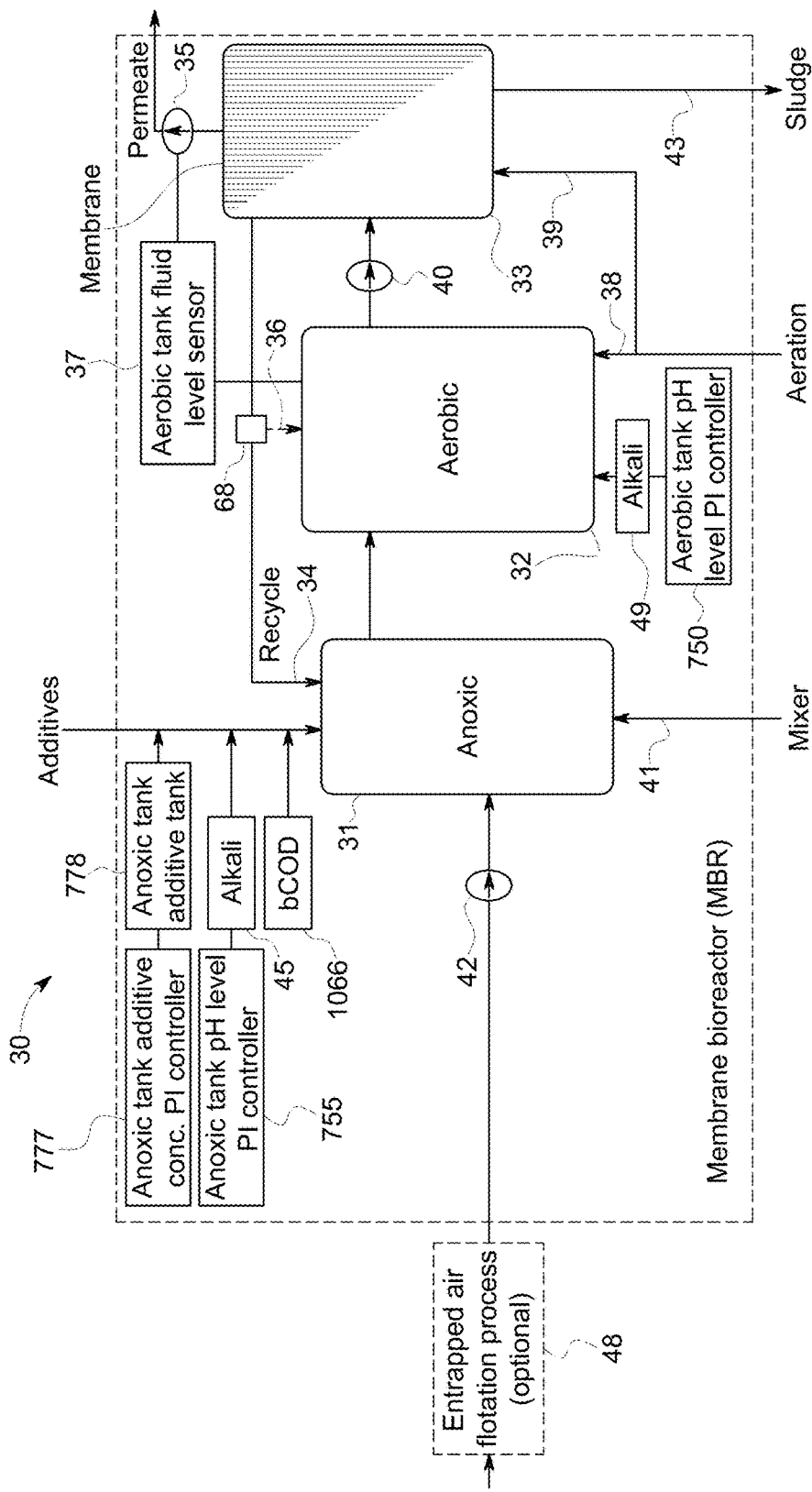
FIG. 4a is a block diagram of an exemplary membrane bioreactor in accordance with aspects of the present technique.
Figure 4B:
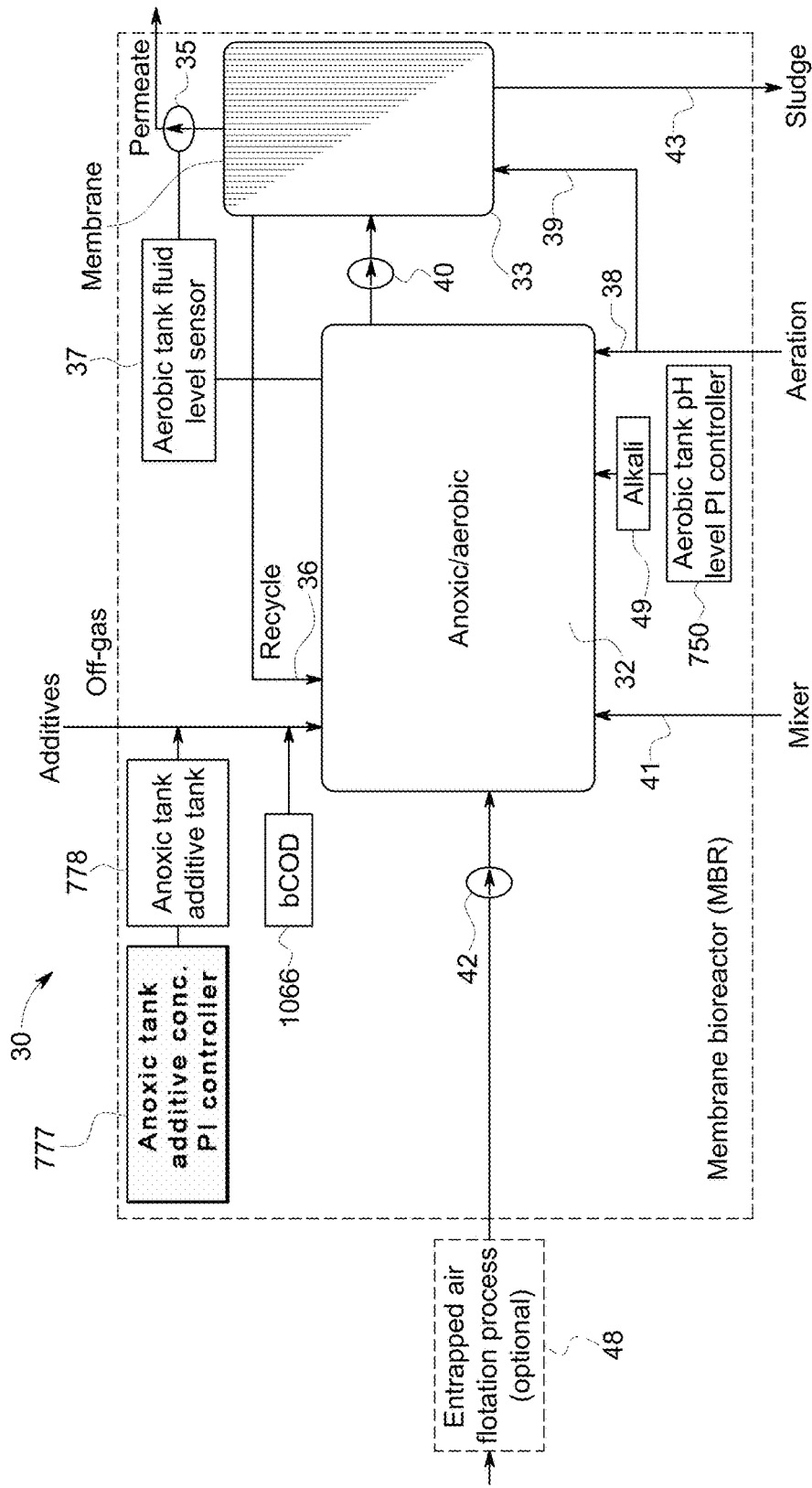
FIG. 4b is a block diagram of an exemplary membrane bioreactor in accordance with aspects of the present technique.

FIGS. 4a-b show a general MBR 30 having an anoxic tank 31, aerobic tank 32 and membrane tank 33 connected in series. The anoxic tank 31 is optional for feeds with high nitrogen. Aerobic tank 32 is for aerobic bio-chemical reactions to remove biodegradable COD in the waste water, and membrane tank 33 is for solids and liquids separation, and retains the biomass in the system. This configuration of MBR 30 largely represents the majority of MBR systems. MBR 30 is an aerobic/anoxic bioprocess used to remove remaining unconverted COD and nitrogen in the effluent of AD 20 if it is used to follow the AD 20 as shown in FIG. 1a. For wastewater feeds with high solids content, an entrapped air flotation process 48 is used to remove the particulate solid before feeding to the MBR 30. As can be seen, aerobic tank 32 is located upstream of membrane tank 33. Further, optional anoxic tank 31 is located either immediately upstream or downstream of said aerobic tank 32.

As can be seen, in a typical MBR 30, membrane tank 33 is at a higher elevation than anoxic tank 31 and aerobic tank 32. Recycle from membrane tank 33 flows back into anoxic tank 31 by overflow and gravity through the membrane tank to anoxic tank recycle line 34 and optional aerobic tank recycle line 36. In embodiments in which a stand along anoxic tank 31 is not present, recycle from membrane tank 33 is provided to aerobic tank 32 through aerobic tank recycle line 36. In some embodiments, an MBR recycle line flow diverter 68 is present, which changes the ratio of fluid flowing between anoxic tank recycle line 34 and aerobic tank recycle line 36.

The return activated sludge pump (RAS) 40 operates at R+1 times the feed-rate of influent into MBR 30, with R being the recycle ratio. The liquid level in the aerobic tank 32 is controlled at a desired level by the aerobic tank fluid level PI controller 765, described below, and an aerobic tank fluid level sensor 37 to detect the level of fluid in aerobic tank 32, which manipulate the flow rate of permeate pump 35 to maintain the fluid level in aerobic tank 32 at a predetermined level. Similarly, the dissolved oxygen DO concentration in the aerobic tank 32 is regulated by varying the speed of aerobic tank blower of aerobic and membrane tank aeration system 38 and 39, while the pH in the aerobic tank 32 is controlled by varying the alkali addition to aerobic tank 32. Aeration may also be applied to membrane tank. Anoxic tank 31 has a mixer 41. It is also contemplated that some embodiments of MBR 30 include an MBR feed pump 42 and a membrane tank sludge discharge 43.

In some embodiments of MBR 30, the pH of anoxic tank 31 is controlled by alkali addition from anoxic tank alkali tank 45, whose flow rate is controlled by anoxic tank pH controller 755. In some embodiments, anoxic tank pH controller 755 is a PI controller. Further, in some embodiments of MBR 30, the pH of aerobic tank 32 is controlled by alkali addition from aerobic tank alkali tank 49, whose flow rate is controlled by anoxic tank pH controller 755.

In some embodiments of MBR 30, nutritional additives are provided to anoxic tank 31. The nutritional additives provided to anoxic tank 31 are provided from anoxic tank additive tank 778, whose flow rate is controlled by anoxic tank nutritional additive concentration PI controller 777. It is understood that each nutritional additive for anoxic tank 31 will have a anoxic tank additive tank 778 and anoxic tank nutritional additive concentration PI controller 777. It is understood that each nutritional additive for anoxic tank 31 will have an anoxic tank additive tank 778 and an anoxic tank nutritional additive concentration PI controller 777.

However, in other embodiments of MBR 30, all of the nutritional additives for anoxic tank 31 are combined in a single anoxic tank additive tank 778. Accordingly, only one anoxic tank additive tank 778 and corresponding anoxic tank nutritional additive concentration PI controller 777 are present.

In embodiments in which a standalone anoxic tank 31 is not present, aerobic tank 32 will have both an anoxic zone and an aerobic zone. Anoxic zone acts as a pseudo anoxic tank 31 and aerobic zone acts as a pseudo aerobic tank 32. Accordingly, the nutritional requirements of aerobic tank 32 will be analyzed and any needed nutritional additives will be provided to aerobic tank 32.

Further, some embodiments of MBR 30 include a bCOD tank 1066 for providing additional bCOD to anoxic tank 31 if the feed has high concentration of Nitrogen and low concentration of COD. The flow rate of bCOD from bCOD tank 1066 into anoxic tank 31 is determined by anoxic tank bCOD addition flow rate supervisory control scheme 1035, discussed below. In embodiments in which a stand alone anoxic tank 31 is not present, the bCOD from bCOD tank 1066 will be added to aerobic tank 32.

FIG. 4b shows an embodiment in which anoxic tank 31 is not present, in which aerobic tank 32 has both an anoxic zone and an aerobic zone, which act as both anoxic tank 31 and aerobic tank 32.

The bioprocess operation in the anoxic tank 31 and aerobic tank 32 of MBR 30 is modeled by Activated Sludge Model No. 1 (ASM1), as proposed by Metcalf and Eddy in 2002. However, the ASM1 model has been extended to include the calculation of Mixed Liquor Suspended Solids (MLSS), oxygen mass transfer, dissolved oxygen (DO) concentration, inorganic carbon balance for alkalinity, and pH calculation.

The bioprocess operation model for MBR 30, which is duplicated for the individual anoxic tank 31 and aerobic tank 32, is given as:

Particulate Inert (mg$COD$/l): $\frac{dI}{dt} = [Q*(I_{in} - I)]/V$  Eq 14

Slowly *degr. Sustr.* (mg$COD$/l):

$$\frac{dX_S}{dt} = [Q*(X_{S,in} - X_S) + R_{X_S}*V]/V$$

Hetrorophic biomass (mg$COD$/l): $\frac{dX_{bh}}{dt} =$ $$[Q*(X_{bh,in} - X_{bh}) + R_{X_{bh}}*V]/V$$

Autotrophic biomass (mg$COD$/l): $\frac{dX_{ba}}{dt} =$ $$[Q*(X_{ba,in} - X_{ba}) + R_{X_{ba}}*V]/V$$

Decayed biomass (mg$COD$/l): $\frac{dX_d}{dt} =$ $$[Q*(X_{d,in} - X_d) + R_{X_d}*V]/V$$

Soluble Inert (mg$COD$/l): $\frac{dS_I}{dt} = [Q*(S_{I,in} - S_I)]/V$

Soluble readily *degr. Substr.* (mg$COD$/l):

$$\frac{dS_S}{dt} = [Q*(S_{S,in} - S_S) + R_{S_S}*V]/V$$

Dissolved oxygen (mg/l): $\frac{dS_O}{dt} = [Q*(S_{O,in} - S_O) + K_{la}*$ $$V*(S_{O,sat} - S_O) + V*R_O]/V$$

Dissolved nitrate-N (mg/l): $\frac{dS_{NO}}{dt} = [Q*(S_{NO,in} - S_{NO}) +$ $$R_{S_{NO}}*V]/V$$

Dissolved ammonia-N (mg/l): $\frac{dS_{NH}}{dt} = [Q*(S_{NH,in} - S_{NH}) +$ $$R_{S_{NH}}*V]/V$$

Soluble *bio-degr.* N (mg/l): $\frac{dS_{NS}}{dt} = [Q*(S_{NS,in} - S_{NS}) +$ $$R_{S_{NS}}*V]/V$$

Particulate *bio-degr.* N (mg/l): $\frac{dX_{NS}}{dt} = [Q*(X_{NS,in} - X_{NS}) +$ $$R_{X_{NS}}*V]/V$$

Bicarb alkalinity (mmol/l): $\frac{dS_{alk}}{dt} = [Q*(S_{alk,in} - alk) +$ $$R_{alk}*V]/V$$

ASM1 only includes organic COD (classified as biodegradable or non-biodegradable/inert/refractory, as well as particulate/insoluble and soluble). The particulate COD is included in the MLVSS calculation along with the biomass concentration. However, total MLSS also includes particulate inorganic matter from the feed—to accommodate this, the particulate inorganic matter is also included as a separate state with a simple accumulation based on inlet and outlet and no reaction. The bioprocess model includes the following reactions:

R1 - Aerobic growth of heterotrophy: $SBOD + O_2 \xrightarrow{X_{bh}}$  Eq 15

$$X_{bh} + CO_2$$

R2 - Anoxic growth of heterotrophy: $SBOD + NO_{32} \xrightarrow{X_{bh}}$ $$X_{bh} + N_2 \text{ (De-nitrification)}$$

R3 - Aerobic growth of autotroph: $O_2 + NH_3 + \text{(light)} \xrightarrow{X_{ba}}$ $$X_{ba} + NO_3 \text{ (Nitrification)}$$

R4 - Decay of heterotrophy: $X_{bh} \rightarrow$ $$\text{Debris}(X_d) + InsBOD(X_S) + InsOrgN(X_{NS})$$

-continued

R5 - Decay of autotroph: $X_{ba} \rightarrow$ $$\text{Debris}(X_d) + \text{InsBOD}(X_S) + \text{InsOrgN}(X_{NS})$$

R6 - Ammonification of sol. Org. N: $\text{SolOrgN} \xrightarrow{X_{bh}} NH_3$

R7 - Hydrolysis of organics: $\text{InsBOD} \xrightarrow{X_{bh}} \text{SBOD}$

R8 - Hydrolysis of organic N: $\text{InsOrgN} \xrightarrow{X_{bh}} \text{SolOrgN}$ The reaction rates for these reactions are given by:

Aerobic growth of heterotroph: $R_1 =$   Eq 16
$$\alpha * \mu_H * (S_S/(K_S + S_S)) * (S_O/(K_{OH} + S_O)) * X_{bh}$$
Anoxic growth of heterotroph: $R_2 = (1 - \alpha) * \mu_H * (S_S/(K_S + S_S)) *$
$$(K_{OH}/(K_{OH} + S_O)) * (S_{NO}/(S_{NO} + K_{NO})) * \eta_g * X_{bh}$$
Aerobic growth of autotroph: $R_3 =$
$$\mu_A * (S_{NH}/(S_{NH} + K_{NH})) * (S_O/(K_{OH} + S_O)) * X_{ba}$$
Decay of heterotroph: $R_4 = b_H * X_{bh}$
Decay of autotroph: $R_5 = b_A * X_{ba}$
Ammonification of sol. Org. N: $R_6 = k_a * S_{NS} * X_{bh}$
Hydrolysis of organics: $R_7 =$
$$k_h \{(X_S/X_{bh})/[k_X + (X_S/X_{bh})]\} * X_{bh} \{[S_O/(K_{OH} + S_O)] +$$
$$\eta_h [K_{OH}/(K_{OH} + S_O)] * [S_{NO}/(K_{NO} + S_{NO})]\}$$
Hydrolysis of organic N: $R_8 = R_7 * X_{NS}/(X_S + 10^{-10})$
     ($10^{-10}$ included to avoid divide by zero)

Net generation of slowly degr. Particulate: $R_{XS} =$   Eq 17
$$R_4(1 - f_p) + R_5(1 - f_p) - R_7$$
Net Growth rate of hetrotroph: $R_{X_{bh}} = R_1 + R_2 - R_4$
Net Growth rate of autotroph: $R_{X_{ba}} = R_3 - R_5$
Generation of soluble readily degr. substr: $R_{S_S} = -$
$$\frac{(R_1 - R_2)}{Y_h} + R_7$$
Consumption rate of oxygen: $R_O = -(1 - Y_h) * \frac{R_1}{Y_h} -$
$$(4.57 - Y_a) * \frac{R_3}{Y_a}$$
Net generation of nitrate-N: $R_{S_{NO}} = -R_2 \left[\frac{(1 - Y_h)}{(2.86 * Y_h)}\right] + \frac{R_3}{Y_a}$
Net generation of ammonia-N: $R_{S_{NH}} = -ixbn(R_1 + R_2) -$
$$R_3 \left(ixbn + \frac{1}{Y_a}\right) + R_6$$
Net generation of soluble organic N: $R_{S_{NS}} = -R_6 + R_8$
Net generation of particulate organic N: $R_{X_{NS}} =$
$$(ixbn - f_p * ixun) * (R_4 + R_5) - R_8$$
Net generation of bicarbonate alkalinity: $R_{alk} =$
$$\left(-ixbn * \frac{R_1}{14}\right) + R_2 \left\{[(1 - Y_h)/(14 * 2.86 * Y_h)] - \left(\frac{ixbn}{14}\right)\right\} -$$
$$R_3 \left[\frac{ixbn}{14} + \frac{1}{(7Y_a)}\right] + \frac{R_6}{14}$$
Generation of debris from biomass decay: $R_{X_d} = f_p(R_4 + R_5)$
Generation of $CO_2$ (mol/m³/d): $R_{CO_2} =$
$$(R_1 + R_2) * \left(\frac{IC_{S_S}}{Y_h} - IC_{X_B}\right) - R_3 IC_{X_B} + (R_4 + R_5) *$$
$$[IC_{X_B} - f_p IC_{X_I} - (1 - f_p) IC_{X_S}] + R_7(IC_{S_S} - IC_{X_S})$$

In addition to the above bioprocess model, additional equations were included to model the oxygen mass transfer, alkalinity and pH.

Estimating dissolved oxygen requires the air flow rate, saturated oxygen concentration, and oxygen mass transfer coefficient. Subsequently, the model estimates dependency of all these parameters for different temperature and MLSS. The saturation oxygen concentration is a function of temperature. The estimated oxygen mass transfer coefficient includes temperature correction, MLSS correction, factors due to diffuser density and the air velocity and is given by:

$$K_l a = (1.024^{T-20}) D\alpha (U)^{k_4} \quad \text{Eq 18}$$

where $$U = \frac{Q_{air}}{A},$$

$Q_{air}$ is the flow rate of air in m³/day and A is the cross sectional area of the bioreactor. The exponential dependence on U is captured with $k_4 = 0.8198$. For the oxygen mass transfer, the mixed liquor solids concentration offers resistance and hence reduces the effective mass transfer by the factor $\alpha = e^{-k_3(MLSS)}$ where $k_3 = 0.0771$. Finally, D denotes a correction factor depending on diffuser density. The model uses diffuser density of 2 to 35%. For a diffuser density of 2% and temperature of 25° C., the above figure shows relation between superficial velocity and mass transfer coefficient. The correction factor due to diffuser density is given by:

$$D = k_1(DD)^{0.25} + k_2$$

where $k_1 = 2.5656$, $k_2 = 0.0432$ and DD denotes the diffuser density.

The pH in the aerobic and anoxic tanks 32 and 31 also has to be calculated since it is an operation parameter for monitoring and control. This is done similar to the AD model, by including a dynamic balance on the total dissolved inorganic carbon (IC) and calculation of pH from bicarbonate equilibrium relationship, since the MBR 30 is typically operated at close to pH 7.

More specifically, a dynamic balance for total IC (bicarbonate+dissolved $CO_2$) is given as:

$$\frac{d(S_{IC})}{dt} = Q(S_{IC,in} - S_{IC}) + R_{CO_2} - \frac{R_{CO_2,stripping}}{V} \quad \text{Eq 19}$$

where $S_{IC}$ denotes the molar concentration of inorganic carbon in the water, $R_{CO_2}$ denotes the specific reaction rate for generation of $CO_2$, and $R_{CO_2,stripping}$ denotes the molar rate of removal of $CO_2$ from the liquid phase to the gas phase. The model already includes a balance for bicarbonate alkalinity, denoted as $S_{alk}$, which allows a calculation of the dissolved $CO_2$ concentration as $S_{CO_2} = S_{IC} - S_b$. Thereafter, the pH in the aerobic reactor is calculated from the bicarbonate equilibrium relationship as:

$$pH = -\log_{10}(S_H) = \log_{10}(K_a) + \log_{10}(S_{alk}) - \log_{10}(S_{CO_2}) \quad \text{Eq 20}$$

The $CO_2$ removal rate from liquid to gas phase, $R_{CO_2,stripping}$, is calculated in the aerobic tank 32 by using the Henry relationship for gas-liquid equilibrium, and a mass balance on $CO_2$ between the incoming and exhaust air. In the anoxic tank 31, it is calculated by using a mass transfer relation.

Finally, the bioprocess model in the aerobic tank 32 and anoxic tank 31 was coupled with a static separation model in the membrane tank 33, ignoring the relatively faster dynamics due to the much lower holdup volume compared to the aerobic/anoxic tanks 32 and 31.

As can be seen, anoxic tank 31 and aerobic tank 32 are modeled separately in dynamic MBR model 360, which serves as the basis for offline dynamic MBR model 361 online dynamic MBR model 362. Accordingly, anoxic tank 31 and aerobic tank 32 are modeled separately in offline dynamic MBR model 361 and online dynamic MBR model 362.

While the discussion of the MBR model above has been directed to the bioprocess operation, another critical aspect is the membrane fouling—which has a direct impact on operation costs in terms of aeration for scouring and chemicals for cleaning. Motivated by this, a data-based empirical model was sought using plant operation data to describe changes in permeability of the membrane in membrane tank 33 over time as a function of upstream bioprocess and membrane tank operation parameters.

Figure 5:
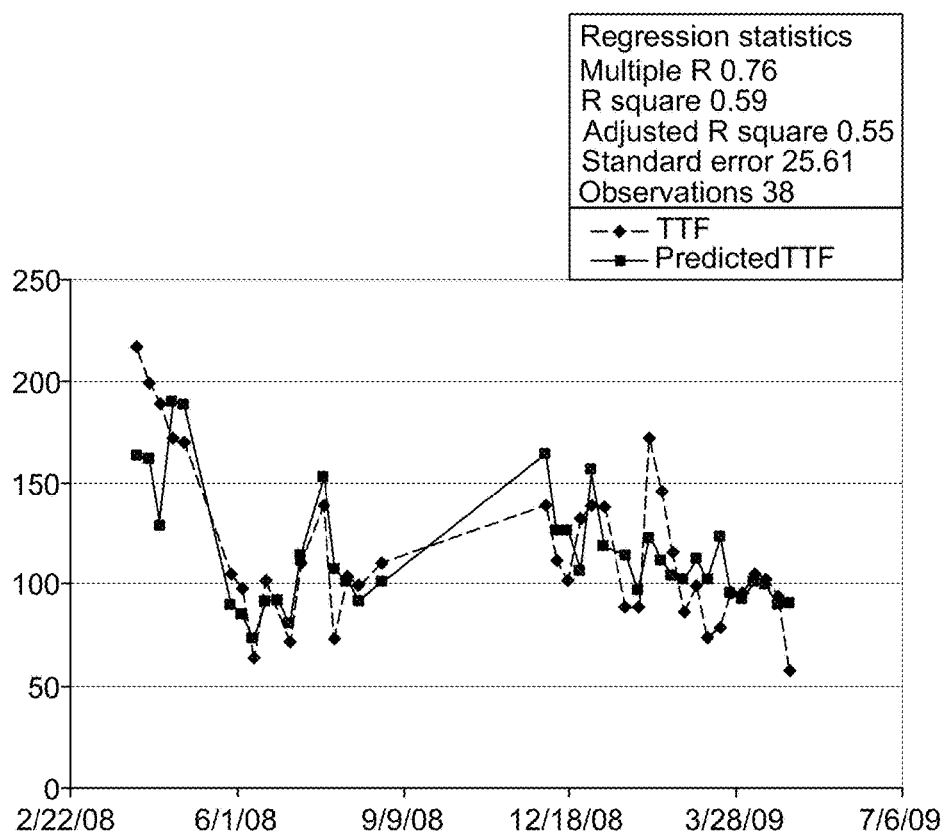
FIG. 5 is a plot of TTF variation with time.

Data analysis for membrane fouling or permeability has been conducted using plant operation data. In one case, standardized time-to-filter (TTF) data was available, which is indicative of the filterability of the sludge and is directly related to the inverse of the membrane permeability. FIG. 5 shows a comparison of measured TTF and predicted (estimated) TTF obtained for an embodiment of MBR 30 by fitting a correlation for TTF variation with respect to available parameters measured in the MBR operation. FIG. 5, is a plot of TTF vs. time.

Preliminary data regression analysis indicated that for this account, there are three factors that have a large impact membrane permeability. They are system temperature, reactor MLSS, and % Total Kejeldahl Nitrogen (TKN) removal. The empirical correlation identified for the embodiment of MBR 30 was TTF=240.6+0.008*ReactorMLSS+818*(1−TKN %)−2.57*Temp (F), $R^2$=60%.

|  | Coefficient | Standard Error | t Stat | P-value |
| --- | --- | --- | --- | --- |
| Intercept | 240.6 | 78.0 | 3.085 | 0.004 |
| Reactor MLSS | 0.0 | 0.0 | 2.051 | 0.048 |
| 1-TKN % | 817.6 | 126.6 | 6.457 | 0.000 |
| Temp | −2.6 | 1.0 | −2.514 | 0.017 |

The coefficients identified are all statistically significant (i.e. p-value<0.05). The higher the reactor MLSS and the lower % TKN removal and system water temperature, the higher the TTF, therefore, the lower the membrane permeability. The impacts of reactor MLSS and system water temperature on membrane permeability are as expected. The rate-limiting step in the reactor is autotrophic reaction, and % TKN removal is an indication of how autotrophic bacteria perform in the reactor. A lower % TKN removal indicates likelihood that the autotrophic bacteria are stressed, which may secrete exocellular biopolymer to protect themselves and lead to decreasing sludge filterability. Moreover, the absolute TKN removal is also strongly correlated to MLVSS/(SRT/HRT) in the following empirical correlation identified for the embodiment of MBR 30: MLVSS/(SRT/HRT)=111.1+16.5*(TKN_in−TKN_out).

|  | Coefficient | Standard Error | t Stat | P-value |
| --- | --- | --- | --- | --- |
| Intercept | 111.11 | 210.6 | 0.528 | 0.600 |
| TKN_in − TKN_out | 16.5 | 5.8 | 2.825 | 0.007 |

In the above embodiment of MBR 30, SRT/HRT is approximated by (MLSS-MLVSS)/TSS_in with the assumption that influent VSS/TSS ratio is constant. The fact that it is statistically significant that TKN removal variation relates well with both membrane permeability variation and MLVSS variation highlights the need for TKN monitoring and its control (by SRT, HRT) to reduce system TKN variation, and therefore its impact on membrane performance.

In another embodiment of MBR 30, very detailed operation data was recorded over a long period of several months. This data, along with variation in the membrane permeability was analyzed to identify the correlation between the two. A key challenge in this analysis is that several of the variables that are used as factors for predicting the permeability, are themselves highly correlated (e.g. dissolved oxygen and blower rates, pH and alkalinity etc.). Partial least squares (PLS) is an advanced multivariate statistical analysis tool that works very well with these challenges. A dynamic first-order model was postulated to describe the slow variation in membrane permeability over several months of operation. To this end, all the recorded variables were also averaged to get daily average data—any faster variation is not important to predict long-term variation in permeability.

Figure 6:
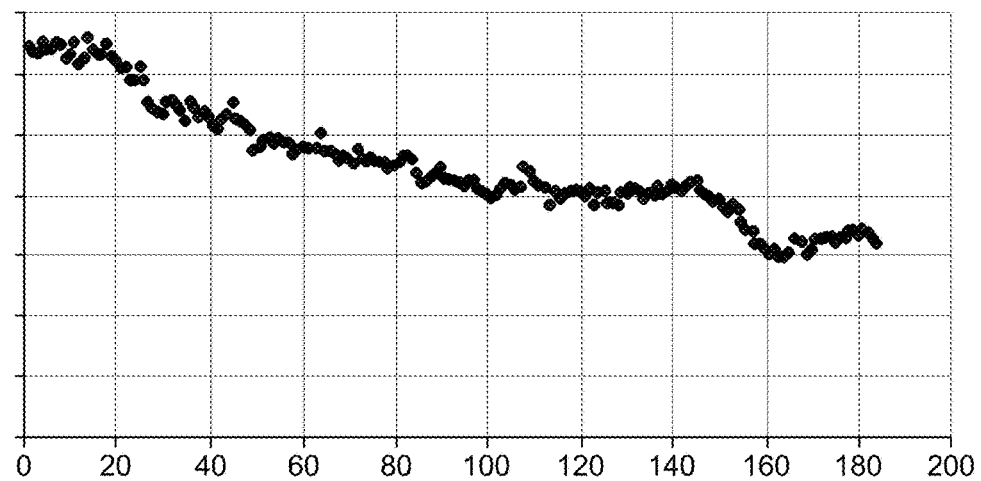
FIG. 6 is a plot of membrane permeability variation with time.

FIG. 6, a plot of membrane permeability vs. time, clearly shows non-stationary behavior of permeability. Hence, it was modeled as a first order system by augmenting lagged output vector with the other inputs. Thus if $Y_k$ represents the permeability/response vector, the corresponding predictor block is constructed as $Z_k[Y_{k-1}\ X_{k-1}]$, where $X_{k-1}$ denote the extensive set of recorded variables for bioprocess and influent conditions.

PLS was used to fit a first-order dynamic model mentioned above. It was observed that a single loading vector (the dominant combination of all predictor variables that is most correlated with the output) explains a significant portion of the output variation. Analysis of this first loading vector revealed the relative importance of the variables obtained from the PLS model, which is based on their predictive ability, as shown in FIG. 7-Dominant variables and their relative contribution to variation in permeability.

Figure 7:
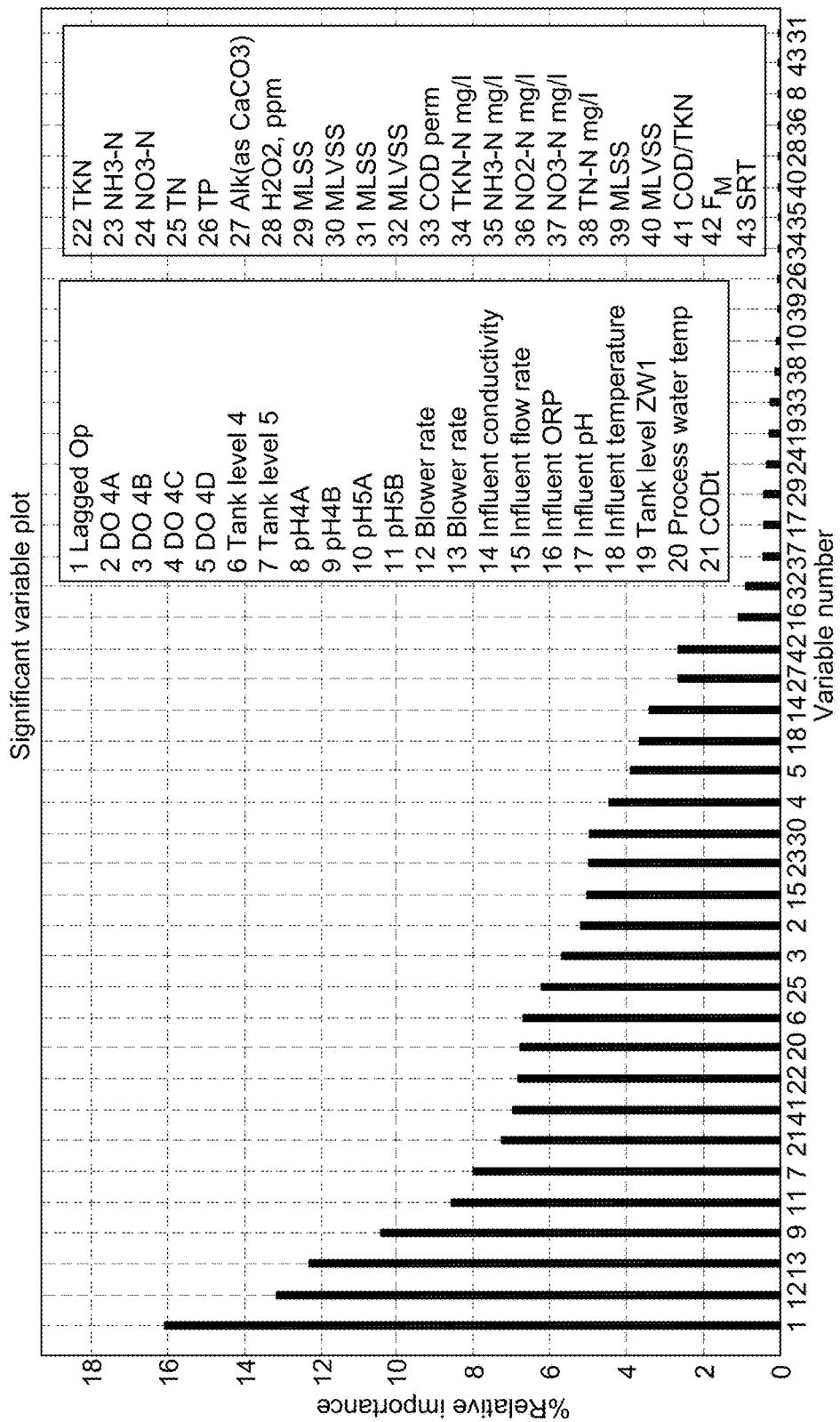
FIG. 7 is a plot of the dominant variables in PLS and their relative contribution to variations in permeability.

It can be seen in FIG. 7 that if the lagged output ($Y_{k-1}$) is ignored, the other influential variables are Blower rate, pH, Tank level, COD/TKN ratio, process water temperature, TKN, TN, DO, Conductivity and Alkalinity. The figure shows ability of the PLS model to pick-up the same variables measured at different locations (tanks) For instance, 12 and 13th variables both refer to the blower rate, which are identified as the two variables having maximum impact on the fouling rate. It could be seen that contribution of other variables drop from 12.6% predictive power to less than 2%, the latter of which is used as a cut-off threshold.

Figure 8:
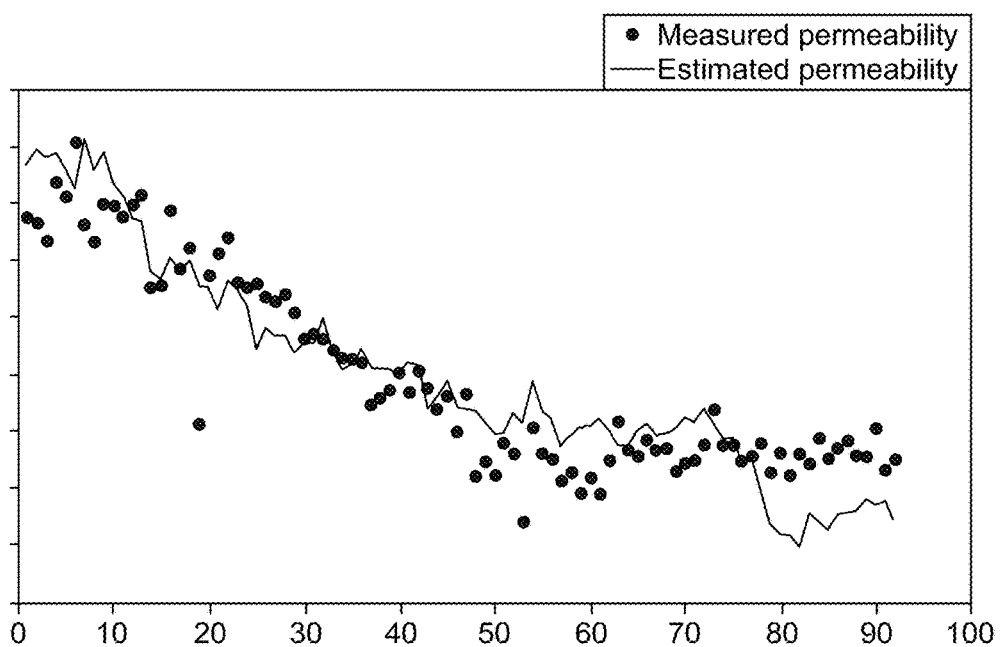
FIG. 8 is a plot of the cross validation of membrane permeability for PLS.

Using the alternate samples in dynamic data block for model building, the remaining section of the data was used for validation. It can be seen in FIG. 8 that the derived dynamic model can predict the permeability data quite satisfactorily.

The developed dynamic models of the AD 20 and MBR 30 are used as the basis for a method of operating AD 20 and MBR 30 through online monitoring and control of one or both of AD 20 and MBR 30 of wastewater treatment plant 10.

Figure 9:
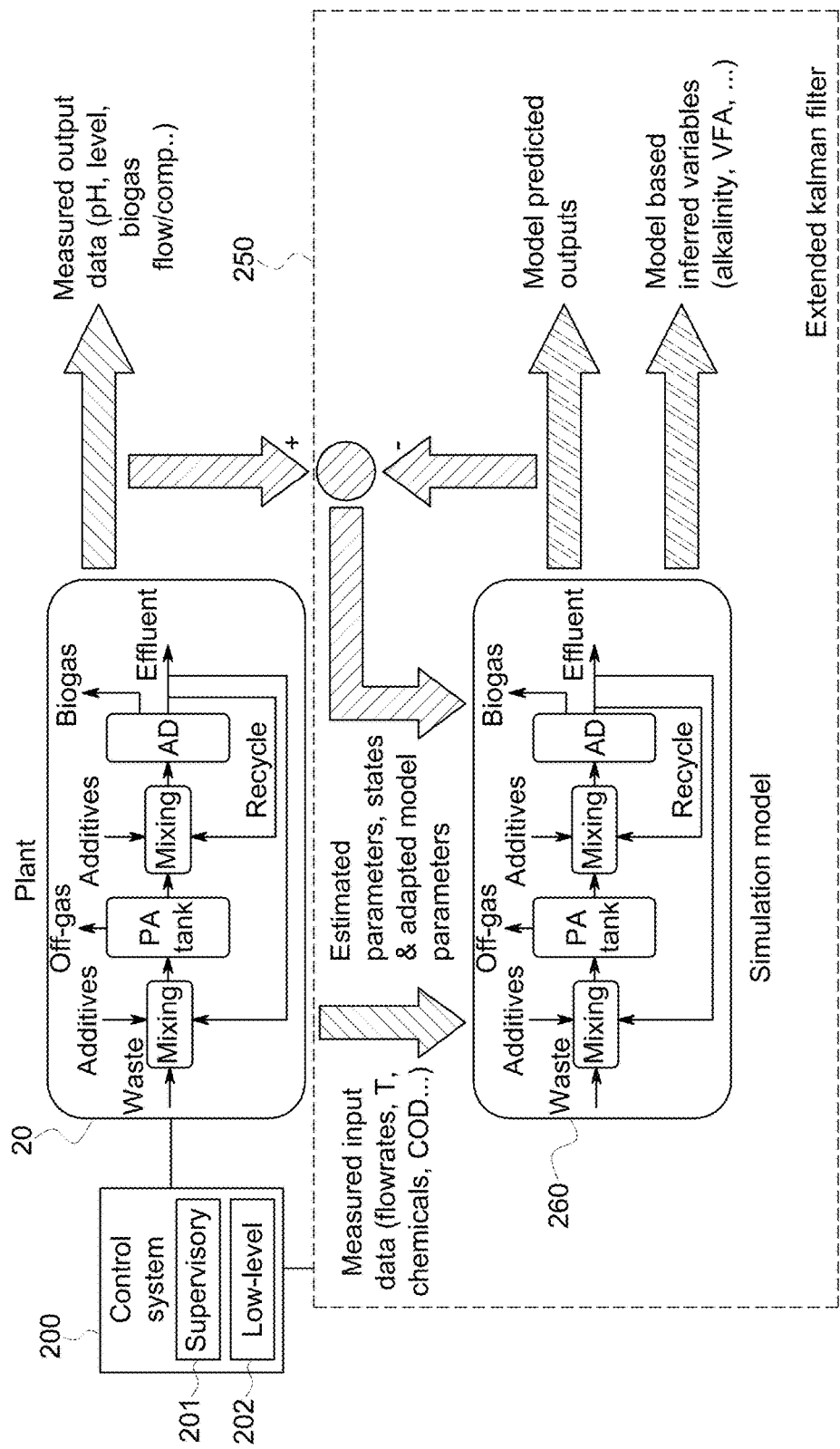
FIG. 9 is a block diagram of the overall architecture for an AD having an extended Kalman filter (EKF) and a control system in accordance with aspects of the present technique.

More specifically, for online monitoring of the AD 20, a set of online sensors are used along with model-based estimation of variables not measured directly through the use of a constrained Extended Kalman Filter. FIG. 9 shows the overall architecture for monitoring an embodiment of AD 20 with control system 200, using a combination of online sensors that measure the measured input data and measured output data of AD 20. An extended Kalman filter 250 containing the dynamic model 260 of AD 20 discussed above uses the measured input data and measured output data of AD 20 to estimate the following items: estimated parameters, states, adapted model parameters, model predicted (estimated) outputs, and model based inferred variables. AD control system 200 interfaces with AD extended Kalman filter 250 and has a supervisory control system 201 and a low level control system 202.

The comparison of the estimated and actual values of the measured output data, offline laboratory testing data and estimated values of model predicted outputs and model based inferred variables by extended Kalman filter 350 estimate values for the estimated parameters, states, and adapted model parameters of dynamic model 360 of MBR 30.

Further extended Kalman filter 250 containing the dynamic model 260 of AD 20 discussed above uses the measured input data and measured output data of AD 20 to calculate model predicted outputs and model based inferred variables (also sometimes called virtual sensors). A similar architecture is used for the MBR 30 as well. Extended Kalman Filter (EKF) is a standard online model-based estimation algorithm to estimate unknown variables (states, parameters) in the model and match the model outputs to measured variables from online sensors.

Below are exemplary lists of measured output data, measured input data, estimated parameters, adapted model parameters, model predicted outputs, and model based inferred variables for AD 20 of WWTP 10. AD 20 has an AD control system 200, AD online EKF 251, and AD offline EKF 252.

| Estimated Parameters and Adapted Model Parameters | Updated By Online EKF (Adapted Model Parameters) | Estimated By Offline EKF (Estimated Parameters) |
| --- | --- | --- |
| PA Reactor Composite Fraction of Carbohydrate | X | X |
| PA Reactor Composite Fraction of Fat | X | X |
| PA Reactor Composite Fraction of Protein | X | X |
| PA Reactor Fraction of Insoluble Convertible to SBOD | X | X |
| PA Reactor Acedogenthese Reaction Coefficient | X | X |
| PA Reactor Biomass Decay Rate | | X |
| PA Reactor Insoluble Hydrolysis Reaction Coefficient | | X |
| PA Reactor Insoluble Flow out Coefficient | X | X |
| PA Reactor CO2 Escape Coefficient | | X |
| AD Reactor Composite Fraction of Carbohydrate | X | X |
| AD Reactor Composite Fraction of Fat | X | X |
| AD Reactor Composite Fraction of Protein | X | X |
| AD Reactor Fraction of Insoluble Convertible to SBOD | X | X |
| AD Reactor Acedogenthese Reaction Coefficient | | X |
| AD Reactor Acetogenesis Reaction Coefficient | | X |
| AD Reactor Acetoclastic Methanogenesis Reaction Coefficient | X | X |
| AD Reactor Hydrogen Methanogenesis Reaction Coefficient | | X |
| AD Reactor Biomass Decay Rate | | X |
| PA Reactor Insoluble Hydrolysis Reaction Coefficient | | X |
| PA Reactor Insoluble Flow out Coefficient | X | X |

| Model Based Inferred Variables | |
| --- | --- |
| Outputs | Inputs |
| PA Reactor Alkalinity | Raw Influent Insoluble COD |
| PA Reactor VFA | Raw Influent Insoluble Inert COD |
| PA Reactor Temperature | Raw Influent Soluble Inert COD |
| PA Reactor SCOD | Raw Influent SBOD Saccharide |
| PA Reactor TCOD | Raw Influent SBOD LCFA |
| PA Reactor SBOD | Raw Influent SBOD Amino Acid |
| AD Reactor Alkalinity | Raw Influent Propionate Acid |
| AD Reactor VFA | Raw Influent Acetate Acid |
| AD Reactor Temperature | Raw Influent Inorganic Carbon Content |
| AD Reactor SCOD | Raw Influent Alkalinity |
| AD Reactor SBOD | Raw Influent Inorganic Nitrogen |
| AD Reactor Acedogenthese Biomass | Raw Influent SCOD |
| AD Reactor Acetogenesis Biomass | Raw Influent TCOD |
| AD Reactor Acetoclastic Methanogenesis Biomass | Raw Influent SBOD |
| AD Reactor Hydrogen Methanogenesis Biomass | |
| AD Reactor Insoluble COD | |
| AD Reactor Insoluble Inert COD | |
| AD Reactor Soluble Inert COD | |
| AD Reactor SBOD Saccharide | |
| AD Reactor SBOD LCFA | |
| AD Reactor SBOD Amino Acid | |
| AD Reactor Propionate Acid | |
| AD Reactor Acetate Acid | |
| AD Reactor Inorganic Carbon Content | |
| AD Reactor Alkalinity | |
| AD Reactor Inorganic Nitrogen | |
| AD Reactor SCOD | |
| AD Reactor TCOD | |
| AD Reactor SBOD | |
| SCOD Conversion Rate | |
| CH4 Conversion Efficiency | |
| Recycle Flow Rate | |

| Measured Input Data | Online | Offline |
| --- | --- | --- |
| Raw Influent pH | X | X |
| Raw Influent Temperature | X | X |
| Raw Influent Flow Rate | X | X |
| Raw Influent TOC | X | X |
| Raw Influent TIC | X | X |
| Added Alkali Flow Rate | X | X |
| PA Reactor Level | X | X |
| AD Feed Flow Rate | X | X |
| Raw Influent SCOD | | X |
| Raw Influent TCOD | | X |
| Raw Influent SBOD | | X |
| Raw Influent VSS | | X |
| Raw Influent TSS | | X |
| Raw Influent Soluble Inorganic Nitrogen | | X |
| Raw Influent VFA | | X |
| Added Alkali concentration | | X |

| Measured Output Data & Model Predicted Outputs | Online | Offline |
| --- | --- | --- |
| PA Reactor pH | X | X |
| PA Effluent TOC | X | X |
| PA Effluent TIC | X | X |
| AD Biogas Flow Rate | X | X |
| AD Biogas CH4 Concentration | X | X |
| AD Biogas CO2 Concentration | X | X |
| AD Reactor pH | X | X |
| AD Effluent TOC | X | X |
| AD Effluent TIC | X | X |

-continued

| Measured Output Data & Model Predicted Outputs | Online | Offline |
|---|---|---|
| AD Effluent VFA | | X |
| AD Effluent Alkalinity | | X |
| AD Reactor MLVSS | | X |
| AD Effluent TCOD | | X |
| AD Effluent SCOD | | X |
| AD Effluent VSS | | X |
| AD Effluent TSS | | X |

It is understood that the lists above of measured output data, measured input data, estimated parameters, adapted model parameters, model predicted outputs, and model based inferred variables are exemplary, can vary from one application to another application, and can be established by a person having ordinary skill in the art based on the person's knowledge of the process and application. Further, it is understood that the adapted model parameters are a subset of the estimated parameters, which are more extensive. Additionally, it is understood that the model based inferred variables include both unmeasured inputs and outputs for AD 20.

Figure 10:
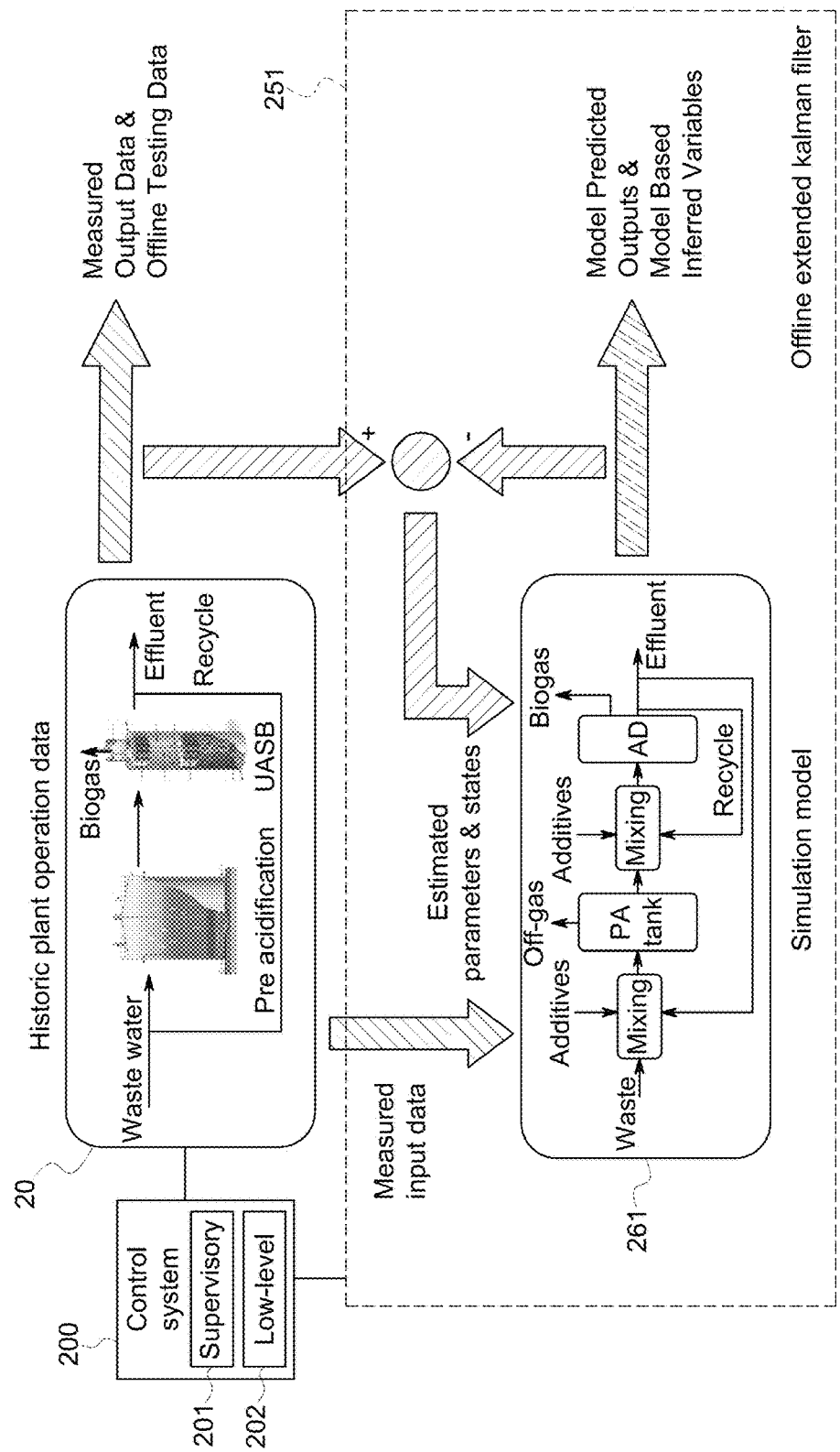
FIG. 10 is a block diagram of the architecture for an AD having an online EKF and a control system in accordance with aspects of the present technique.

More specifically, FIG. 10 shows the overall architecture for the AD offline EKF 251 containing an offline dynamic model 261 of AD 20 for identifying estimated parameters and states of offline dynamic model 261 of an embodiment of AD 20 having control system 200. AD offline EKF 251 identifies the estimated parameters and states of offline dynamic model 261 by using historical measured input data, historical measured output data, and historical offline laboratory testing data for AD 20.

Figure 11:
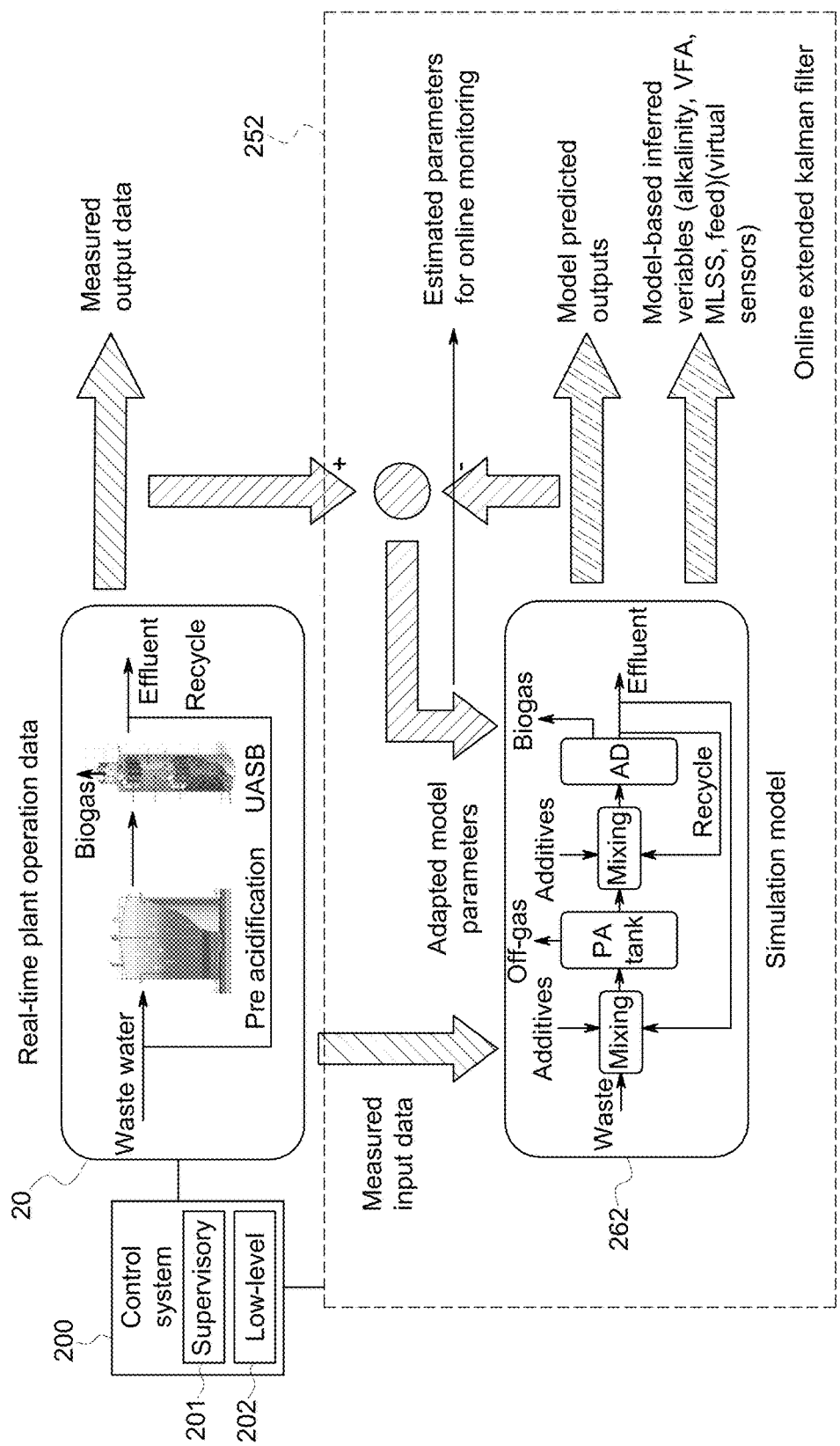
FIG. 11 is a block diagram of the architecture for an AD having an offline EKF and a control system in accordance with aspects of the present technique.

FIG. 11 shows the overall architecture of an AD online EKF 252 containing an online dynamic model 262 of AD 20 for real-time monitoring/virtual sensing/controlling of an embodiment of AD 20 having control system 200. Control system 200 has a supervisory control system 201 and a low level control system 202. AD online EKF 252 calculates model predicted outputs and model based inferred variables for AD 20 and updates the adapted model parameters of the online dynamic model 262 of AD 20 using real time measured output data and real time measured input data for AD 20, and the online dynamic model 262 of AD 20 containing estimated parameters. The adapted model parameters of the online dynamic model 262 of AD 20 are a subset of the estimated parameters that were identified in the offline dynamic model 261 of AD 20 using AD offline EKF 251 as was discussed above.

The raw feed composition listed in the model based inferred variables above can include one or more of carbohydrates, protein, fat, sCOD, insCOD, propionate, acetate, and alkalinity.

Additionally, it is understood that in some embodiments of WWTP 10, if an AD 20 is located upstream of MBR 30, some of the model based inferred variables calculated by online dynamic model 262 of AD 20 located in AD online EKF 252, such as the composition of AD effluent, are provided to MBR 30 by AD online EKF 252, therefore enabling feed forward control of MBR 30 by MBR control system 300 which uses the provided data as inputs. It is understood that the information provided regarding the composition of the effluent includes multiple pieces of information, such as the individual amounts of elements and compounds contained in the effluent (e.g. Nitrogen, Oxygen, etc.).

Additionally, it is understood that in some embodiments of WWTP 10, if an MBR 30 is located upstream of AD 20, some of the model based inferred variables calculated by online dynamic model 362 of MBR 30 located in MBR online EKF 352, such as the composition of MBR effluent, are provided to AD 20 by MBR online EKF 352, therefore enabling feed forward control of AD 20 by AD control system 200 which uses the provided data as inputs. It is understood that the information provided regarding the composition of the effluent includes multiple pieces of information, such as the individual amounts of elements and compounds contained in the effluent (e.g. Nitrogen, Oxygen, etc.).

Further, the states for offline dynamic model 261 of AD offline EKF 251 and online dynamic model 262 of AD online EKF 252, are defined above in equations 3 and 7-10.

Further, it is understood that both offline dynamic model 261 of AD 20 and online dynamic model 262 of AD 20 both contain estimated parameters and adapted model parameters, a subset of the adapted model parameters. Accordingly, the structures of offline dynamic model 261 of AD 20 and online dynamic model 262 of AD 20 are the same. However, all of the estimated parameters are identified by AD offline EKF 251 in offline dynamic model 261 of AD 20. Meanwhile, only the adapted model parameters are identified (updated) in the online dynamic model 262 of AD 20 by AD online EKF 252. Further, it is understood that the offline dynamic model 261 of AD 20 and online dynamic model 262 of AD 20 are based on first principles with physical meanings for the respective estimated parameters and adapted model parameters with unknown values (e.g., the reaction rate kinetic parameter) whose values are estimated by best fitting.

It is understood that the measured input data and measured output data is data obtained from physical sensors of AD 20. Further, model based inferred variables are virtual sensors that have traditionally only been available through periodic offline testing. A model based inferred variable of AD 20 is a "virtual sensed" variable that is estimated by the AD online EKF 252 using the online dynamic model 262 of AD 20, real time measured input data of AD 20, and real time measured output data of AD 20. The model based inferred variables of AD 20 are first developed by the AD online EKF 251 using offline dynamic model 261 of AD 20, historical measured input data of AD 20, historical measured output data of AD 20, and historical offline testing data of AD 20. It is understood that the model based inferred variables include both unmeasured inputs and outputs of AD 20.

A model predicted output is an output of AD 20 that is estimated by the AD offline EKF 251 and AD online EKF 252. The AD offline EKF 251 estimates the model predicted outputs of AD 20 using offline dynamic model 261 of AD 20, historical measured input data of AD 20, historical measured output data of AD 20, and historical offline testing data of AD 20. The AD online EKF 252 estimates the model predicted outputs of AD 20 using the online dynamic model 262 of AD 20, real time measured input data, and real time measured output data. It is understood that each model predicted output of AD 20 corresponds to a measured output of AD 20.

Estimated parameters are parameters that are identified in the offline dynamic model 261 of AD 20 located in AD offline EKF 251, such that for a given historical input data value, the predicted historical output data value or model based inferred variable value matches the corresponding actual historical output data value or actual offline laboratory testing value. The estimated parameters from the offline dynamic model 261 of AD 20 located in AD offline EKF 251 are imported into the online dynamic model 262 of AD 20 located in AD online EKF 252. The adapted model parameters are a subset of the estimated parameters, which are updated in the AD online EKF 252. The AD online EKF 252 is used to generate real time estimated values for the model predicted outputs and model based inferred variables of AD 20.

In one embodiment of a method of monitoring and controlling AD 20, initially an AD offline EKF 251, such as the one shown in FIG. 10, is used to identify estimated parameters (e.g. reaction kinetics) and states for the offline dynamic model 261 of AD 20 to match historical operation data from AD 20. During this offline phase, extensive data, both available historical measured output data, historical measured input data, as well as historical offline lab-analysis data from over a period of operation are used to identify the states and estimated parameters of the offline dynamic model 261 of AD 20. Once the estimated model parameters and states of offline dynamic model 261 of AD 20 are identified, they are imported from offline dynamic model 261 of AD 20 into the online dynamic model 262 of AD 20. The online dynamic model 262 of AD 20 is used in AD online EKF 252, such as the one shown in FIG. 11, for online monitoring, wherein real time measured output data and real time measured input data from AD 20 online sensor data is used to estimate model predicted outputs and model based inferred variables of AD 20. In the online estimation, one unknown is the variation in the feed composition to AD 20, e.g. mix of carbohydrates, fats and proteins, alkalinity, and VFA. The AD online EKF 252 is used to estimate the unknown/varying feed compositions along with any adapted model parameters that are likely to vary frequently and are prudent for monitoring, such as the inhibition of methanogenesis kinetics due to a toxic ingredient in the feed. Once the unknown feed composition is identified correctly, the model based inferred variables (e.g. biomass concentration, alkalinity, VFA, etc.) provides a "virtual" estimate of these unmeasured variables for more complete online monitoring. Traditionally, these model based inferred variables were ascertained via offline laboratory testing and not available in real time through actual real time sensors. Accordingly, AD online EKF 252 provides a real time estimated value for these model based inferred variables.

Figure 12A:
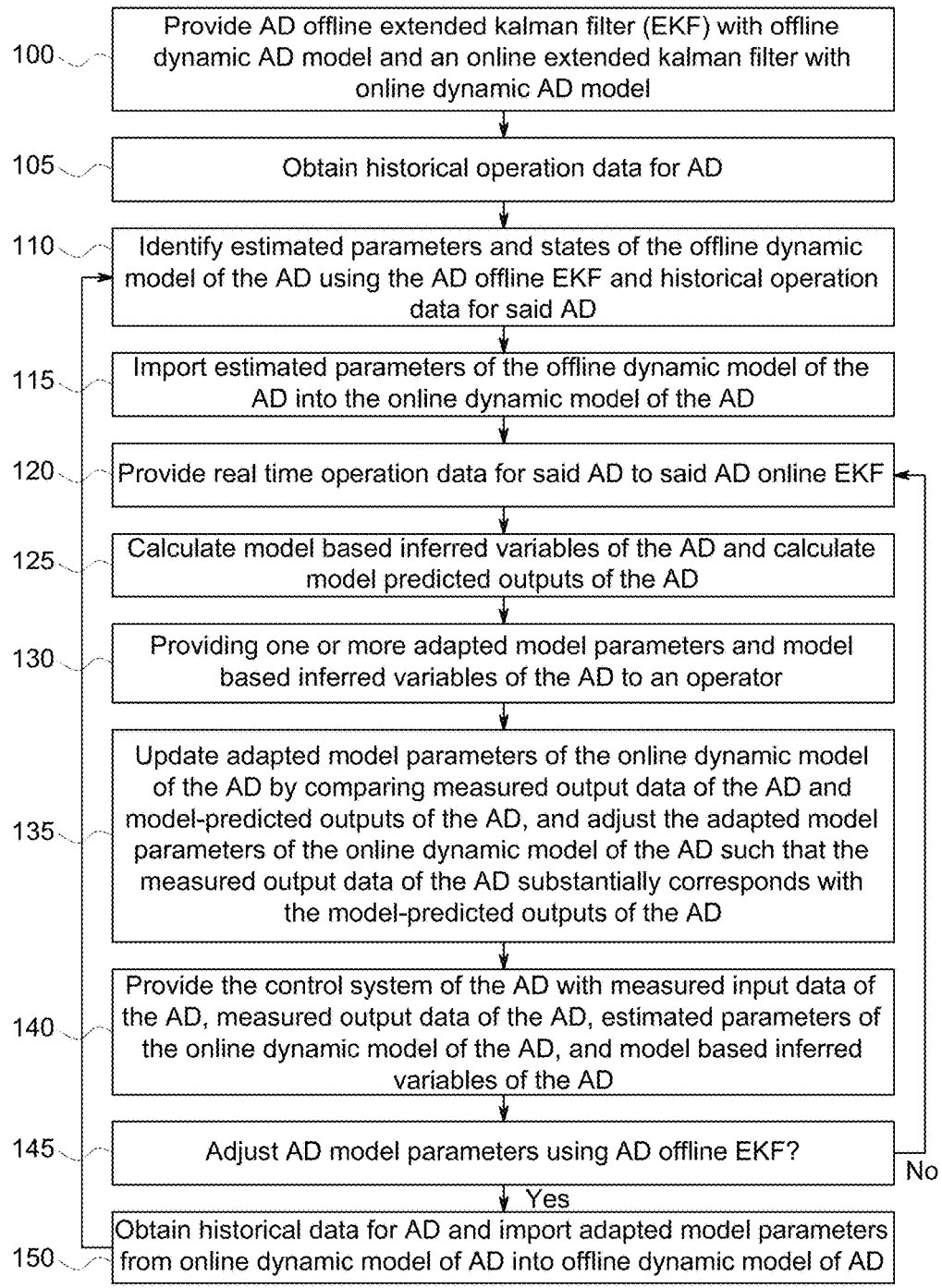
FIG. 12a is a flow chart depicting a method of operating an AD in accordance with aspects of the present technique.

FIG. 12a is a flow chart of a method of operating AD 20 through online monitoring and control of AD 20 using the AD offline and online EKFs 251 and 252 and control system 200. Steps 100-135 and 145-150 are monitoring steps of AD 20 and step 140 is a controlling step of AD 20.

In step 100, the monitoring of AD 20 is commenced by AD offline EKF 251 having an offline dynamic model 261 of AD 20, providing an AD online EKF 252 having an online dynamic model 262 of AD 20. The online and offline dynamic models 261 and 262 of AD 20 have states, process material balances, energy balances and bio-chemical reaction kinetics. The offline dynamic model 251 and online dynamic model 252 of AD 20 have both estimated parameters and adapted model parameters. The adapted model parameters are a subset of the estimated parameters.

The estimated parameters of offline dynamic model 261 of AD 20 and adapted model parameters of online dynamic model 262 of AD 20 are comprised of kinetic parameters and stoichiometric coefficients for reactions of at least one of insoluble organics hydrolysis, acedogenesis, acetogenesis, acetoclastic methanogenesis, hydrogen methanogenesis, and biomass growth.

The material balances in said online and offline dynamic models 261 and 262 of AD 20 are comprised of insoluble organics, soluble substrates, VFA, organic carbon, inorganic carbon and alkalinity. The insoluble organics is comprised of carbohydrates, protein and fat. Further, soluble substrate and VFA include at least one of glucose, LCFA, amino acid, acetate acid, propionate acid and biomass for acedogenesis, acetogenesis, acetoclastic methanogenesis and hydrogen methanogenesis bio-chemical processes. Additionally, organic carbon is comprised of organics and methane from biogas. Further, inorganic carbon is comprised of at least one of carbon dioxide, carbonate and bicarbonate. Additionally, alkalinity is comprised of alkalinity associated with bicarbonate, VFA, added alkali, and generation of ammonia and hydrogen sulfide.

The bio-chemical reaction kinetics in online and offline dynamic models 261 and 262 of AD 20 are comprised of at least one of insoluble organics hydrolysis, acedogenesis, acetogenesis, acetoclastic methanogenesis, hydrogen methanogenesis, and biomass growth.

In some embodiments, limits are applied to one or more of the estimated parameters, adapted model parameters, and states. Further, in some embodiments, constraints are applied to one or more of the model-predicted outputs and model based inferred variables. These limits and constraints can be lower and upper limits specified by a person having ordinary skill in the art based on the person's knowledge of the process and application.

In step 105, historical operation data for AD 20 is obtained. The historical operation data includes measured input data, measured output data, and laboratory analysis data. More specifically, historical operation data of AD 20 may include at least one of liquid flow rates, gas flow rates, biogas compositions, TOC in liquid streams, TIC in liquid streams, AD pH, and ammonia in AD effluent. Further, biogas compositions include one or more of methane, carbon dioxide, and hydrogen sulfide In step 110, estimated parameters and states of the offline dynamic model 261 of AD 20 are identified using the AD offline EKF 251 and the historical operation data for AD 20. At least one of the estimated parameters of offline dynamic model 261 of AD 20 is estimated with confidence intervals, which are the estimated variances corresponding to the estimated parameters of offline dynamic model 261 of AD 20. Stated alternatively, the confidence intervals are determined by their corresponding variances, normally assumed as Normal distribution, therefore 95% confidence intervals are approximate four times of the standard deviations.

The estimated parameters of the offline dynamic model 261 are identified by AD offline EKF 251 simulating one time step of the historical operation data for AD 20 to update values for the estimated parameters, model predicted outputs, states, and covariance estimates and develop model based inferred variables. In one embodiment, a dynamic nonlinear model of AD 20 and measured input data are used to simulate and update the estimated parameters, model predicted outputs, states, and model based inferred variables. A linearized dynamic model of AD 20 is used to simulate and update the covariance estimate.

Once estimated, the values for the model predicted outputs and model based inferred variables are compared to the actual historical values, if available. Based on the comparison, the model predicted outputs, model based inferred variables, and covariance values are adjusted, if necessary for the estimated values to agree with the actual values. AD offline EKF 251 then simulates the next historical data time step.

The method progresses to step 115 once AD offline EKF 251 simulates all of the historical data time steps or a user intervenes.

In step 115, the estimated parameters of the offline dynamic model 261 of said AD 20 are imported into the online dynamic model 262 of AD 20.

In step 120, real time operation data for AD 20 is provided to AD online EKF 252. The real time operation data is comprised of measured input data and measured output data of AD 20. More specifically, real time operation data of AD 20 may include at least one of liquid flow rates, gas flow rates, biogas compositions, TOC in liquid streams, TIC in liquid streams, AD pH, and ammonia in AD effluent. Further, biogas compositions include one or more of methane, carbon dioxide, and hydrogen sulfide In step 125, model based inferred variables of AD 20 are updated using AD online EKF 252, the online dynamic model 262 of AD 20, measured input data of AD 20, and measured output data of AD 20. Optionally, in step 125, model predicted outputs are calculated using AD online EKF 252, the online dynamic model 262 of AD 20, measured input data of AD 20, and measured output data of AD 20. At least one of the model based inferred variables of online dynamic model 262 of AD 20 is estimated with confidence intervals, which are the estimated variances corresponding to the model based inferred variables of online dynamic model 262 of AD 20. Stated alternatively, the confidence intervals are determined by their corresponding variances, normally assumed as Normal distribution, therefore 95% confidence intervals are approximate four times of the standard deviations. The model based inferred variables of online dynamic model 262 of AD 20 are comprised of at least one of feed composition, biomass activity, and biomass concentration.

In step 130, one or more adapted model parameters and model based inferred variables of AD 20 are provided to an operator of AD 20. It is understood that offline laboratory testing providing results corresponding to some of the model based inferred variables of AD 20 will still take place and be recorded for use as historical operation data for tuning purposes, and provided to the operator.

In step 135, the adapted model parameters of the online dynamic model 262 of AD 20 are tuned by comparing the measured output data of AD 20 and model predicted outputs of AD 20, and adjusting the adapted model parameters of the online dynamic model 262 of AD 20, such that the measured output data of AD 20 substantially corresponds with the model predicted outputs of AD 20. It is contemplated that in some embodiments, the adapted model parameters of online dynamic model 262 of AD 20 can be further turned using different weights for online measurements and prior knowledge of measurement accuracy.

In step 140, control system 200 is provided with measured input data of AD 20, measured output data of AD 20, estimated parameters of online dynamic model 262 of the AD 20, adapted model parameters of online dynamic model 262 of the AD 20, and model based inferred variables of AD 20 to control at least one of a nutritional additive concentration of AD reactor 24, a nutritional additive concentration of PA reactor 22, pH of AD reactor 24, pH of PA reactor 22, biomass concentration of AD reactor 24, fluid level of said PA reactor 22, and a recycle flow rate of said AD 20.

Control system 200 has an AD supervisory control system 201 and an AD low level control system 202. AD supervisory control system 201 is comprised of at least one of an AD reactor pH supervisory controller 700, a PA reactor pH supervisory controller 701, and an PA:AD overall recycle flow ratio supervisory controller 720.

AD reactor pH supervisory controller 700 is comprised of an AD reactor nonlinear PI pH controller 705 and an AD reactor P alkalinity controller 710 in a cascaded configuration. PA reactor pH supervisory controller 701 is comprised of a PA reactor nonlinear PI pH controller 706 and a PA reactor P alkalinity controller 711 in a cascaded configuration. PA:AD overall recycle flow ratio supervisory controller 720 is comprised of a PA:AD recycle ratio controller 725 and a PA reactor and AD reactor recycle flow rate controller 730.

AD low-level control system 202 is comprised of at least one of an AD reactor biomass concentration controller 735, a PA reactor fluid level controller 737, a PA reactor nutritional additive concentration controller 51, and an AD reactor nutritional additive concentration controller 61.

In step 145, normally the method progresses to step 120 for the next time point operation. However, if the adapted model parameters of online dynamic model 262 of AD 20 need to be adjusted after operating for a period of time (e.g. reporting incorrect or inconsistent values for model predicted outputs and model based inferred variables), historical data for AD 20 is obtained and the method returns to step 110. Optionally, in some embodiments of step 145, the adapted model parameters are imported from online dynamic model 262 of AD 20 into offline dynamic model 261 of AD 20 before the method returns to step 110. This importing of the adapted model parameters from online dynamic model 262 of AD 20 into offline dynamic model 261 of AD 20 helps the estimated parameters converge faster when they are re-identified in the offline dynamic model 261 using AD offline EKF 251.

Figure 12B:
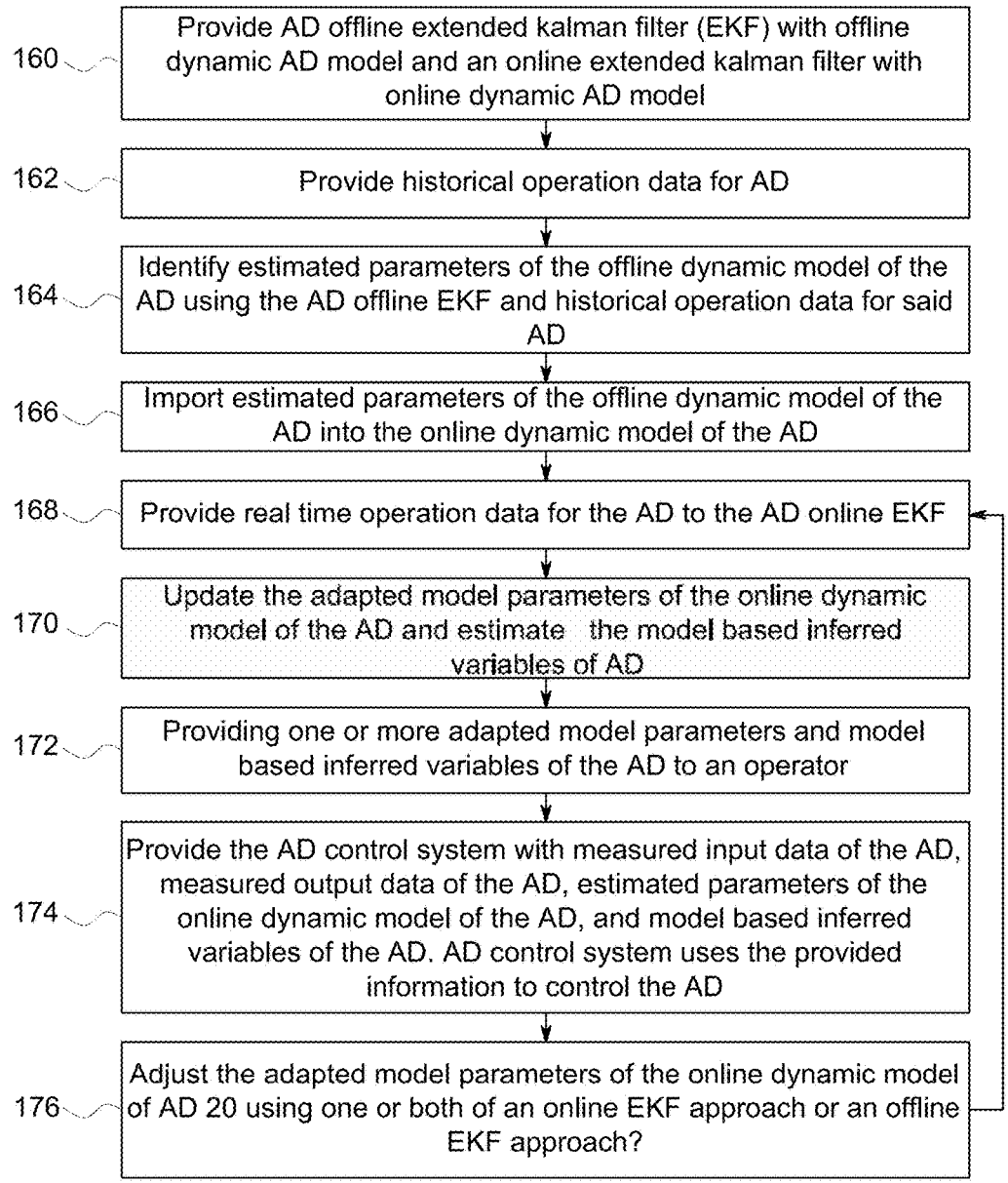
FIG. 12b is a flow chart depicting a method of operating an AD in accordance with aspects of the present technique.

FIG. 12b is a flow chart of another embodiment of a method of operating AD 20 through monitoring and control of AD 20 using the AD offline and online EKFs 251 and 252 and control system 200. Steps 160-172 and 176 are monitoring steps of AD 20 and step 174 is a controlling step of AD 20.

As can be seen, AD 20 is comprised of AD offline and online EKFs 251 and 252 and control system 200. AD 20 further has an AD reactor 24, which can be a CSTR, UASB, EGSB, mixed bed, moving bed, low-rate, or high-rate reactor. In some embodiments, AD 20 also has a PA reactor 22. When both are present, the AD reactor 24 and PA reactor 22 are modeled separately in both of the online and offline models 261 and 262 of AD 20. Further, in some embodiments, AD 20 has a mixing stage and at least one recycle line. The recycle line can be a PA reactor recycle line or an AD reactor recycle line.

In step 160 of a method of operating AD 20, AD offline extended Kalman filter (EKF) 251 having an offline dynamic model 261 of AD 20 is provided, and AD online EKF 252 having online dynamic model 262 of AD 20 is provided. The offline and the online dynamic models 261 and 262 of AD 20 are comprised of states, process material balances, energy balances, bio-chemical reaction kinetics, estimated parameters, and adapted model parameters. The adapted model parameters are a subset of the estimated parameters.

The materials for the process materials balances of the online and offline dynamic models 261 and 262 of AD 20 are comprised of insoluble organics, soluble substrates, VFA, biomass, inorganic carbon and alkalinity. The insoluble organics is comprised of carbohydrates, protein and fat. The soluble substrate and VFA include at least one of sugars, LCFA, amino acids, acetate acid, or propionate acid. The biomass includes biomass for acedogenesis, acetogenesis, acetoclastic methanogenesis and hydrogen methanogenesis bio-chemical processes. The inorganic carbon is comprised of at least one of carbon dioxide, carbonate, or bicarbonate. The alkalinity is comprised of alkalinity associated with bicarbonate, VFA, added alkali, and generation of ammonia and hydrogen sulfide. The bio-chemical reaction kinetics in said online and offline dynamic models of said AD are comprised of at least one of insoluble organics hydrolysis, acedogenesis, acetogenesis, acetoclastic methanogenesis, or hydrogen methanogenesis process.

Additionally, the estimated parameters and adapted model parameters of the offline dynamic model 261 of AD 20 and the online dynamic model 262 of AD 20 are comprised of at least one of PA reactor composite fraction of carbohydrate, PA reactor composite fraction of fat, PA reactor composite fraction of protein, PA reactor fraction of insoluble convertible to SBOD, PA reactor acedogenthese reaction coefficient, PA reactor biomass decay rate, PA reactor insoluble hydrolysis reaction coefficient, PA reactor insoluble flow out coefficient, PA reactor $CO_2$ escape coefficient, AD reactor composite fraction of carbohydrate, AD reactor composite fraction of fat, AD reactor composite fraction of protein, AD reactor fraction of insoluble convertible to SBOD, AD reactor acedogenthese reaction coefficient, AD reactor acetogenesis reaction coefficient, AD reactor acetoclastic methanogenesis reaction coefficient, AD reactor hydrogen methanogenesis reaction coefficient, AD reactor biomass decay rate, PA reactor insoluble hydrolysis reaction coefficient, or PA reactor insoluble flow out coefficient. At least one of the estimated parameters of the offline dynamic model 261 of AD 20 and the model based inferred variables of the online dynamic model 262 of AD 20 are estimated with confidence intervals.

In step 162, historical operation data of AD 20 is provided. The historical operation data is comprised of historical measured input data, historical measured output data, and historical laboratory analysis data. More specifically, in some embodiments, the historical operation data of AD 20 is comprised of at least one of raw influent pH, raw influent temperature, raw influent flow rate, raw influent TOC, raw influent TIC, added alkali flow rate, PA reactor fluid level, AD feed flow rate, raw influent SCOD, raw influent TCOD, raw influent SBOD, raw influent VSS, raw influent TSS, raw influent soluble inorganic nitrogen, raw influent VFA, added alkali concentration, PA reactor pH, PA effluent TOC, PA effluent TIC, AD biogas flow rate, AD biogas $CH_4$ concentration, AD Biogas $CO_2$ concentration, AD reactor pH, AD effluent TOC, AD effluent TIC, AD effluent VFA, AD effluent alkalinity, AD reactor MLVSS, AD effluent TCOD, AD effluent SCOD, AD effluent VSS, or AD effluent TSS.

In step 164, estimated parameters of offline dynamic model 261 of AD 20 are identified using AD offline EKF 251 and the historical operation data for AD 20.

In step 166, the estimated parameters identified in step 164 are imported from the offline dynamic model 261 of AD 20 into the online dynamic model 262 of AD 20.

In step 168, real time operation data for AD 20 is provided to AD online EKF 252. The real time operation data is comprised of real time measured input data and real time measured output data of AD 20. More specifically, in some embodiments of AD 20, the real time operation data of AD 20 is comprised of at least one of raw influent pH, raw influent temperature, raw influent flow rate, raw influent TOC, raw influent TIC, added alkali flow rate, PA reactor fluid level, AD feed flow rate, raw influent SCOD, raw influent TCOD, raw influent SBOD, raw influent VSS, raw influent TSS, raw influent soluble inorganic nitrogen, raw influent VFA, added alkali concentration, PA reactor pH, PA effluent TOC, PA effluent TIC, AD biogas flow rate, AD biogas $CH_4$ concentration, AD Biogas $CO_2$ concentration, AD reactor pH, AD effluent TOC, AD effluent TIC, AD effluent VFA, AD effluent alkalinity, AD reactor MLVSS, AD effluent TCOD, AD effluent SCOD, AD effluent VSS, or AD effluent TSS.

In step 170, the adapted model parameters of the online dynamic model 262 of AD 20 are updated and the model based inferred variables of AD 20 are estimated using the AD online EKF 252, the online dynamic model of AD 20, the real time measured input data of AD 20, and the real time measured output data of AD 20.

The model based inferred variables of the online dynamic model 262 of AD 20 are comprised of at least one of the following unmeasured inputs or outputs of AD 20: raw influent insoluble COD, raw influent insoluble inert COD, raw influent soluble inert COD, raw influent SBOD saccharide, raw influent SBOD LCFA, raw influent SBOD amino acid, raw influent propionate acid, raw influent acetate acid, raw influent inorganic carbon content, raw influent alkalinity, raw influent inorganic nitrogen, raw influent SCOD, raw influent TCOD, raw influent SBOD, PA reactor alkalinity, PA reactor VFA, PA reactor temperature, PA reactor SCOD, PA reactor TCOD, PA reactor SBOD, AD reactor alkalinity, AD reactor VFA, AD reactor temperature, AD reactor SCOD, AD reactor SBOD, AD reactor acedogenthese biomass, AD reactor acetogenesis biomass, AD reactor acetoclastic methanogenesis biomass, AD reactor hydrogen methanogenesis biomass, AD reactor insoluble COD, AD reactor insoluble inert COD, AD reactor soluble inert COD, AD reactor SBOD saccharide, AD reactor SBOD LCFA, AD reactor SBOD amino acid, AD reactor propionate acid, AD reactor acetate acid, AD reactor inorganic carbon content, AD reactor alkalinity, AD reactor inorganic nitrogen, AD reactor SCOD, AD reactor TCOD, AD reactor SBOD, SCOD conversion rate, $CH_4$ conversion efficiency, or recycle flow rate.

In step 172, one or more of the adapted model parameters of the online dynamic model 262 of AD 20 and one or more of the model based inferred variables of AD 20 are provided to an operator of AD 20.

In step 174, control system 200 of AD 20 is provided with one or more of the real time measured input data of AD 20, real time measured output data of AD 20, estimated parameters of the online dynamic model of AD 20, or model based inferred variables of AD 20. AD control system 200 uses this information to control at least one of a nutritional additive concentration of said AD reactor 24, a nutritional additive concentration of said PA reactor 22, pH of said AD reactor 24, pH of said PA reactor 22, biomass concentration of said AD reactor 24, fluid level of said PA reactor 22, or a recycle flow rate of said AD 20.

Wherein controlling said nutritional additive concentration of said AD 20 prevents biomass overfeeding and starvation, wherein controlling said nutritional additive concentration of said PA reactor 22 prevents biomass overfeeding and starvation, wherein controlling said pH of said AD reactor 24 minimizes alkali dosing, wherein controlling said pH of said PA reactor 22 minimizes alkali dosing, wherein controlling said biomass concentration of said AD reactor 24 offsets biomass inhibition and saves alkali, wherein controlling a recycle flow rate to said PA reactor 22 minimizes alkali dosing and maintains fluid level of said PA reactor 22, and wherein controlling a recycle flow rate of said AD reactor 24 maximizes COD conversion and biogas generation.

AD control system 200 is comprised of an AD supervisory control system 201 and an AD low-level control system 202. The AD supervisory control system 201 is comprised of at least one of an AD reactor pH supervisory controller 700, a PA reactor pH supervisory controller 701, or an PA:AD overall recycle flow ratio supervisory controller 720.

AD reactor pH supervisory controller 700 is comprised of an AD reactor nonlinear Proportion-Integration (PI) pH controller 705 and an AD reactor Proportion (P) alkalinity controller 710 in a cascaded configuration. PA reactor pH supervisory controller 701 is comprised of a PA reactor nonlinear PI pH controller 706 and a PA reactor P alkalinity controller 711 in a cascaded configuration. The PA:AD overall recycle flow ratio supervisory controller 720 is comprised of a PA:AD recycle ratio controller 725, and a PA reactor and AD reactor recycle flow rate controller 730.

In some embodiments, at least one of AD reactor pH supervisory controller 700 or PA reactor pH supervisory controller 701 uses a model based inferred variable of AD 20, including, but not limited to, the alkalinity of PA reactor 22 or AD reactor 24. Further, in some embodiments, at least one of said AD reactor pH supervisory controller 700 or PA reactor pH supervisory controller 701 has a feedforward control action which uses a model based inferred variable of said AD 20, including, but not limited to, raw influent alkalinity.

AD low-level control system 202 is comprised of at least one of an AD reactor biomass concentration controller 735, a PA reactor fluid level controller 737, a PA reactor nutritional additive concentration controller 51, or an AD reactor nutritional additive concentration controller 61.

In some embodiments, at least one of the AD reactor biomass concentration controller 735, PA reactor nutritional additive concentration controller 51, or said AD reactor nutritional additive concentration controller 61 uses at least one of the estimated parameters of the online dynamic model 262 of AD 20 or a model based inferred variable of AD 20, including, but not limited to, at least one of reaction coefficients and biomass concentrations for hydrolysis, acedogenthese, acetogenesis, acetoclastic methanogenesis, or hydrogen methanogenesis processes.

In step 176, the AD operator, or an automated system such as computer 1071, decides whether it is necessary to adjust the adapted model parameters of the online dynamic model 262 of AD 20 (e.g. reporting incorrect or inconsistent values for model predicted outputs or model based inferred variables). If it is not necessary to adjust the adapted model parameters, the method returns to step 168.

In some embodiments, the decision of whether or not to adjust the adapted model parameters is determined by elapsed time, such as an adjustment of the adapted model parameters using the online EKF approach is performed about every 30 minutes to once a day, and an adjustment of the adapted model parameters using the offline EKF approach is performed about every few weeks to few months.

If it is necessary to adjust the adapted model parameters, the operator can choose to use one or both of an online EKF approach or an offline EKF approach to update the adapted model parameters of the online dynamic model 262. Traditionally, the offline EKF approach is only used periodically, in some embodiments about every few weeks or months. The online EKF approach is used more frequently, in some embodiments as frequently as about every 30 minutes.

In the online EKF approach, model predicted outputs of AD 20 are calculated using AD online EKF 252, online dynamic model 262 of AD 20, real time measured input data of AD 20, and real time measured output data of AD 20. The measured output data of AD 20 and the model predicted outputs of AD 20 are then compared, and the adapted model parameters of online dynamic model 262 of AD 20 are updated such that the real time measured output data of AD 20 substantially correspond with the model predicted outputs of AD 20.

In the offline EKF approach, the estimated parameters of the offline dynamic model 261 of AD 20 are re-identified using the AD offline EKF 251 and the historic operation data for AD 20. The estimated parameters of offline dynamic model 261, which contain the updated adapted model parameters as a subset, are then imported into the online dynamic model 262.

In some embodiments of the offline EKF approach, the adapted model parameters of the online dynamic model 262 of AD 20 are imported into the offline dynamic model 261 of AD 20 before the estimated parameters of the offline dynamic model 261 of AD 20 are re-identified. This allows the estimated parameters of the offline dynamic model 261 to converge faster when they are re-identified by AD offline EKF 251.

After step 176, the method returns to step 168 to provide more real time operation data of AD 20 for the next time point to the AD online EKF 252.

It is contemplated that in some embodiments of this method, the adapted model parameters of the online dynamic model 262 of AD 20 can be tuned using different weights for online measurements and prior knowledge of measurement accuracy. Further, it is contemplated that in some embodiments of the method described above, limits are applied to one or more of said estimated parameters and said adapted model parameters; wherein constraints are applied to one or more of said model based inferred variables.

It is contemplated that in some embodiments, at least one of monitoring AD 20 or controlling AD 20 is performed using a computer.

It is contemplated that the method of operating AD 20 includes variations of the methods depicted in FIGS. 12a-b. Some embodiments of such methods may be arrived at by substituting steps or underlying details of one of 12a or 12b, and using the steps or underlying details in the other of 12a or 12b.

Figure 16A:
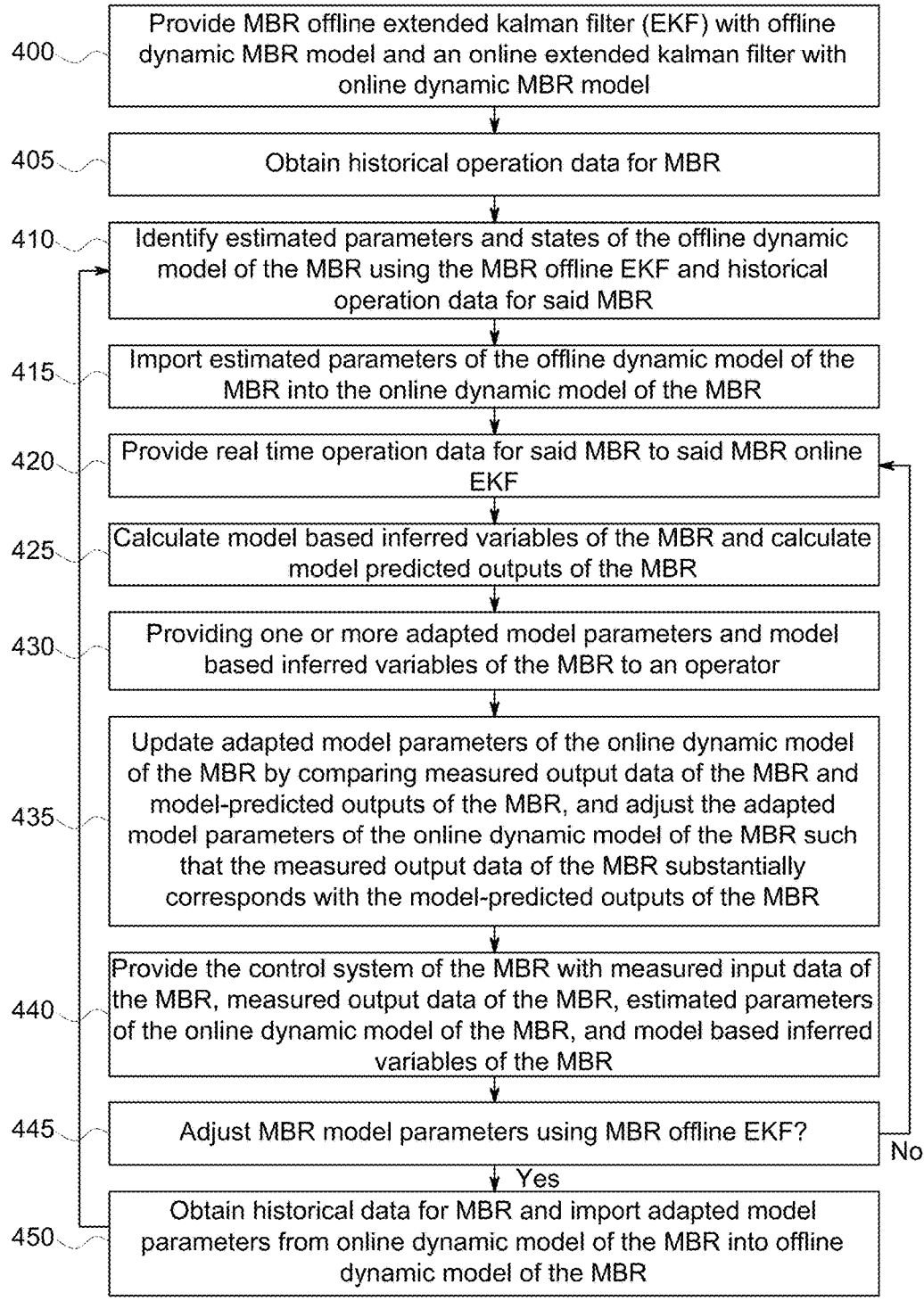
FIG. 16a is a flow chart depicting a method of operating an MBR in accordance with aspects of the present technique.
Figure 16B:
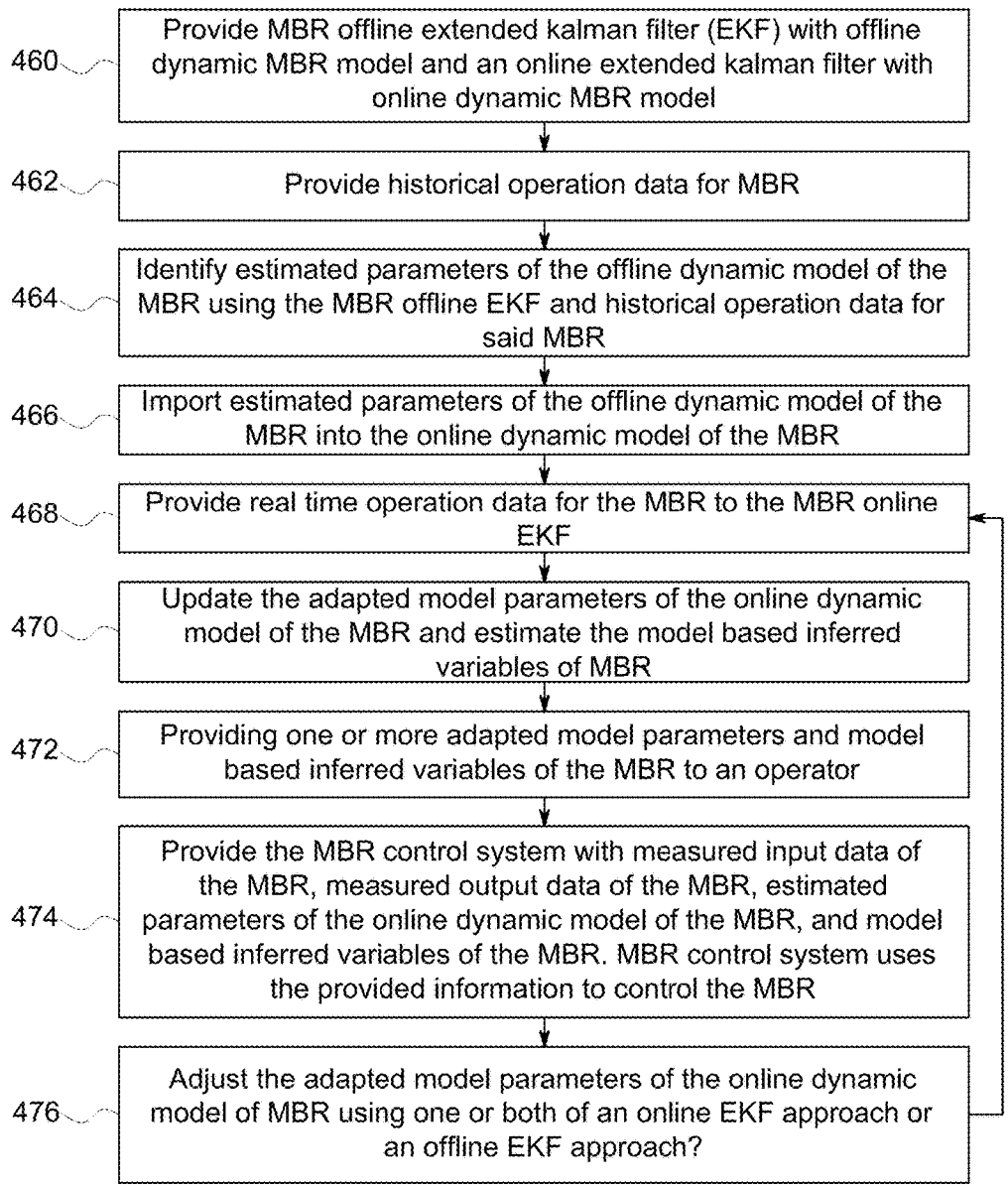
FIG. 16b is a flow chart depicting a method of operating an MBR in accordance with aspects of the present technique.

Further, it is contemplated that the method of operating AD 20 depicted in FIGS. 12a-b can be combined with the method of operating MBR 30 depicted in FIGS. 16a-b to arrive at a method for operating WWTP 10 having one or both of AD 20 and MBR 30.

Figure 13:
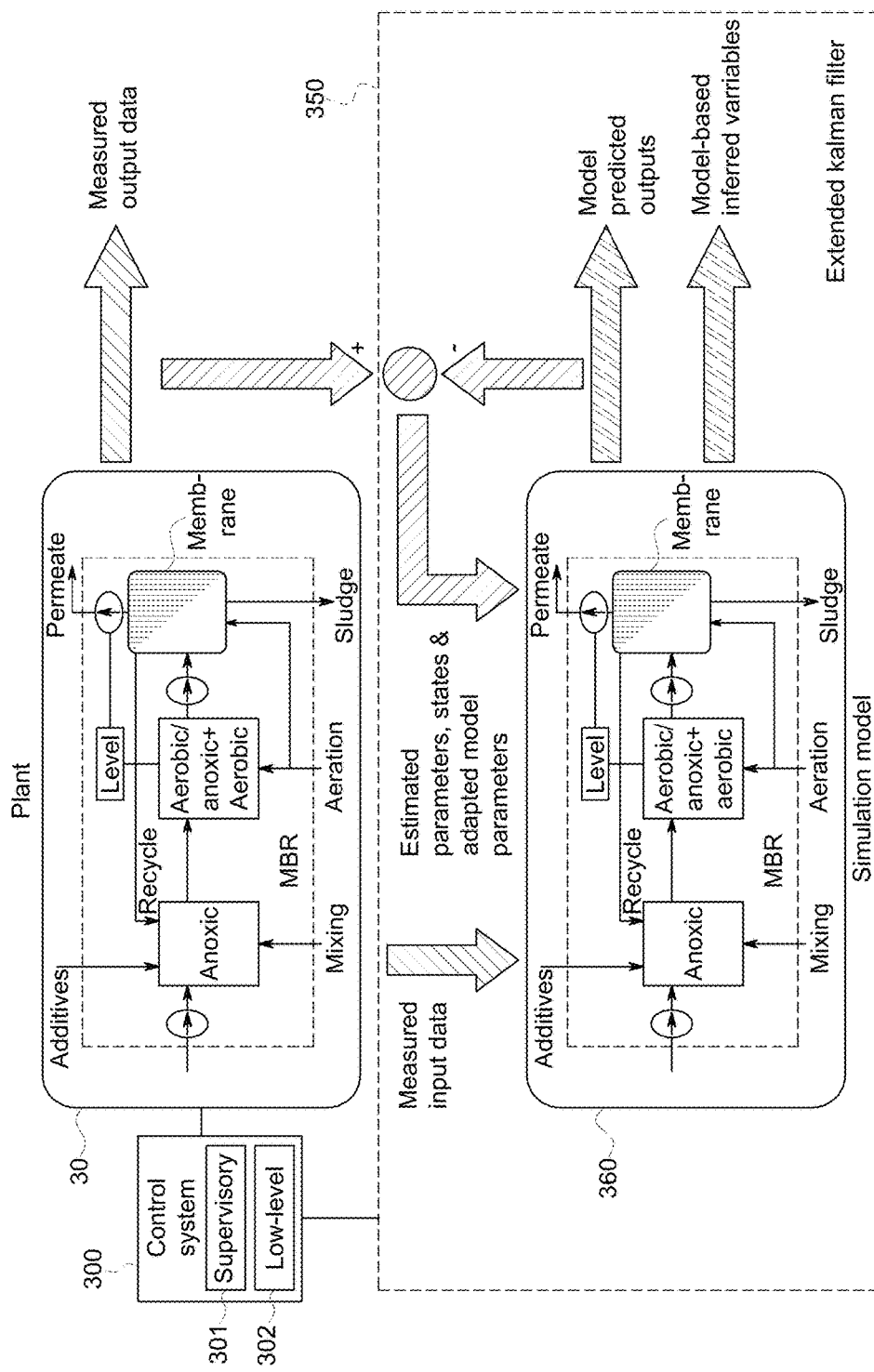
FIG. 13 is a block diagram of the overall architecture for an MBR having an extended Kalman filter (EKF) and a control system in accordance with aspects of the present technique.

As was previously stated, the developed model of MBR 30 is used as the basis for a method of online monitoring and control of the MBR 30 of wastewater treatment plant 10. More specifically, for online monitoring of the MBR 30, a set of online sensors are used along with model-based estimation of variables not measured directly, but estimated through the use of a constrained Extended Kalman Filter. FIG. 13 shows the overall architecture for monitoring an embodiment of MBR 30 with control system 300, using a combination of online sensors that measure the measured input data and measured output data of MBR 30. An extended Kalman filter 350 containing the dynamic model 360 of MBR 30 discussed above uses the measured input data and measured output data of MBR 30 to estimate model parameters, model states, adapted model parameters, model predicted outputs, and model based inferred variables of dynamic model 360.

The comparison of the estimated and actual values of the measured output data, offline laboratory testing data and estimated values of model predicted outputs and model based inferred variables by extended Kalman filter 350 estimate values for the estimated parameters, states, and adapted model parameters of dynamic model 360 of MBR 30.

Below are exemplary lists of measured output data, measured input data, estimated parameters, adapted model parameters, model predicted outputs, and model based inferred variables for MBR 30 of WWTP 10. MBR 30 has an MBR control system 300, MBR online EKF 352, and MBR offline EKF 351.

| Model Based Inferred Variables | |
| --- | --- |
| Outputs | Inputs |
| Anoxic Tank SCOD | Raw Influent Alkalinity |
| Anoxic Tank MLVSS | Raw Influent Nitrate nitrogen |
| Anoxic Tank Nitrate nitrogen | Raw Influent Ammonia-nitrogen |
| Anoxic Tank Ammonia-nitrogen | Raw Influent SCOD |
| Anoxic Tank Biodegradable COD | Raw Influent TCOD |
| Aerobic Tank SOCD | Raw Influent Readily Biodegradable COD |
| Aerobic Tank MLVSS | |
| Aerobic Tank Nitrate nitrogen | Raw Influent Slowly Biodegradable COD |
| Aerobic Tank Ammonia-nitrogen | |
| Aerobic Tank Biodegradable COD | Raw Influent VSS |
| Membrane Tank MLVSS | Raw Influent TSS |
| Membrane Permeate SCOD | Raw Influent Inorganic Inert Particulate |
| Membrane Permeate Biodegradable COD | |
| Membrane Permeate TCOD | |
| Membrane Permeate Nitrate nitrogen | |
| Membrane Permeate Ammonia-nitrogen | |
| Wasting Sludge MLVSS | |
| COD Removal Rate | |
| Nitrogen Removal Rate | |

| Estimated Parameters and Adapted Model Parameters | Updated By Online EKF (Adapted Model Parameters) | Estimated By Offline EKF (Estimated Parameters) |
| --- | --- | --- |
| Hetrotrophic maximum specific growth rate | X | X |
| Anoxic/Aerobic hetrotroph growth rate | X | X |
| Anoxic/Aerobic hydrolysis rate fraction | | X |
| Particulate hydrolysis max specific rate constant | | X |
| Autotrophic maximum specific growth rate | X | X |
| Decay constant for hetrotrophs | | X |
| Decay constant for autotrophs | | X |
| Yield of hetrotrophic biomass | X | X |
| Yield of autotrophic biomass | X | X |
| Carbon content in soluble substrate | | X |
| Carbon content of participate substrate | | X |
| Carbon content of soluble inert | | X |
| Carbon content of particulate nondegradable organic | | X |
| Mass transfer coeff for O2 removal in Aerobic tank | | X |
| Mass transfer coeff for CO2 removal in Anoxic tank | | X |

| Measured Input Data | Online | Offline |
| --- | --- | --- |
| Raw Influent pH | X | X |
| Raw Influent Temperature | X | X |
| Raw Influent Flow Rate | X | X |
| Raw Influent TOC | X | X |
| Raw Influent TIC | X | X |
| Added Alkali Flow Rate | X | X |
| Added Alkali concentration | | X |
| Effluent Flow Out Rate | X | X |
| Raw Influent SCOD | | X |
| Raw Influent TCOD | | X |
| Raw Influent Readily Biodegradable COD | | X |
| Raw Influent Slowely Biodegradable COD | | X |
| Raw Influent VSS | | X |
| Raw Influent TSS | | X |
| Raw Influent Nitrate nitrogen | | X |
| Raw Influent Ammonia-nitrogen | | X |
| Raw Influent Soluble Biodegradable Organic Nitrogen | | X |
| Raw Influent Particulate Degradable Organic Nitrogen | | X |
| Raw Influent Inorganic Inert Particulate | | X |
| Membrane Permeate Flow Rate | X | X |
| Wasting Sludge Flow Rate | X | X |
| Anoxic Tank Addition Biodegradable COD Flow | X | X |

| Measured Output Data & Model Predicted Outputs | Online | Offline |
| --- | --- | --- |
| Anoxic Tank Reactor pH | X | X |
| Anoxic Tank Dissolved Oxygen | X | X |
| Anoxic Tank Temperature | X | X |
| Anoxic Tank Liquid Level | X | X |
| Anoxic Tank MLVSS | | X |
| Anoxic Tank MLSS | X | X |
| Aerobic Tank Blower Air Flow Rate | X | X |
| Aerobic Tank Reactor pH | X | X |
| Aerobic Tank Alkalinity | X | X |
| Aerobic Tank MLVSS | | X |
| Aerobic Tank MLSS | X | X |
| Aerobic Tank Dissolved Oxygen | X | X |
| Aerobic Tank Temperature | X | X |
| Aerobic Tank Liquid Level | X | X |
| Membrane Tank MLSS | X | X |
| Membrane Tank MLVSS | | X |
| Membrane Permeate SCOD | | X |
| Membrane Permeate TCOD | | X |
| Membrane Permeate TOC | X | X |
| Membrane Permeate TIC | X | X |
| Membrane Permeate Nitrate nitrogen | X | X |
| Membrane Permeate Ammonia-nitrogen | X | X |
| Wasting Sludge MLSS | X | X |
| Wasting Sludge MLVSS | | X |

It is understood that the lists above of measured output data, measured input data, estimated parameters, adapted model parameters, model predicted outputs, and model based inferred variables are exemplary, can vary from one application to another application, and can be established by a person having ordinary skill in the art when examining a particular MBR of interest based on the person's knowledge of the process and application. Further, it is understood that the adapted model parameters are a subset of the estimated parameters, which are more extensive. Additionally, it is understood that the model based inferred variables include both unmeasured inputs and outputs for MBR 30.

Figure 14:
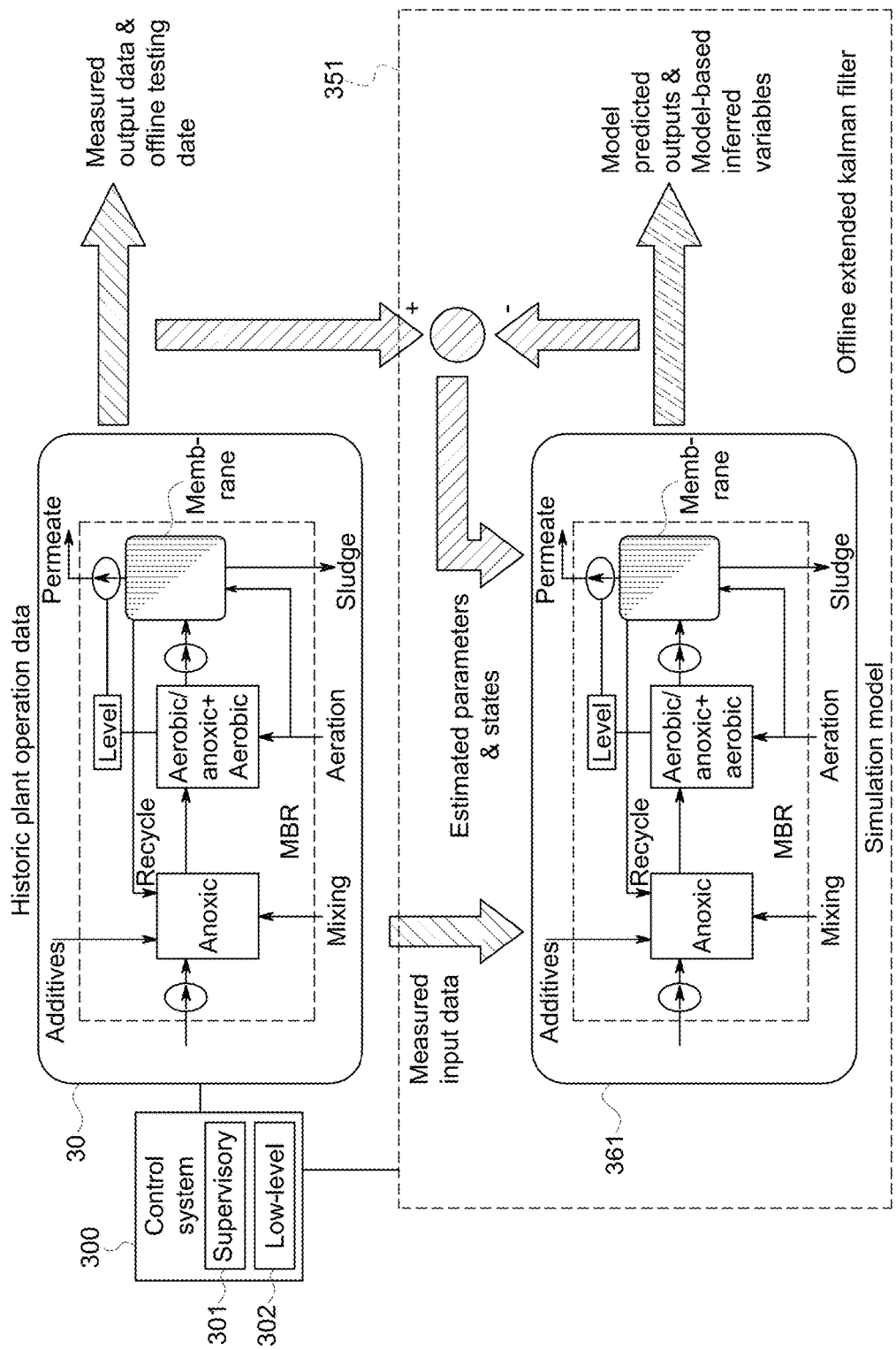
FIG. 14 is a block diagram of the architecture for an MBR having an online EKF and a control system in accordance with aspects of the present technique.

FIG. 14 shows the overall architecture for the MBR offline EKF 351 containing a model 360 of MBR 30 for parameter identification and adaptation of an embodiment of MBR 30 having control system 300. Control system 300 has a supervisory control system 301 and a low-level control system 302.

Figure 15:
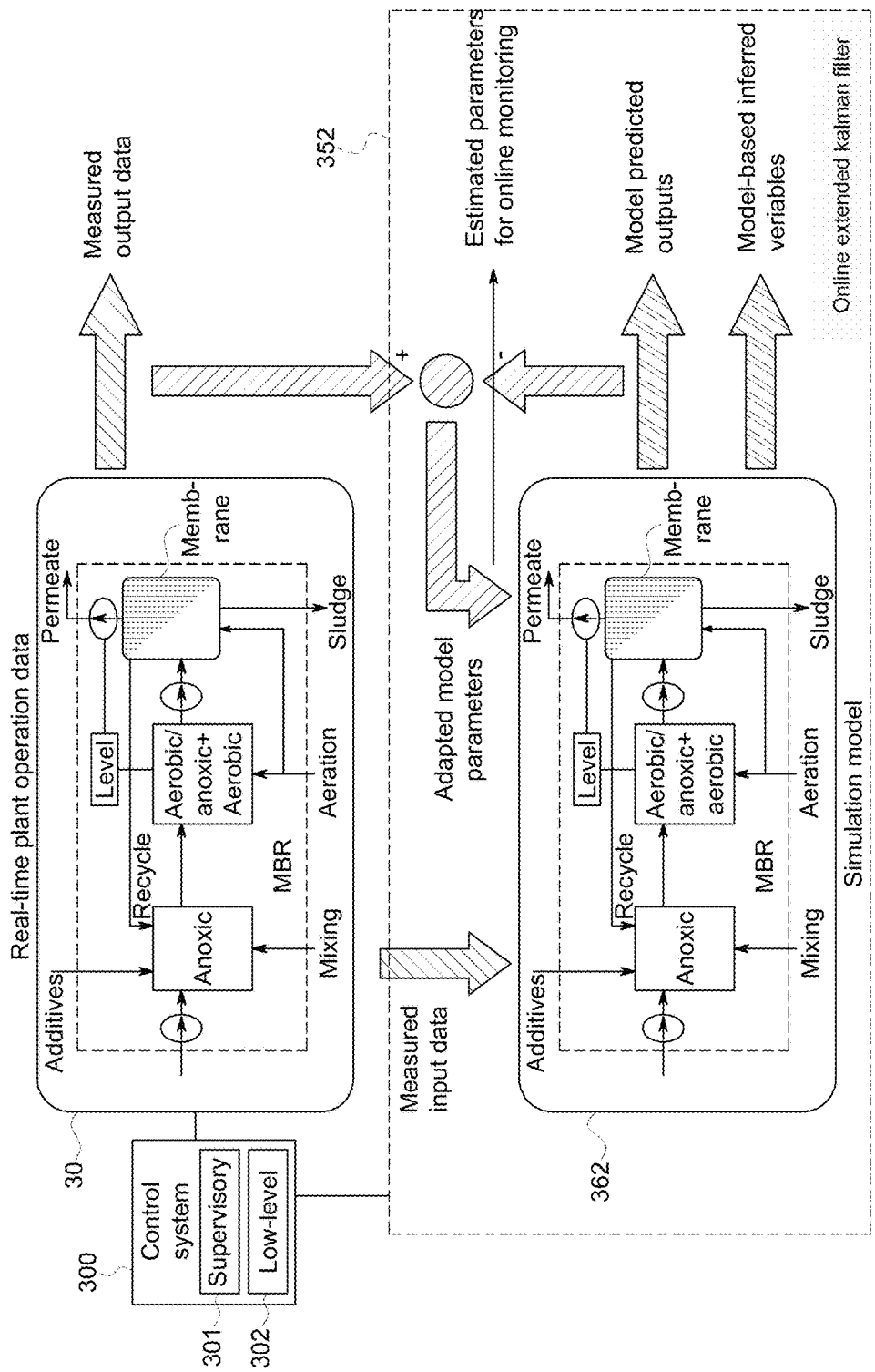
FIG. 15 is a block diagram of the architecture for an MBR having an offline EKF and a control system in accordance with aspects of the present technique.

FIG. 15 shows the overall architecture of an MBR online EKF 352 containing a model of MBR 30 for real-time monitoring/virtual sensing/controlling of an embodiment of MBR 30 having control system 300.

Additionally, it is understood that in some embodiments of WWTP 10, if an MBR 30 is located upstream of AD 20, some of the model based inferred variables calculated by MBR online EKF 352 using online dynamic model 362 of MBR 30, such as the composition and flow rate of MBR effluent, are provided to AD 20 by MBR online EKF 352, therefore enabling feed forward control of AD 20 by AD control system 200 which uses the provided data as inputs. It is understood that the information provided regarding the composition of the effluent includes multiple pieces of information, such as the individual amounts of elements and compounds contained in the effluent (e.g. Nitrogen, Oxygen, etc.).

Additionally, it is understood that in some embodiments of WWTP 10, if an AD 20 is located upstream of MBR 30, some of the model based inferred variables calculated by AD online EKF 252 using AD online model 262 of AD 20, such as the composition and flow rate of AD effluent, are provided to MBR 30 by AD online EKF 252, therefore enabling feed forward control of MBR 30 by MBR control system 300 which uses the provided data as inputs. It is understood that the information provided regarding the composition of the effluent includes multiple pieces of information, such as the individual amounts of elements and compounds contained in the effluent (e.g. Nitrogen, Oxygen, etc.).

Further, the states for offline dynamic model 361 of MBR 30 in MBR offline EKF 351 and online dynamic model 362 of MBR 30 in MBR online EKF 352, are defined above in equation 14.

Further, it is understood that both offline dynamic model 361 of MBR 30 and online dynamic model 362 of MBR 30 both contain estimated parameters and adapted model parameters, a subset of the adapted model parameters. Accordingly, the structures of offline dynamic model 361 of MBR 30 and online dynamic model 362 of MBR 30 are the same. However, all of the estimated parameters are identified by MBR offline EKF 351 in offline dynamic model 361 of MBR 30. Meanwhile, only the adapted model parameters are identified (updated) in the online dynamic model 362 of MBR 30 by MBR online EKF 352. Further, it is understood that the offline dynamic model 361 of MBR 30 and online dynamic model 362 of MBR 30 are based on first principles with physical meanings for the respective estimated parameters and adapted model parameters with unknown values (e.g., the reaction rate kinetic parameter) whose values are estimated by best fitting.

It is understood that the measured input data and measured output data is data obtained from physical sensors of MBR 30. Further, model based inferred variables are virtual sensors that have traditionally only been available through periodic offline testing. A model based inferred variable of MBR 30 is a "virtual sensed" variable that is estimated by the MBR online EKF 352 using the online dynamic model 362 of MBR 30, real time measured input data of MBR 30, and real time measured output data of MBR 30. The model based inferred variables of MBR 30 are first developed by the MBR online EKF 351 using offline dynamic model 361 of MBR 30, historical measured input data of MBR 30, historical measured output data of MBR 30, and historical offline testing data of MBR 30. It is understood that the model based inferred variables include both unmeasured inputs and outputs of MBR 30.

A model predicted output is an output of MBR 30 that is estimated by the MBR offline EKF 351 and MBR online EKF 352. The MBR offline EKF 351 estimates the model predicted outputs of MBR 30 using offline dynamic model 361 of MBR 30, historical measured input data of MBR 30, historical measured output data of MBR 30, and historical offline testing data of MBR 30. The MBR online EKF 352 estimates the model predicted outputs of MBR 30 using the online dynamic model 362 of MBR 30, real time measured input data, and real time measured output data. It is understood that each model predicted output of MBR 30 corresponds to a measured output of MBR 30. Estimated parameters are parameters that are identified in the offline dynamic model 361 of MBR 30 located in MBR offline EKF 351, such that for a given historical input data value, the predicted historical output data value or model based inferred variable value matches the corresponding actual historical output data value or actual offline laboratory testing value. The estimated parameters from the offline dynamic model 361 of MBR 30 located in MBR offline EKF 351 are imported into the online dynamic model 362 of MBR 30 located in MBR online EKF 352. The adapted model parameters are a subset of the estimated parameters, which are updated in the MBR online EKF 352. The MBR online EKF 352 is used to generate real time estimated values for the model predicted outputs and model based inferred variables of MBR 30.

In one embodiment of a method of monitoring and controlling MBR 30, initially an MBR offline EKF 351, such as the one shown in FIG. 14, is used to identify estimated parameters (e.g. reaction kinetics) and states for the offline dynamic model 361 of MBR 30 to match historical operation data from MBR 30. During this offline phase, extensive data, both available historical measured output data, measured input data, as well as offline lab-analysis data from over a period of operation are used to identify the states and estimated parameters of the offline dynamic model 361 of MBR 30. Once the model parameters of offline dynamic model 361 of MBR 30 are identified, the estimated parameters are imported from offline dynamic model 361 of MBR 30 into the online dynamic model 362 of MBR 30. The adapted model parameters, a subset of the estimated parameters, are updated by the online EKF 352 of MBR 30. The online dynamic model 362 of MBR 30 is used in MBR online EKF 352, such as the one shown in FIG. 15, for online monitoring, wherein real time measured output data and measured input data from MBR 30 online sensor data is used. In the online estimation, one unknown is the variation in the feed composition to MBR 30. The MBR online EKF 352 is used to estimate the unknown/varying feed compositions along with any adapted model parameters that are likely to vary frequently and are prudent for monitoring, such as the inhibition of aerobic bio-chemical reaction kinetics due to a toxic ingredient in the feed. Once the unknown feed composition is identified correctly, the model based inferred variables (e.g. biomass concentration, alkalinity, VFA, etc.) provides a "virtual" estimate of these unmeasured variables for more complete online monitoring. Traditionally, these model based inferred variables were ascertained via offline laboratory testing and not available in real time through actual real time sensors. Accordingly, MBR online EKF 352 provides a real-time estimated value for these model based inferred variables.

FIG. 16a is a flow chart of a method of operating MBR 30 through online monitoring and control of MBR 30 using the MBR offline and online EKFs 351 and 352 and control system 300. Steps 400-435 and 445-450 are monitoring steps of MBR 30 and step 440 is a controlling step of MBR 30.

In step 400, the monitoring of MBR 30 is commenced by MBR offline EKF 351 having an offline dynamic model 361 of MBR 30, providing an MBR online EKF 352 having an online dynamic model 362 of MBR 30. The online and offline dynamic models 361 and 362 of MBR 30 have states, process material balances, energy balances and bio-chemical reaction kinetics. The offline dynamic model 351 and online dynamic model 352 of MBR 30 both have estimated parameters and adapted model parameters. The adapted model parameters are a subset of the estimated parameters.

The estimated parameters of offline dynamic model 361 of MBR 30 and adapted model parameters of online dynamic model 362 of MBR 30 are comprised of kinetic parameters and stoichiometric coefficients for reactions of at least one of insoluble organics hydrolysis, heterotrophic, autotrophic, ammonification, biomass decay, and biomass growth.

The material balances in said online and offline dynamic models 361 and 362 of MBR 30 are comprised of particulate inert, slowly degradable substrate, heterotrophic biomass, autotrophic biomass, decayed biomass, soluble inert, soluble readily degradable substrate, dissolved oxygen, dissolved nitrate-N(Nitrogen), dissolved ammonia-N, particulate biodegradable-N, and bicarbonate alkalinity. The insoluble organics are converted to soluble COD via hydrolysis process. The organic nitrogen is also converted into soluble nitrogen by hydrolysis. Other bio-chemical reactions include material aerobic heterotroph, anoxic heterotroph, aerobic autotroph, decay of heterotroph, decay of autotroph, and ammonification of soluble organic N. The inorganic carbon is comprised of at least one of carbon dioxide, carbonate and bicarbonate. Additionally, alkalinity is comprised of alkalinity associated with bicarbonate, VFA, added alkali, and generation of ammonia.

In some embodiments, limits are applied to one or more of the estimated parameters, adapted model parameters, and states. Further, in some embodiments, constraints are applied to one or more of the model-predicted outputs and model based inferred variables. These limits and constraints can be lower and upper limits specified by a person having ordinary skill in the art based on the person's knowledge of the process and application.

In step 405, historical operation data for MBR 30 is obtained. The historical operation data includes measured input data, measured output data, and laboratory analysis data. More specifically, historical operation data of MBR 30 may include at least one of liquid flow rates, aeration flow rate, TOC in liquid streams, TIC in liquid streams, MBR pH, anoxic tank pH, aerobic tank pH, membrane tank pH, anoxic tank bCOD, bCOD in MBR feed, NH3-N in MBR feed, NO3-N in MBR feed, NH3-N in MBR effluent, NO3-N in MBR effluent, DO in MBR effluent, and bCOD in MBR effluent.

In step 410, estimated parameters of the offline dynamic model 361 of MBR 30 are identified using the MBR offline EKF 351 and the historical operation data for MBR 30. At least one of the estimated parameters of offline dynamic model 361 of MBR 30 is estimated with confidence intervals, which are the estimated variances corresponding to the estimated parameters of offline dynamic model 361 of MBR 30. Stated alternatively, the confidence intervals are determined by their corresponding variances, normally assumed as Normal distribution, therefore 95% confidence intervals are approximate four times of the standard deviations.

The estimated parameters of the offline dynamic model 361 are identified by MBR offline EKF 351 simulating one time step of the historical operation data for MBR 30 to update values for the estimated parameters, model predicted outputs, states, and covariance estimates and develop model based inferred variables. In one embodiment, a dynamic nonlinear model of MBR 30 and measured input data are used to simulate and update the estimated parameters, model predicted outputs, states, and model based inferred variables. A linearized dynamic model of MBR 30 is used to simulate and update the covariance estimate.

The method progresses to step 415 once MBR offline EKF 351 simulates all of the historical data time steps or a user intervenes.

In step 415, the estimated parameters of the offline dynamic model 361 of said MBR 30 are imported into the online dynamic model 362 of MBR 30.

In step 420, real time operation data for MBR 30 is provided to MBR online EKF 352. The real time operation data is comprised of measured input data and measured output data of MBR 30. More specifically, real time operation data of MBR 30 may include at least one of liquid flow rates, aeration flow rates, TOC in liquid streams, TIC in liquid streams, MBR pH, anoxic tank pH, aerobic tank pH, membrane tank pH, anoxic tank bCOD, bCOD in MBR feed, $NH_3$—N in MBR feed, $NO_3$—N in MBR feed, $NH_3$—N in MBR effluent, $NO_3$—N in MBR effluent, DO in MBR effluent, and bCOD in MBR effluent.

In step 425, model based inferred variables of MBR 30 are calculated using MBR online EKF 352, the online dynamic model 362 of MBR 30, measured input data of MBR 30, and measured output data of MBR 30. Model predicted outputs of MBR 30 are calculated using MBR online EKF 352, the online dynamic model 362 of MBR 30, measured input data of MBR 30, and measured output data of MBR 30. At least one of the model based inferred variables of online dynamic model 362 of MBR 30 is estimated with confidence intervals, which are the estimated variances corresponding to the model based inferred variables of online dynamic model 362 of MBR 30. Stated alternatively, the confidence intervals are determined by their corresponding variances, normally assumed as Normal distribution, therefore 95% confidence intervals are approximate four times of the standard deviations. The model based inferred variables of online dynamic model 362 of MBR 30 are comprised of at least one of feed composition, biomass activity, biomass concentration, COD, MLSS, MLVSS, HRT, SRT, and reduction in $O_2$ mass transfer coefficient due to biomass quality changes.

In step 430, one or more adapted model parameters and model based inferred variables of MBR 30 are provided to an operator of MBR 30. It is understood that offline laboratory testing providing results corresponding to some of the model based inferred variables of MBR 30 will still take place and the results are recorded for use as historical operation data and are provided to the operator.

In step 435, the adapted model parameters of the online dynamic model 362 of MBR 30 are updated by comparing the measured output data of MBR 30 and model predicted outputs of MBR 30, and adjusting the adapted model parameters of the online dynamic model 362 of MBR 30, such that the measured output data of MBR 30 substantially corresponds with the model predicted outputs of MBR 30. It is contemplated that in some embodiments, the adapted model parameters of online dynamic model 362 of MBR 30 can be further tuned using different weights for online measurements and prior knowledge of measurement accuracy.

In step 440, control system 300 is provided with measured input data of MBR 30, measured output data of MBR 30, estimated parameters of online dynamic model 362 of MBR 30, adapted model parameters of online dynamic model 362 of MBR 30, and model based inferred variables of MBR 30 to control at least one of pH of said optional anoxic tank 31, pH of said aerobic tank 32, fluid level of said aerobic tank 32, DO of said aerobic tank 32, MLSS concentration of said membrane tank 33, bCOD addition flow rate setpoint of said anoxic tank 31, at least one nutritional additive concentration of said optional anoxic tank 31, and at least one recycle flow setpoint of said MBR 30.

Control system 300 has an MBR supervisory control system 301 and an MBR low level control system 302. MBR supervisory control system 301 is comprised of at least one of aerobic tank DO supervisory controller 1040, anoxic tank recycle flow supervisory controller 1045, and an anoxic tank bCOD addition flow rate supervisory control scheme 1035.

Anoxic tank bCOD addition flow supervisory control scheme 1035 is comprised of an anoxic tank bCOD setpoint supervisory controller 1050, an anoxic tank bCOD addition flow rate supervisory feedback controller 1055, and an anoxic tank bCOD addition flow rate supervisory feedforward controller 1065.

MBR low-level control system 302 is comprised of at least one of an aerobic tank fluid level PI controller 765, an aerobic tank pH controller 750, an anoxic tank pH controller 755, an anoxic tank recycle line flow rate controller 770, an aerobic tank DO concentration controller 745, an anoxic tank nutritional additive concentration controller 777, an aerobic tank recycle line flow rate PI controller 771, a total MBR recycle flow rate PI controller 775, and a membrane tank MLSS concentration controller 760.

In step 445, normally, the MBR online EKF 352 performs the operations of method step 420 for the next time point operation. However, if the MBR adapted model parameters of online dynamic model 362 of MBR 30 need to be adjusted after a period of time (e.g. reporting incorrect or inconsistent values for model predicted outputs), the historical data for MBR 30 is obtained, and the method returns to step 410. Optionally, in some embodiments of step 445, the adapted model parameters are imported from online dynamic model 362 of MBR 30 into offline dynamic model 361 of MBR 30 before the method returns to step 410. This importing of the adapted model parameters from online dynamic model 362 of MBR 30 into offline dynamic model 361 of MBR 30 helps the estimated parameters converge faster when they are re-identified in the offline dynamic model 361 using MBR offline EKF 351.

FIG. 16b is a flow chart of another embodiment of a method of operating MBR 30 through monitoring and control of MBR 30 using the MBR offline and online EKFs 351 and 352 and control system 300. Steps 460-472 and 476 are monitoring steps of MBR 30 and step 474 is a controlling step of MBR 30.

As can be seen, MBR 30 is comprised of MBR offline and online EKFs 351 and 352 and control system 300. Further, MBR 30 has an aerobic tank 32, a membrane tank 33, and optionally an anoxic tank 31. Aerobic tank 32 is located upstream of membrane tank 33, and anoxic tank 31 is located either immediately upstream or downstream of said aerobic tank 32 when said anoxic tank 31 is present. In some embodiments, MBR 30 is further comprised of a mixer 41 and at least one recycle line. The recycle line may be one or both of anoxic tank recycle line 34 or aerobic tank recycle line 36.

In step 460 of a method of operating MBR 30, MBR offline EKF 351 having an offline dynamic model 361 of MBR 30 is provided, and MBR online EKF 352 having online dynamic model 362 of MBR 30 is provided. The offline and the online dynamic models 361 and 362 of MBR 30 are comprised of states, process material balances, energy balances, bio-chemical reaction kinetics, estimated parameters, and adapted model parameters. The adapted model parameters are a subset of the estimated parameters. Aerobic tank 32 and said anoxic tank 31 are modeled separately in both of the online and offline dynamic models 361 and 362 of MBR 30 when both aerobic and said anoxic tanks 32 and 31 are present.

More specifically, in some embodiments, the materials for the process material balances in the online and offline dynamic models 362 and 361 of MBR 30 are comprised of at least one of particulate inert, slowly degradable substrate, heterotrophic biomass, autotrophic biomass, decayed biomass, soluble inert, soluble readily degradable substrate, dissolved oxygen, dissolved nitrate-N (Nitrogen), dissolved ammonia-N, particulate bio-degradable-N, or bicarbonate alkalinity. Further, in some embodiments, the bio-chemical reaction kinetics in the online and offline dynamic models 362 and 361 of the MBR 30 are comprised of at least one of aerobic heterotroph, anoxic heterotroph, aerobic autotroph, decay of heterotroph, decay of autotroph, ammonification of soluble organic N, hydrolysis of organics, or hydrolysis of organic N.

In some embodiments, the estimated parameters and adapted model parameters of the offline dynamic model 361 of MBR 30 and the online dynamic model 362 of MBR 30 are comprised of at least one of heterotrophic maximum specific growth rate, anoxic/aerobic hetrotroph growth rate, anoxic/aerobic hydrolysis rate fraction, particulate hydrolysis max specific rate constant, autotrophic maximum specific growth rate, decay constant for heterotrophs, decay constant for autotrophs, yield of heterotrophic biomass, yield of autotrophic biomass, carbon content in soluble substrate, carbon content of particulate substrate, carbon content of soluble inert, carbon content of particulate nondegradable organic, mass transfer coefficient for O2 removal in aerobic tank, or mass transfer coefficient for $CO_2$ removal in anoxic tank.

In step 462, historical operation data of MBR 30 is provided. The historical operation data is comprised of historical measured input data, historical measured output data, and historical laboratory analysis data.

In some embodiments, the historical operation data of MBR 30 is comprised of at least one of raw influent pH, raw influent temperature, raw influent flow rate, raw influent TOC, raw influent TIC, added alkali flow rate, added alkali concentration, effluent flow out rate, raw influent SCOD, raw influent TCOD, raw influent readily biodegradable COD, raw influent slowly biodegradable COD, raw influent VSS, raw influent TSS, raw influent nitrate nitrogen, raw influent ammonia-nitrogen, raw influent soluble biodegradable organic nitrogen, raw influent particulate degradable organic nitrogen, raw influent inorganic inert particulate, membrane permeate flow rate, wasting sludge flow rate, anoxic tank addition biodegradable COD flow, anoxic rank reactor pH, anoxic tank Dissolved Oxygen, anoxic tank temperature, anoxic tank liquid level, anoxic tank MLVSS, anoxic tank MLSS, aerobic rank blower air flow rate, aerobic tank reactor pH, aerobic tank alkalinity, aerobic tank MLVSS, aerobic tank MLSS, aerobic tank Dissolved Oxygen, aerobic tank temperature, aerobic tank liquid level, membrane tank MLSS, membrane tank MLVSS, membrane permeate SCOD, membrane permeate TCOD, membrane permeate TOC, membrane permeate TIC, membrane permeate nitrate nitrogen, membrane permeate ammonia-nitrogen, wasting sludge MLSS, or wasting sludge MLVSS.

In step 464, estimated parameters of offline dynamic model 361 of MBR 30 are identified using MBR offline EKF 351 and the historical operation data for MBR 30.

In step 466, the estimated parameters identified in step 464 are imported from the offline dynamic model 361 of MBR 30 into the online dynamic model 362 of MBR 30.

In step 468, real time operation data for MBR 30 is provided to MBR online EKF 352. The real time operation data is comprised of real time measured input data and real time measured output data of MBR 30.

In some embodiments, the real time operation data of MBR 30 is comprised of at least one of raw influent pH, raw influent temperature, raw influent flow rate, raw influent TOC, raw influent TIC, added alkali flow rate, added alkali concentration, effluent flow out rate, raw influent SCOD, raw influent TCOD, raw influent readily biodegradable COD, raw influent slowly biodegradable COD, raw influent VSS, raw influent TSS, raw influent nitrate nitrogen, raw influent ammonia-nitrogen, raw influent soluble biodegradable organic nitrogen, raw influent particulate degradable organic nitrogen, raw influent inorganic inert particulate, membrane permeate flow rate, wasting sludge flow rate, anoxic tank addition biodegradable COD flow, anoxic rank reactor pH, anoxic tank Dissolved Oxygen, anoxic tank temperature, anoxic tank liquid level, anoxic tank MLVSS, anoxic tank MLSS, aerobic rank blower air flow rate, aerobic tank reactor pH, aerobic tank alkalinity, aerobic tank MLVSS, aerobic tank MLSS, aerobic tank Dissolved Oxygen, aerobic tank temperature, aerobic tank liquid level, membrane tank MLSS, membrane tank MLVSS, membrane permeate SCOD, membrane permeate TCOD, membrane permeate TOC, membrane permeate TIC, membrane permeate nitrate nitrogen, membrane permeate ammonia-nitrogen, wasting sludge MLSS, or wasting sludge MLVSS.

In step 470, the adapted model parameters of the online dynamic model 362 of MBR 30 are updated and the model based inferred variables of MBR 30 are estimated using the MBR online EKF 352, the online dynamic model of MBR 30, the real time measured input data of MBR 30, and the real time measured output data of MBR 30.

In some embodiments, the model based inferred variables of online dynamic model 362 of MBR 30 are comprised of at least one of the following unmeasured inputs or outputs of said MBR: raw influent alkalinity, raw influent nitrate nitrogen, raw influent ammonia-nitrogen, raw influent SCOD, raw influent TCOD, raw influent readily biodegradable COD, raw influent slowly biodegradable COD, raw influent VSS, raw influent TSS, raw influent inorganic inert particulate, anoxic rank SCOD, anoxic tank MLVSS, anoxic tank nitrate nitrogen, anoxic tank ammonia-nitrogen, anoxic tank biodegradable COD, aerobic tank SOCD, aerobic tank MLVSS, aerobic tank nitrate nitrogen, aerobic tank ammonia-nitrogen, aerobic tank biodegradable COD, membrane tank MLVSS, membrane permeate SCOD, membrane permeate biodegradable COD, membrane permeate TCOD, membrane permeate nitrate nitrogen, membrane permeate ammonia-nitrogen, wasting sludge MLVSS, COD removal rate, or nitrogen removal rate.

In step 472, one or more of the adapted model parameters of the online dynamic model 362 of MBR 30 and one or more of the model based inferred variables of MBR 30 are provided to an operator of MBR 30.

In step 474, MBR control system 300 is provided with one or more of the real time measured input data of MBR 30, real time measured output data of MBR 30, estimated parameters of the online dynamic model of MBR 30, or model based inferred variables of MBR 30. MBR control system 300 uses this information to control at least one of pH of anoxic tank 31, pH of aerobic tank 32, fluid level of aerobic tank 32, DO concentration of aerobic tank 32, MLSS concentration of membrane tank 33, bCOD addition flow rate setpoint of anoxic tank 31, at least one nutritional additive concentration of anoxic tank 31, or at least one recycle flow setpoint of MBR 30.

Wherein controlling at least one nutritional additive concentration of anoxic tank 31 prevents biomass overfeeding and starvation, wherein controlling the pH of anoxic tank 31 minimizes alkali dosing, wherein controlling the pH of aerobic tank 32 minimizes alkali dosing, wherein controlling the fluid level of aerobic tank 32 minimizes the affect of fluid perturbations of aerobic tank 32, wherein controlling the DO concentration of aerobic tank 32 ensures that a proper concentration of DO is present in aerobic tank 32, wherein controlling the MLSS concentration of membrane tank 33 maximizes membrane permeability, wherein controlling the bCOD addition flow rate setpoint of said anoxic tank 31 minimizes bCOD usage, wherein controlling at least one recycle flow setpoint of MBR 30 helps to maintain flow through MBR 30.

MBR control system 300 is comprised of an MBR supervisory control system 301 and an MBR low-level control system 302. MBR supervisory control system 301 is comprised of at least one of an aerobic tank DO supervisory controller 1040, an anoxic tank recycle flow supervisory controller 1045, or an anoxic tank bCOD addition flow rate supervisory control scheme 1035.

In some embodiments, anoxic tank bCOD addition flow supervisory control scheme 1035 of MBR 30 is comprised of anoxic tank bCOD setpoint supervisory controller 1050, anoxic tank bCOD addition flow rate supervisory feedback controller 1055, and an anoxic tank bCOD addition flow rate supervisory feedforward controller 1065. Further, in some embodiments, the aerobic tank DO supervisory controller 1040, anoxic tank recycle flow supervisory controller 1045, and anoxic tank bCOD addition flow rate supervisory control scheme 1035 work together to satisfy membrane permeate requirements on COD, nitrate, and ammonia, while minimizing aeration, recycle flow, and bCOD addition, which are established by government entities.

Further, in some embodiments, at least one of the aerobic tank DO supervisory controller 1040, anoxic tank recycle flow supervisory controller 1045, or anoxic tank bCOD addition flow rate supervisory control scheme 1035 uses at least one of an estimated parameter of online dynamic model 362 of MBR 30 or a model based inferred variable of MBR 30.

Additionally, in some embodiments, MBR low-level control system 302 is comprised of at least one of an aerobic tank fluid level PI controller 765, an aerobic tank pH controller 750, an anoxic tank pH controller 755, an anoxic tank recycle line flow rate controller 770, an aerobic tank DO concentration controller 745, an anoxic tank nutritional additive concentration controller 777, an aerobic tank recycle line flow rate PI controller 771, a total MBR recycle flow rate PI controller 775, or a membrane tank MLSS concentration controller 760.

In some embodiments, membrane tank MLSS concentration controller 760 uses a model based inferred variable of said MBR. In some embodiments, the model based inferred variable is MLVSS concentration or MLSS concentration.

In step 476, the MBR operator, or an automated system such as computer 1071, decides whether it is necessary to adjust the adapted model parameters of the online dynamic model 362 of MBR 30 (e.g. reporting incorrect or inconsistent values for model predicted outputs or model based inferred variables). If it is not necessary to adjust the adapted model parameters, the method returns to step 468.

If it is necessary to adjust the adapted model parameters, the operator or computer 1071 can choose to use one or both of an online EKF approach or an offline EKF approach to update the adapted model parameters of the online dynamic model 362. Traditionally, the offline EKF approach is only used periodically, in some embodiments about every few weeks or months. The online EKF approach is used more frequently, in some embodiments as frequently as about every 30 minutes.

In some embodiments, the decision of whether or not to adjust the adapted model parameters is determined by elapsed time, such as an adjustment of the adapted model parameters using the online EKF approach is performed about every 30 minutes to once a day, and an adjustment of the adapted model parameters using the offline EKF approach is performed about every few weeks to few months.

In the online EKF approach, model predicted outputs of MBR 30 are calculated using MBR online EKF 352, online dynamic model 362 of MBR 30, real time measured input data of MBR 30, and real time measured output data of MBR 30. The measured output data of MBR 30 and the model predicted outputs of MBR 30 are then compared, and the adapted model parameters of online dynamic model 362 of MBR 30 are updated such that the real time measured output data of MBR 30 substantially correspond with the model predicted outputs of MBR 30.

In the offline EKF approach, the estimated parameters of the offline dynamic model 361 of MBR 30 are re-identified using the MBR offline EKF 351 and the historic operation data for MBR 30. The estimated parameters of offline dynamic model 361, which contain the updated adapted model parameters as a subset, are then imported into the online dynamic model 362.

In some embodiments of the offline EKF approach, the adapted model parameters of the online dynamic model 362 of MBR 30 are imported into the offline dynamic model 361 of MBR 30 before the estimated parameters of the offline dynamic model 361 of MBR 30 are re-identified. This allows the estimated parameters of the offline dynamic model 361 to converge faster when they are re-identified by MBR offline EKF 351.

After step 476, the method returns to step 468 to provide real time operation data of MBR 30 for the next time point to MBR online EKF 352.

In some embodiments, at least one of the estimated parameters of offline dynamic model 361 of MBR 30 and model based inferred variables of online dynamic model 362 of said MBR 30 are estimated with confidence intervals.

Further, in some embodiments, the adapted model parameters of online dynamic model 362 of MBR 30 are tuned using different weights for online measurements and prior knowledge of measurement accuracy. Additionally, in some embodiments, limits are applied to one or more of the estimated parameters and adapted model parameters, and constraints are applied to one or more of the model based inferred variables.

It is contemplated that the method of operating MBR 30 includes variations of the methods depicted in FIGS. 16*a-b*. Some embodiments of such methods may be arrived at by substituting steps or underlying details of one of 16*a* or 16*b*, and using the steps or underlying details in the other of 16*a* or 16*b*.

It is contemplated that in some embodiments, at least one of monitoring MBR 30 or controlling MBR 30 is performed using a computer.

While online monitoring is very useful in itself to maintain a good understanding of the process operation in the presence of significant variations in AD 20 and MBR 30. The online monitoring solution discussed above for AD 20 and MBR 30 can be used in conjunction with a supervisory control solution to improve the stability, robustness and operational efficiency of the AD 20 and MBR 30 processes. Accordingly, it is contemplated that one or more embodiments of control system 200 of AD 20 may include one or more of the following controls shown in FIG. 21-27.

Good pH control in AD reactor 24 helps to ensure its stability. Poor pH control can easily lead to a cascading instability where pH drop leads to methanogenesis inhibition, leading to further pH drop and eventual biomass deactivation and washout. The pH in AD reactor 24 is impacted by continuous unknown changes in the feed as well as variations in biomass activity in the digester.

Figure 17A:
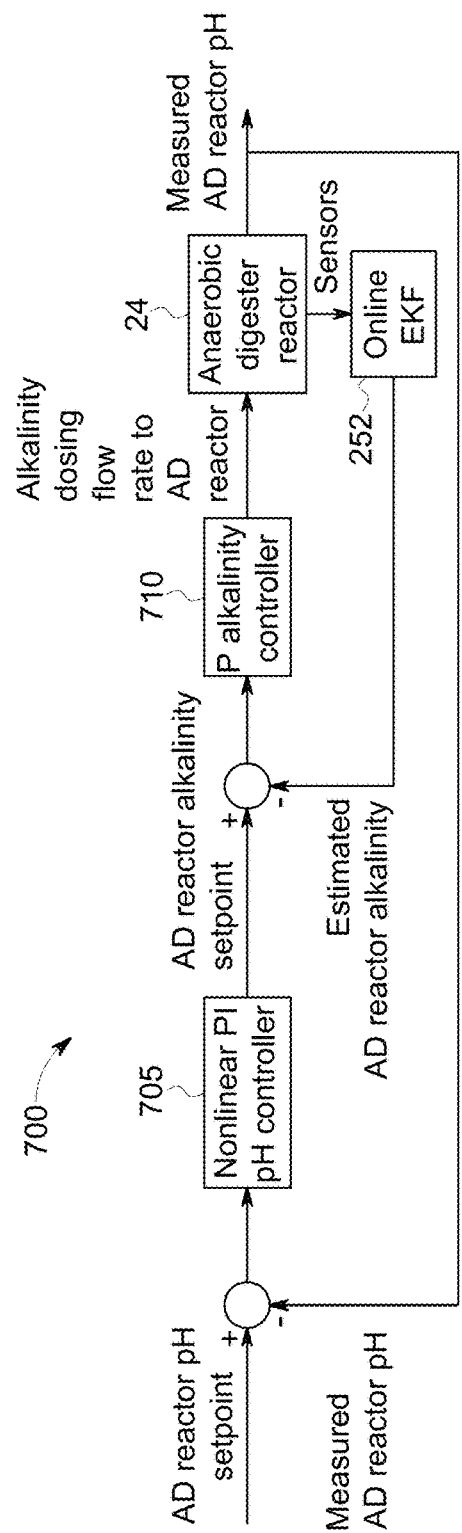
FIG. 17a is a block diagram depicting AD reactor pH supervisory controller for AD reactor with a nonlinear PI control and an alkalinity control in cascade structure in accordance with aspects of the present technique.

FIG. 17*a* depicts AD reactor pH supervisory controller 700 for AD reactor 24 with a nonlinear PI control and an alkalinity control in cascade structure. AD reactor pH supervisory controller 700 is comprised of an AD reactor nonlinear Proportional-Integral (PI) pH controller 705, AD reactor Proportional (P) alkalinity controller 710, AD reactor 24, and AD online EKF 252. AD reactor nonlinear PI pH controller 705 is provided with the difference between a user selected pH setpoint for AD reactor 24 and the measured pH value for AD reactor 24. AD reactor nonlinear PI pH controller 705 then outputs the AD reactor alkalinity setpoint. AD reactor P alkalinity controller 710 is provided with the difference between the AD reactor alkalinity setpoint from AD reactor nonlinear PI pH controller 705 and the estimated alkalinity of AD reactor 24. The estimated alkalinity of AD reactor 24 is ascertained via estimation by the AD online EKF 252 of AD 20. In some embodiments, AD online EKF 252 may also enable feedforward control action to maintain the alkalinity of AD reactor 24. AD reactor P alkalinity controller 710 adjusts the alkalinity dosing flow rate to AD reactor 24 based on the AD alkalinity setpoint and estimated alkalinity of AD reactor 24 from AD online EKF 252. It is understood that alternatively an operator may also manually manipulate the AD reactor alkalinity setpoint by an operator on the operator control panel 1070.

Figure 17B:
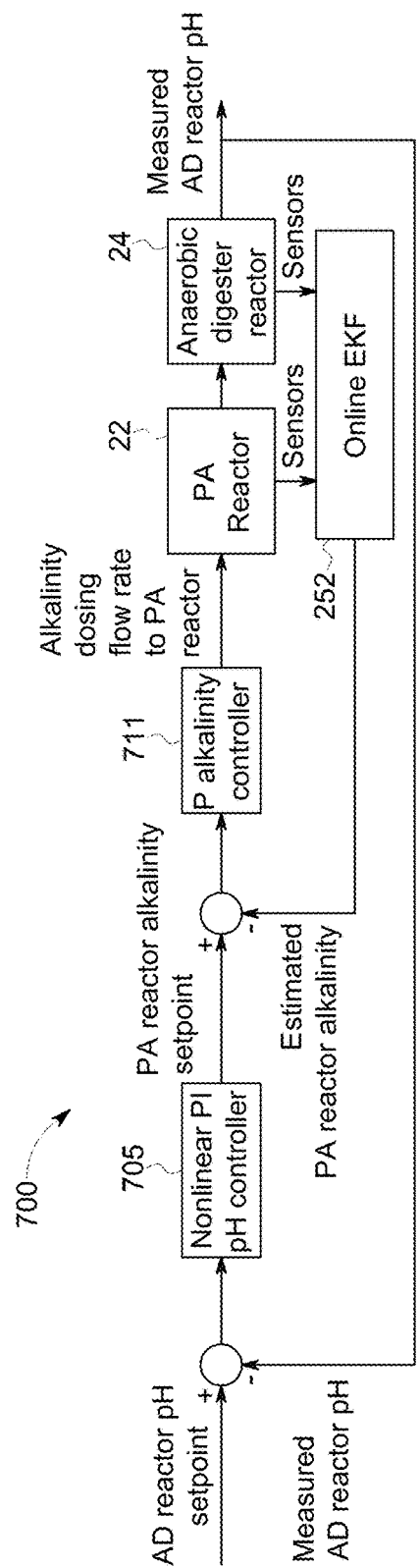
FIG. 17b is a block diagram depicting AD reactor pH supervisory controller for AD reactor with a nonlinear PI control and an alkalinity control in cascade structure in accordance with aspects of the present technique.

FIG. 17*b* depicts another embodiment of AD reactor pH supervisory controller 700 that controls the pH of AD reactor 24 with a nonlinear PI control and an alkalinity control in cascade structure. This embodiment can be used when PA reactor pH supervisory controller 701 is not present. In this embodiment, AD reactor pH supervisory controller 700 is comprised of an AD reactor nonlinear PI pH controller 705, PA reactor P alkalinity controller 711, PA reactor 22, AD reactor 24, and the AD online EKF 252 of AD 20. In operation, AD reactor nonlinear PI pH controller 705 is provided with the difference between a user selected pH setpoint for AD reactor 24 and the measured pH value for AD reactor 24. AD reactor nonlinear PI pH controller 705 then outputs the PA reactor alkalinity setpoint. PA reactor P alkalinity controller 711 is provided with the difference between the PA reactor alkalinity setpoint from AD reactor nonlinear PI pH controller 705 and the estimated alkalinity of PA reactor 22. The estimated alkalinity of PA reactor 22 is ascertained via estimation by the AD online EKF 252 of AD 20. PA reactor P alkalinity controller 711 adjusts the alkalinity dosing flow rate to PA reactor 22 based on the PA reactor alkalinity setpoint and the estimated PA reactor alkalinity. This control structure has less components but is still able to respond fast to disturbances coming into the AD 20. The AD online EKF 252 of AD 20 makes this cascade control possible by providing real-time estimate of the alkalinity of PA reactor 22. It is understood that alternatively, an operator may also manually manipulate the PA reactor alkalinity setpoint by an operator on the operator control panel 1070. In some embodiments, AD online EKF 252 may enable feedforward control action to maintain the alkalinity of PA reactor 22 based on inferred variations in the raw influent.

Figure 18:
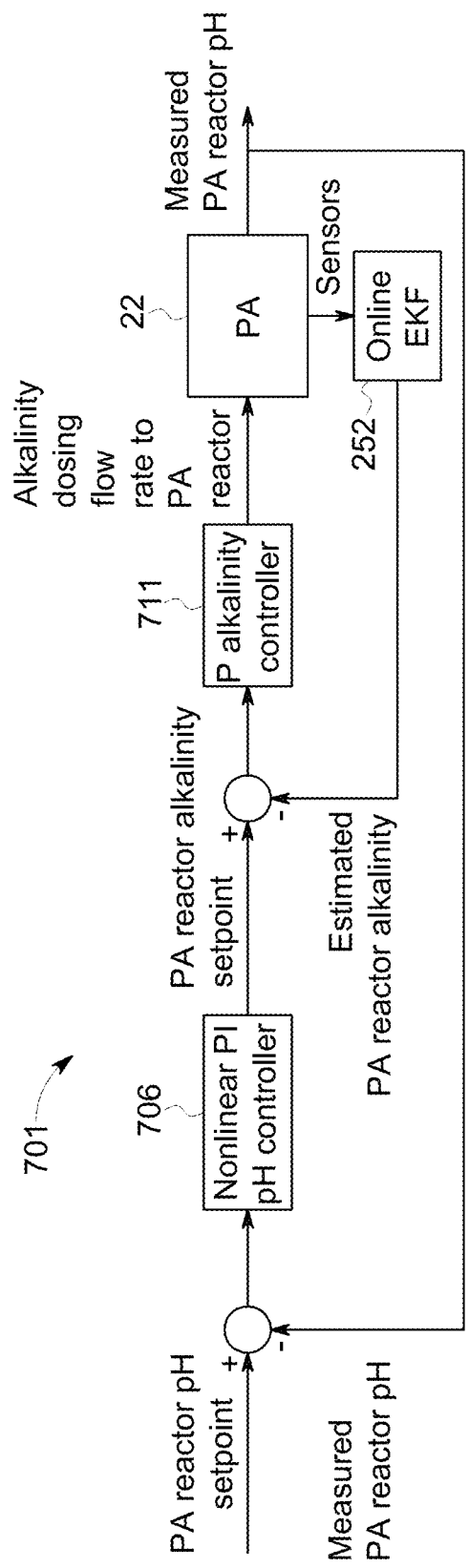
FIG. 18 is a block diagram depicting PA reactor pH supervisory controller for PA reactor with a nonlinear PI control and an alkalinity control in cascade structure in accordance with aspects of the present technique.

FIG. 18 depicts PA reactor pH supervisory controller 701 for PA reactor 22 with a nonlinear PI control and an alkalinity control in cascade structure. The PA reactor pH supervisory controller 701 is comprised of PA reactor nonlinear Proportional-Integral (PI) pH controller 706, PA reactor Proportional (P) alkalinity controller 711, PA reactor 22, and the AD online EKF 252. PA reactor nonlinear PI pH controller 706 is provided with the difference between a user selected pH setpoint for PA reactor 22 and the measured pH value for PA reactor 22. PA reactor nonlinear PI pH controller 706 then outputs the PA reactor alkalinity setpoint. PA reactor P alkalinity controller 711 is provided with the difference between the PA reactor alkalinity setpoint from PA reactor nonlinear PI pH controller 706 and the estimated alkalinity of PA reactor 22. The estimated alkalinity of PA reactor 22 is ascertained via estimation by the AD online EKF 252 of AD 20. In some embodiments, AD online EKF 252 may enable feed forward control action to maintain the alkalinity of PA reactor 22. PA reactor P alkalinity controller 711 adjusts the alkalinity dosing flow rate to PA reactor 22 based on the AD alkalinity setpoint and estimated alkalinity flow rate to PA reactor 22. It is understood that alternatively an operator may also manually manipulate the PA reactor alkalinity setpoint on the operator control panel 1070.

The pH controllers described above in FIGS. 17-18 for AD reactor 24 and PA reactor 22 improves pH control by using a nonlinear transformation on the controlled output pH, and by using a cascaded control structure. The nonlinear transformation that is applied to the controlled variable pH, allows for better handling of the nonlinear relation between pH and the molar quantities of the species inside AD reactor 24 and PA reactor 22, such as the interaction between bicarbonate and VFA alkalinity. The cascade control loop allows for separation of fast and slow dynamics on the alkalinity balance inside the reactors and therefore is able to take earlier control actions in the face of disturbances.

As mentioned earlier, a concern in digester operation is the presence of a toxic/inhibitory ingredient in the wastewater feed that leads to reduction in methanogenesis activity, which if significant and un-mitigated can lead to biomass deactivation and washout. The online EKF discussed above provides the ability to detect such an inhibition online and early.

Figure 19A:
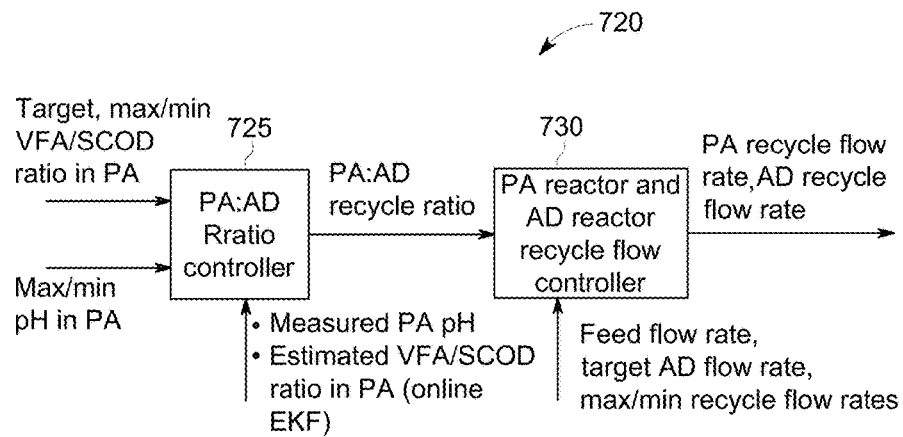
FIG. 19a is a block diagram depicting a PA:AD overall recycle flow ratio supervisory controller in accordance with aspects of the present technique.
Figure 19B:
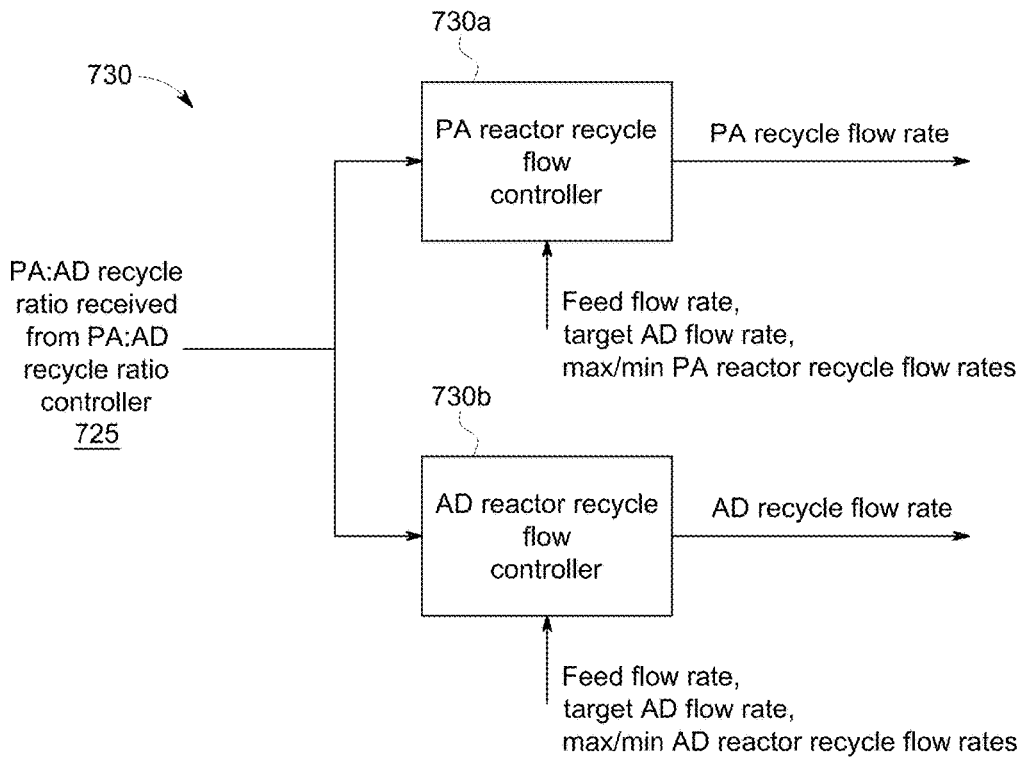
FIG. 19b is a block diagram depicting a PA reactor and AD reactor recycle flow rate controller in accordance with aspects of the present technique.

FIG. 19a-b depict an PA:AD overall recycle flow ratio supervisory controller 720 for the coordination of PA reactor 22 and AD reactor 24 for acidogenesis and methanation. PA:AD overall recycle flow ratio supervisory controller 720 is comprised of PA:AD recycle ratio controller 725 and PA reactor and AD reactor recycle flow rate controller 730. PA:AD recycle ratio controller 725 is provided the measured pH of PA reactor 22, the maximum pH setpoint of PA reactor 22, the minimum pH setpoint of PA reactor 22, the estimated VFA/SCOD of PA reactor 22, target VFA/SCOD of PA reactor 22, maximum VFA/SCOD setpoint of PA reactor 22, and minimum VFA/SCOD setpoint of PA reactor 22. The contents of PA:AD recycle ratio controller 725 is described in FIG. 20. PA:AD recycle ratio controller 725 then outputs the PA:AD Rratio (Recycle ratio) to PA reactor and AD reactor recycle flow rate controller 730, which sets the flow rates of PA recycle pump 28 and AD recycle pump 29 of AD 20 based on the PA:AD Rratio, AD feed flow rate, target AD flow rate, maximum/minimum recycle flow rates. It is contemplated that in some embodiments, PA reactor and AD reactor recycle flow rate controller 730 can be one controller, as is shown in FIG. 19a. Further, it is contemplated that in other embodiments, PA reactor and AD reactor recycle flow rate controller 730 can be comprised of an individual PA reactor recycle flow rate controller 730a and an AD reactor recycle flow rate controller 730b which set the flow rates of PA recycle pump 28 and AD recycle pump 29 of AD 20 such as is shown in FIG. 19b.

Figure 20:
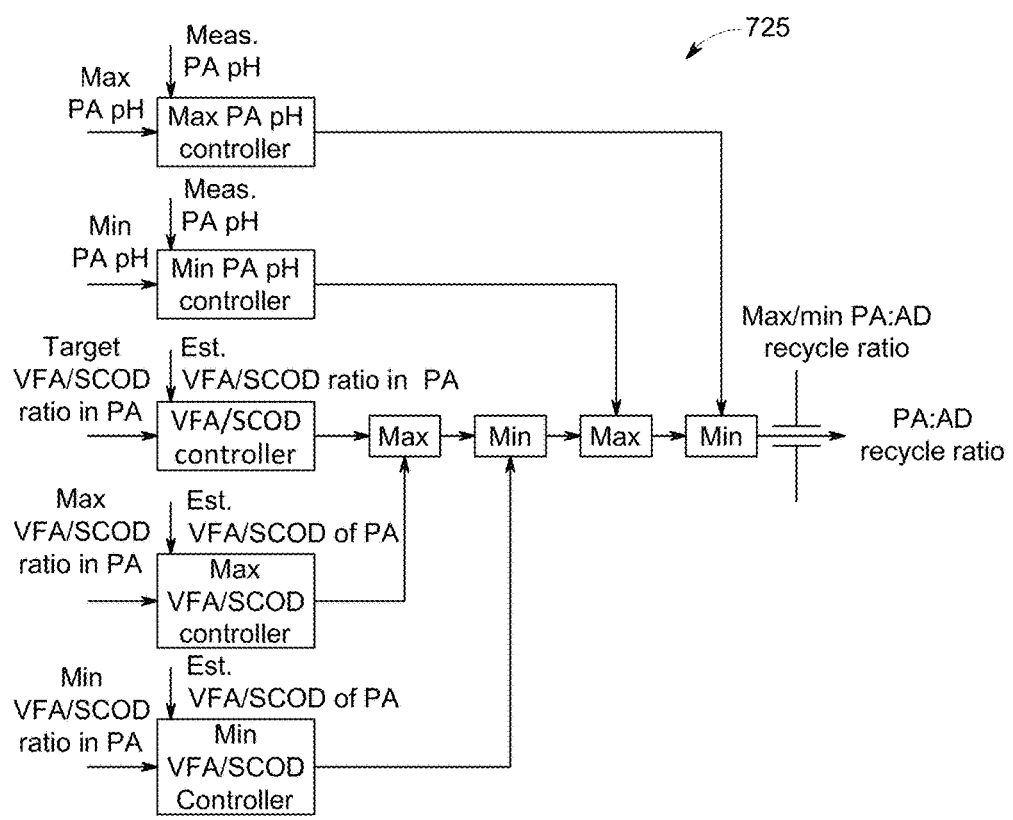
FIG. 20 is a block diagram depicting a PA:AD Recycle Ratio controller in accordance with aspects of the present technique.

FIG. 20 depicts the PA:AD Recycle Ratio controller 725. PA:AD Recycle Ratio controller 725 is comprised of multiple conventional controllers (e.g., PI or PID controller) working simultaneously, and passing their outputs through signal selection operations, i.e., min/max selection functions, and then through the constraints of PA:AD flow ratio range limits, which and then forms the controller outputs. The arrangement of the min/max selection operations makes the final output signal capable of satisfying all the desired limits of the input signals to the controller.

As mentioned earlier, another concern in digester operation is biomass deactivation and washout. The AD online EKF 252 discussed above provides the ability to detect the biomass concentration within AD reactor 24 and add additional biomass if necessary.

Figure 21:
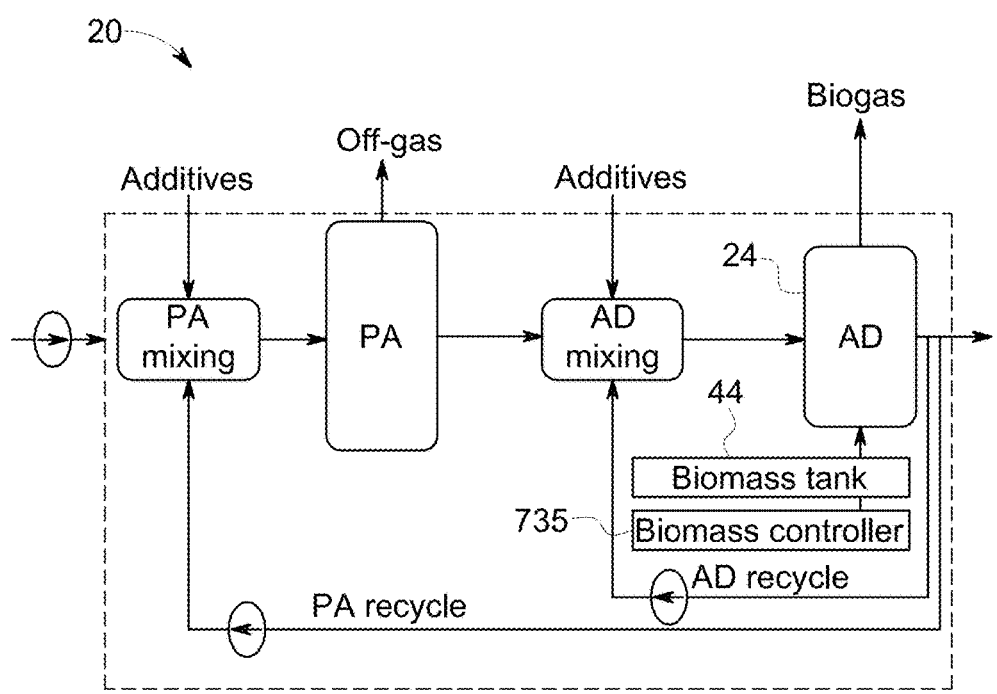
FIG. 21 is a block diagram depicting an implementation of AD reactor biomass concentration controller in accordance with aspects of the present technique.
Figure 22:
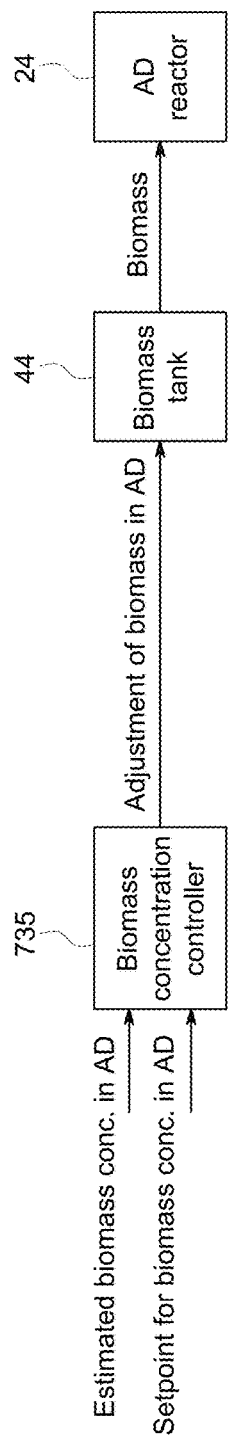
FIG. 22 is a block diagram depicting an AD reactor biomass concentration controller in accordance with aspects of the present technique.

FIG. 21 depicts a control scheme for regulating the biomass concentration in AD reactor 24 of AD 20. If additional biomass is required in AD reactor 24, the additional biomass is provided by biomass tank 44, which is controlled by AD reactor biomass concentration controller 735. A block diagram of AD reactor biomass concentration controller 735 is detailed in FIG. 22. As can be seen, AD reactor biomass concentration controller 735 is provided with the estimated biomass concentration in AD reactor 24 by AD online EKF 252 of AD 20, and the operator defined setpoint for biomass in AD reactor 24 on the operator control panel 1070. The AD online EKF 252 of AD 20 ascertains the concentration of biomass in AD reactor 24 by detecting and tracking biomass inhibiting events. AD reactor biomass concentration controller 735 then determines whether an adjustment is required of the concentration of biomass in AD reactor 24 by examining whether the estimated biomass concentration in AD reactor 24 is less than the operator defined setpoint. If the operator defined setpoint for biomass concentration in AD reactor 24 is greater than the estimated biomass concentration in AD reactor 24, AD reactor biomass concentration controller 735 instructs biomass tank 44 to add biomass to AD reactor 24 such that the biomass concentration in AD reactor 24 substantially corresponds with the operator defined setpoint for biomass concentration in AD reactor 24.

Figure 23:
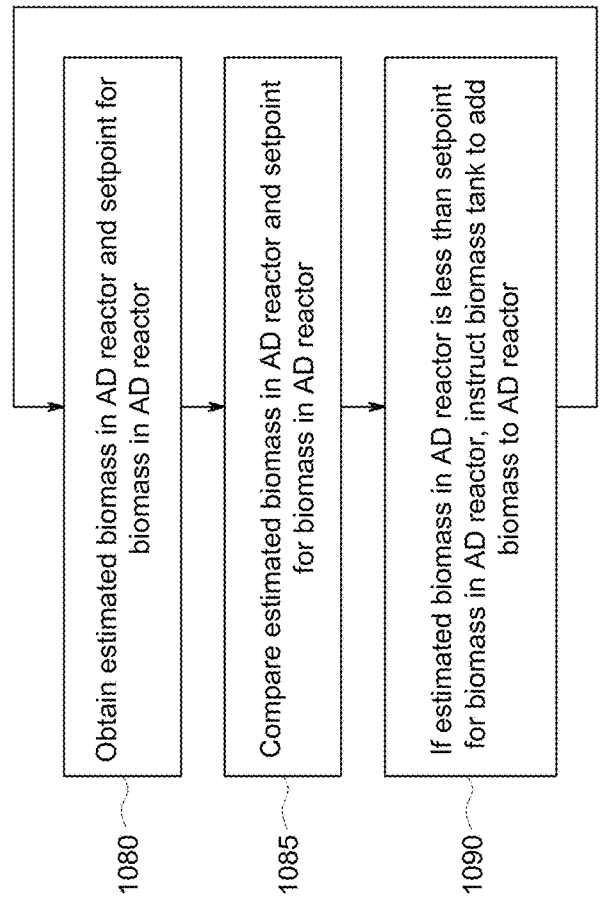
FIG. 23 is a flow chart depicting the operations taking place within AD reactor biomass concentration controller in accordance with aspects of the present technique.

FIG. 23 is a flow chart detailing the operations taking place within AD reactor biomass concentration controller 735. In step 1080 the estimated concentration of biomass in AD reactor 24 is obtained from the AD online EKF 252 of AD 20 and the setpoint for the concentration of biomass in AD reactor 24 is obtained from the operator control panel 1070. Following step 1080, in step 1085 the estimated concentration of biomass in AD reactor 24 is compared with the setpoint for the concentration of biomass in AD reactor 24. Following step 1085, in step 1090, if the estimated concentration of biomass in AD reactor 24 is less than the setpoint the concentration of biomass in AD reactor 24, AD reactor biomass concentration controller 735 instructs biomass tank 44 to add biomass to AD reactor 24. Following step 1090, AD reactor biomass concentration controller 735 returns to step 1080 and repeats the operations in steps 1080-1090.

Figure 24:
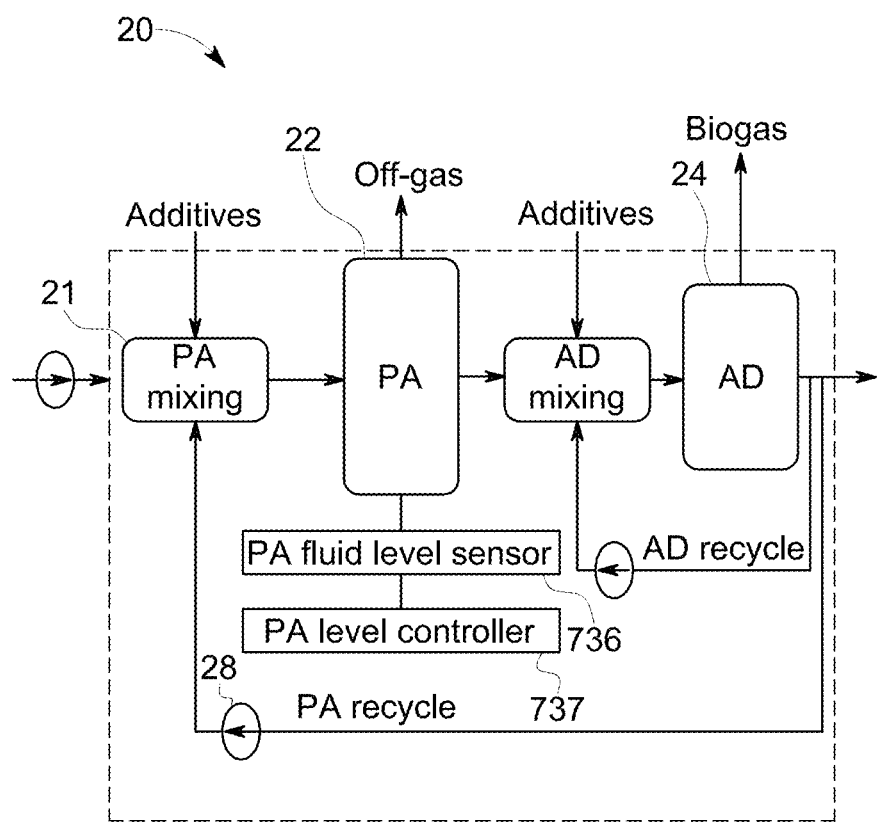
FIG. 24 is a block diagram depicting an implementation of PA fluid level controller in accordance with aspects of the present technique.

Further, another consideration is adjusting the fluid level in PA reactor 22 to absorb transient perturbations to the plant, rather than keeping the fluid level in PA reactor 22 at a constant setpoint. FIG. 24 depicts a control scheme for the fluid level within PA reactor 22 in which PA fluid level sensor 736 senses the level of fluid with PA reactor 22, PA fluid level sensor 736 passes the level to PA fluid level controller 737, which make any necessary adjustment to the flow rate of PA recycle pump 28 to return the fluid level within PA reactor 22 to an acceptable level by increasing or decreasing the amount of water recycled from AD reactor 24 to PA reactor mixing stage 21, which is immediately upstream of PA reactor 22, or directly to PA reactor 22 if PA reactor mixing stage 21 is not present.

Figure 25:
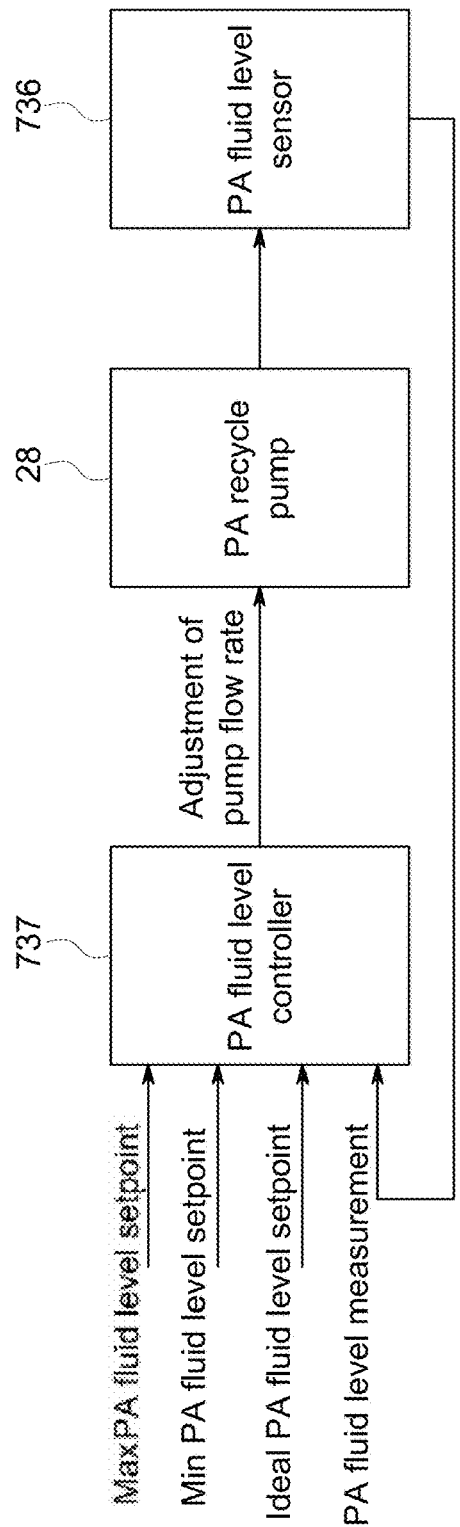
FIG. 25 is a block diagram depicting a PA fluid level controller in accordance with aspects of the present technique.

A block diagram of PA fluid level controller 737 is detailed in FIG. 25. As can be seen, PA fluid level controller 737 is provided with the maximum PA fluid level setpoint, minimum PA fluid level setpoint, ideal PA fluid level setpoint, and PA fluid level measurement. The setpoints are provided by the operator on the operator control panel 1070. The PA fluid level measurement is provided by PA fluid level sensor 736. PA fluid level controller 737 then determines whether an adjustment of PA recycle pump 28 is required. PA fluid level sensor 736 then reports any changes in fluid level of PA reactor 22 to PA fluid level controller 737.

Figure 26:
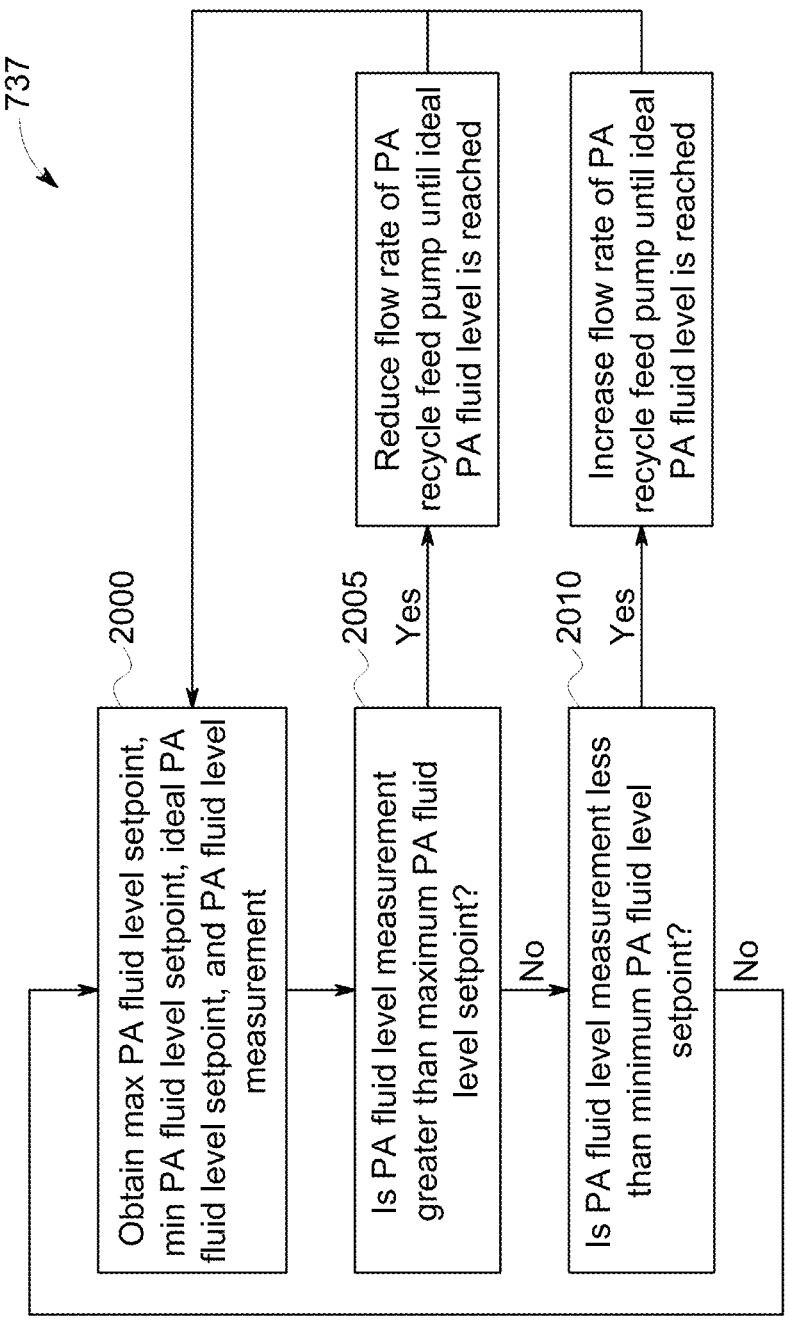
FIG. 26 is a flow chart depicting the operations taking place within PA fluid level controller in accordance with aspects of the present technique.

FIG. 26 is a flow chart detailing the operations taking place within PA fluid level controller 737. In step 2000, PA fluid level controller 737 obtains the maximum PA fluid level setpoint, minimum PA fluid level setpoint, ideal PA fluid level setpoint, and PA fluid level measurement. In step 2005, the PA fluid level measurement is compared to the maximum PA fluid level setpoint. If the PA fluid level measurement is less than the maximum PA fluid level setpoint, the program advances to step 2010. However, if the PA fluid level measurement is greater than the maximum PA fluid level setpoint, PA fluid level controller 737 reduces the flow rate of the PA recycle pump 28 until the PA fluid level sensor 736 informs the PA fluid level controller 737 that the PA fluid level substantially corresponds to the ideal PA fluid level setpoint and then proceeds back to step 2000.

In step 2010, the PA fluid level measurement is compared to the minimum PA fluid level setpoint. If the PA fluid level measurement is not less than the minimum PA fluid level setpoint, the program returns to step 2000. However, if the PA fluid level measurement is less than the minimum PA fluid level setpoint, PA fluid level controller 737 increases the flow rate of the PA recycle pump 28 until the PA fluid level sensor 736 informs the PA fluid level controller 737 that the PA fluid level substantially corresponds to the ideal PA fluid level setpoint and then proceeds back to step 2000.

Figure 27:
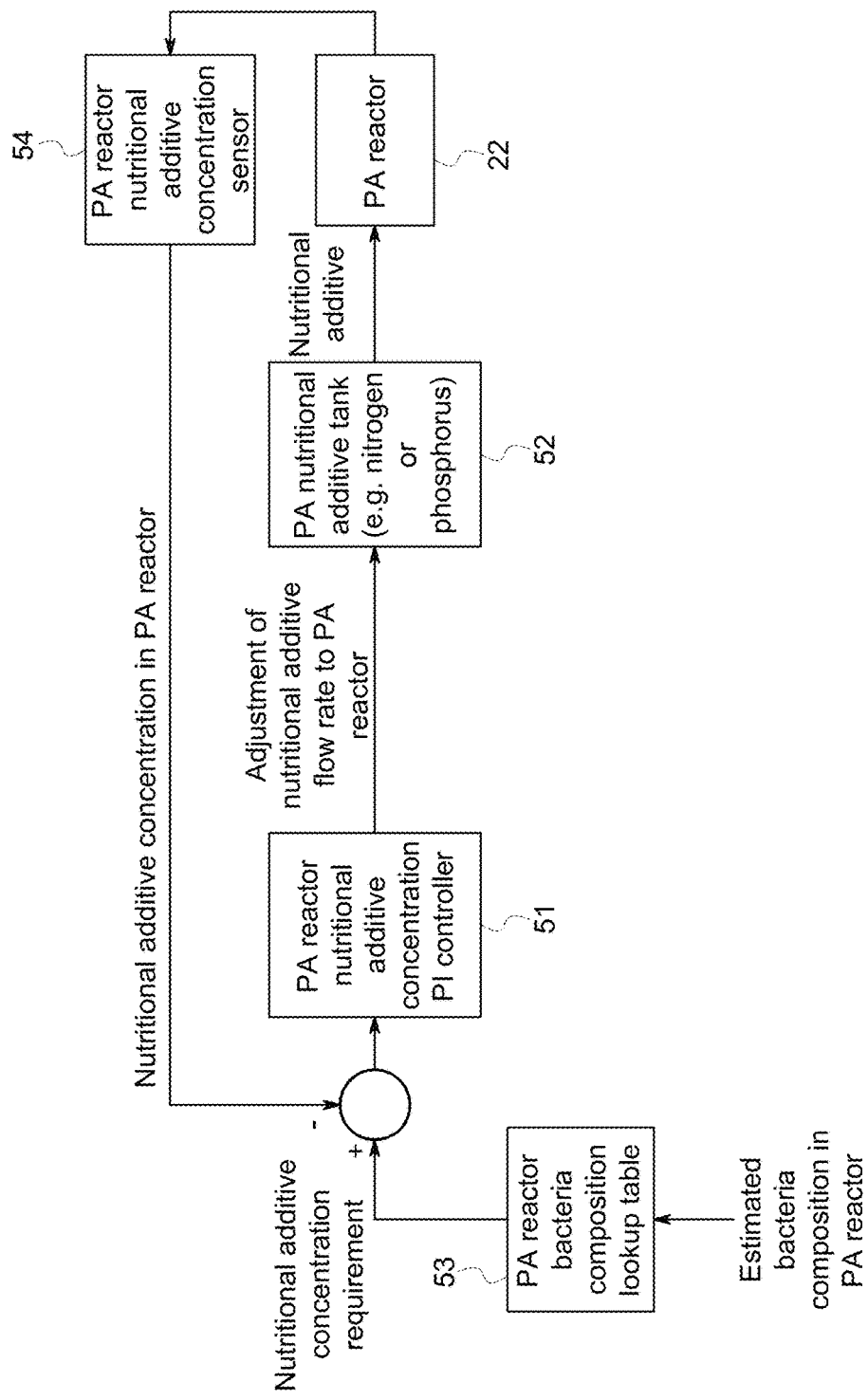
FIG. 27 is a block diagram depicting a PA reactor nutritional additive concentration controller in accordance with aspects of the present technique.

FIG. 27 shows a scheme for regulating the nutrient concentration within some embodiments of PA reactor 22 of AD 20. It is contemplated in some embodiments of AD 20, the amount and type of nutritional additives, provided to PA reactor 22 will be determined by the estimated composition of the bacteria contained within PA reactor 22. It is contemplated that in some embodiments, a PA reactor nutritional additive concentration controller 51 and PA reactor nutritional additive tank 52 will be provided for each nutrient of interest for PA reactor 22. Further, it is contemplated that in some embodiments, all of the additive nutrients for PA reactor 22 are combined in a single PA reactor nutritional additive tank 52, accordingly, in those embodiments, only one PA reactor nutritional additive concentration controller 51 and PA reactor nutritional additive tank 52 will be present for AD 20.

In one embodiment, PA reactor nutritional additive concentration controller 51 is a PI controller. The nutritional additives may include, but are not limited to, nitrogen and phosphorus. The composition of bacteria in PA reactor 22 will be estimated by AD online EKF 252. A PA reactor bacteria composition lookup table 53 is used to ascertain the nutritional additive concentration requirement for the composition of bacteria within PA reactor 22 and output the concentration requirement for the specific nutritional additive of interest. The concentration of the nutritional additive of interest within PA reactor 22 is ascertained via direct measurement via PA reactor additive concentration sensor 54 contained within PA reactor 22, or AD online EKF 252. The concentration of the nutritional additive of interest present within PA reactor 22 is subtracted from the concentration of the nutritional additive requirement to determine if a deficiency exists for the nutrient of interest and the difference is provided to PA reactor nutritional additive concentration controller 51, which adjusts the flow rate of the nutritional additive of interest flowing from PA reactor nutritional additive tank 52 into PA reactor 22.

Accordingly, if a nutrient deficiency exists, nutritional additives are provided to PA reactor 22 until the nutrient deficiency is rectified. Accordingly, the flow rates of the various nutritional additives of interest provided to PA reactor 22 from the various PA reactor nutritional additive tanks 52 are individually adjusted based on the amount of each species of bacteria present within each of PA reactor 22 and nutrient concentration present within PA reactor 22, so as not to overfeed or starve the bacteria.

In another embodiment in which all of the additive nutrients for PA reactor 22 are combined in a single PA reactor nutritional additive tank 52, the composition of bacteria in PA reactor 22 will be estimated by AD online EKF 252. A PA reactor bacteria composition lookup table 53 is used to ascertain the nutritional additive concentration requirement for the composition of bacteria within PA reactor 22 and output the concentration requirement for the nutritional additives of interest. The concentration of the nutritional additives of interest within PA reactor 22 is ascertained via direct measurement via PA reactor additive concentration sensor 54 contained within PA reactor 22, or AD online EKF 252. The concentration of the nutritional additives of interest present within PA reactor 22 is subtracted from the concentration of the nutritional additive requirement to determine if a deficiency exists for the nutrients of interest and the difference is provided to PA reactor nutritional additive concentration controller 51, which adjusts the flow rate of the nutritional additives of interest flowing from PA reactor nutritional additive tank 52 into PA reactor 22.

Accordingly, if a nutrient deficiency exists, nutritional additives are provided to PA reactor 22 until the nutrient deficiency is rectified. Accordingly, the flow rate of the nutritional additives of interest provided to PA reactor 22 is adjusted based on the amount of each species of bacteria present within each of PA reactor 22 and nutrient concentration present within PA reactor 22, so as not to overfeed or starve the bacteria.

Figure 28:
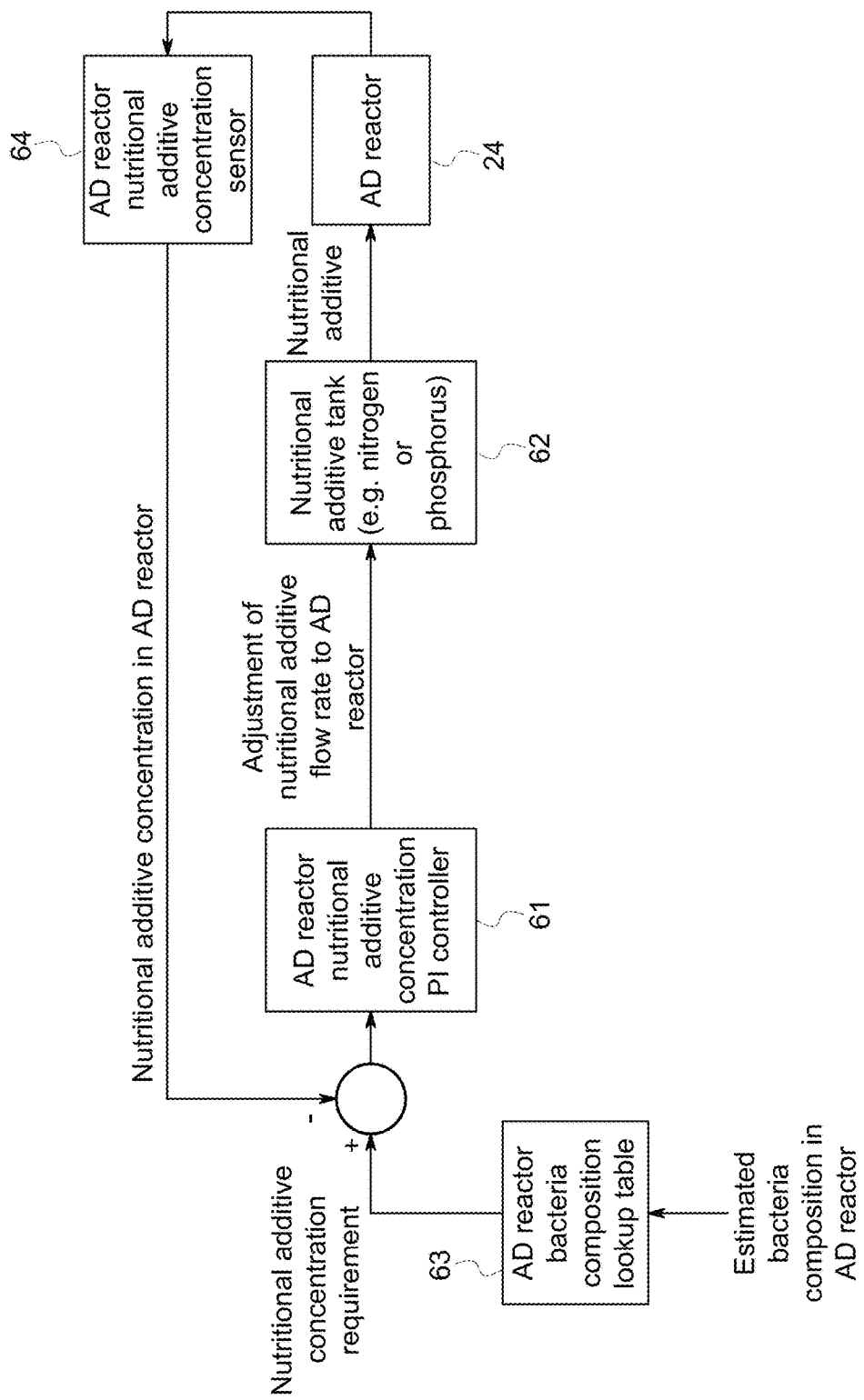
FIG. 28 is a block diagram depicting an AD reactor nutritional additive concentration controller in accordance with aspects of the present technique.

FIG. 28 shows a scheme for regulating the nutrient concentration within some embodiments of AD reactor 24 of AD 20. It is contemplated in some embodiments of AD 20, the amount and type of nutritional additives, provided to AD reactor 24 will be determined by the estimated composition of the bacteria contained within AD reactor 24. It is contemplated that in some embodiments, a AD reactor nutritional additive concentration controller 61 and AD reactor nutritional additive tank 62 will be provided for each nutrient of interest for AD reactor 24. Further, it is contemplated that in some embodiments, all of the additive nutrients for AD reactor 24 are combined in a single AD reactor nutritional additive tank 62, accordingly, in those embodiments, only one AD reactor nutritional additive concentration controller 61 and AD reactor nutritional additive tank 62 will be present for AD 20.

In one embodiment, AD reactor nutritional additive concentration controller 61 is a PI controller. The nutritional additives may include, but are not limited to, nitrogen and phosphorus. The composition of bacteria in AD reactor 24 will be estimated by AD online EKF 252. An AD reactor bacteria composition lookup table 63 is used to ascertain the nutritional additive concentration requirement for the composition of bacteria within AD reactor 24 and output the concentration requirement for the specific nutritional additive of interest. The concentration of the nutritional additive of interest within AD reactor 24 is ascertained via direct measurement via AD reactor additive concentration sensor 64 contained within AD reactor 24, or AD online EKF 252. The concentration of the nutritional additive of interest present within AD reactor 24 is subtracted from the concentration of the nutritional additive requirement to determine if a deficiency exists for the nutrient of interest and the difference is provided to AD reactor nutritional additive concentration controller 61, which adjusts the flow rate of the nutritional additive of interest flowing from AD reactor nutritional additive tank 62 into AD reactor 24.

Accordingly, if a nutrient deficiency exists, nutritional additives are provided to AD reactor 24 until the nutrient deficiency is rectified. Accordingly, the flow rates of the various nutritional additives of interest provided to AD reactor 24 from the various AD reactor nutritional additive tanks 62 are individually adjusted based on the amount of each species of bacteria present within each of AD reactor 24 and nutrient concentration present within AD reactor 24, so as not to overfeed or starve the bacteria.

In another embodiment in which all of the additive nutrients for AD reactor 24 are combined in a single AD reactor nutritional additive tank 62, the composition of bacteria in AD reactor 24 will be estimated by AD online EKF 252. An AD reactor bacteria composition lookup table 63 is used to ascertain the nutritional additive concentration requirement for the composition of bacteria within AD reactor 24 and output the concentration requirement for the nutritional additives of interest. The concentration of the nutritional additives of interest within AD reactor 24 is ascertained via direct measurement via AD reactor additive concentration sensor 64 contained within AD reactor 24, or AD online EKF 252. The concentration of the nutritional additives of interest present within AD reactor 24 is subtracted from the concentration of the nutritional additive requirement to determine if a deficiency exists for the nutrients of interest and the difference is provided to AD reactor nutritional additive concentration controller 61, which adjusts the flow rate of the nutritional additives of interest flowing from AD reactor nutritional additive tank 62 into AD reactor 24.

Accordingly, if a nutrient deficiency exists, nutritional additives are provided to AD reactor 24 until the nutrient deficiency is rectified. Accordingly, the flow rate of the nutritional additives of interest provided to AD reactor 24 is adjusted based on the amount of each species of bacteria present within each of AD reactor 24 and nutrient concentration present within AD reactor 24, so as not to overfeed or starve the bacteria.

As was previously stated, while online monitoring is very useful in itself to maintain a good understanding of the process operation in the presence of significant variations in AD 20 and MBR 30. The online monitoring solution discussed above for AD 20 and MBR 30 can be used in conjunction with a supervisory control solution to improve the stability, robustness and operational efficiency of the AD 20 and MBR 30 processes. Accordingly, it is contemplated that one or more embodiments of MBR control system 300 of MBR 30 may include one or more of the controls described below.

Figure 29:
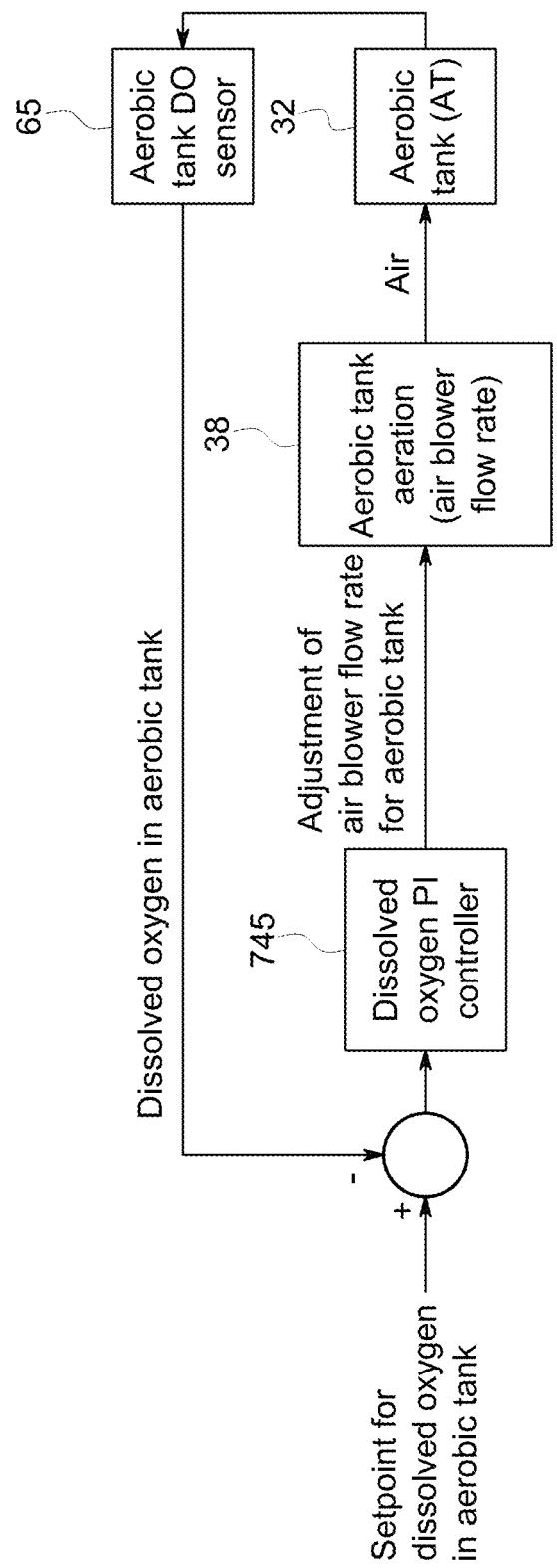
FIG. 29 is a block diagram depicting an aerobic tank DO concentration controller in accordance with aspects of the present technique.
Figure 30:
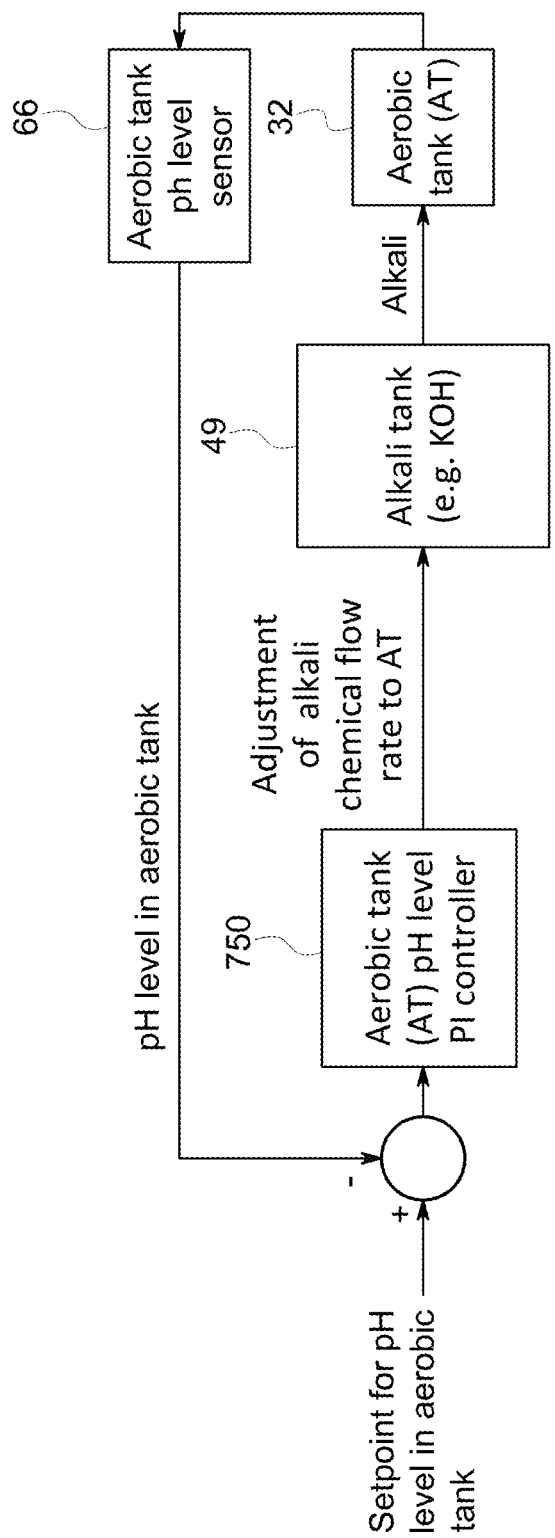
FIG. 30 is a block diagram depicting an aerobic tank pH controller in accordance with aspects of the present technique.
Figure 31:
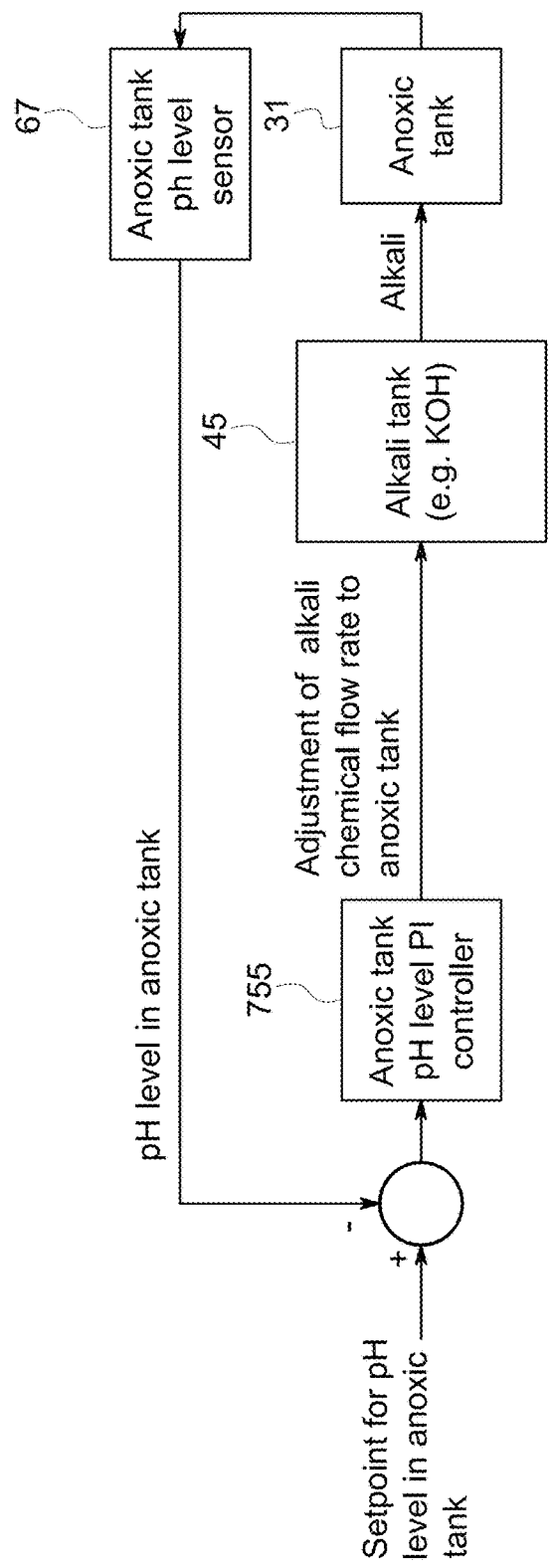
FIG. 31 is a block diagram depicting an anoxic tank pH controller in accordance with aspects of the present technique.
Figure 32A:
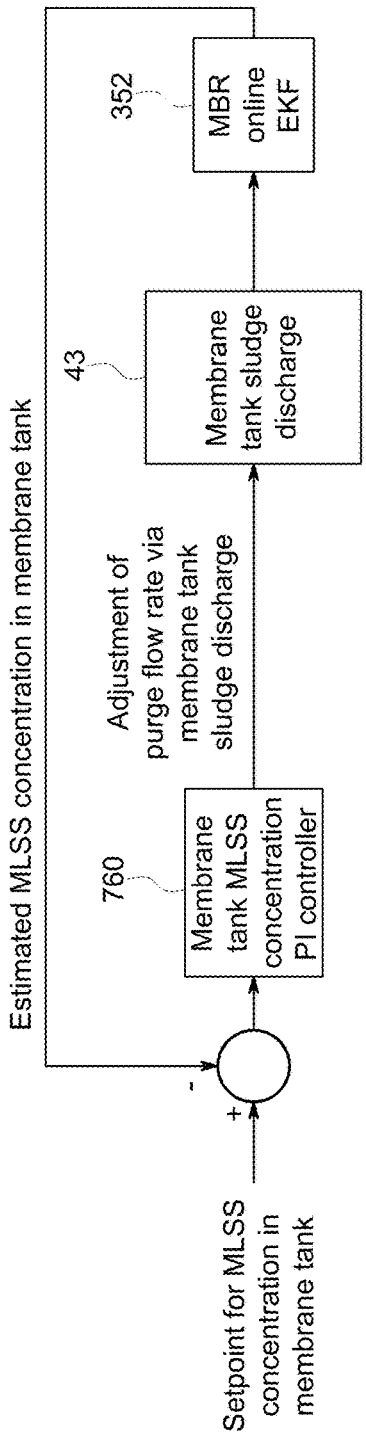
FIG. 32a is a block diagram depicting a control scheme for regulating the MLSS concentration within MBR membrane tank in accordance with aspects of the present technique.
Figure 33:
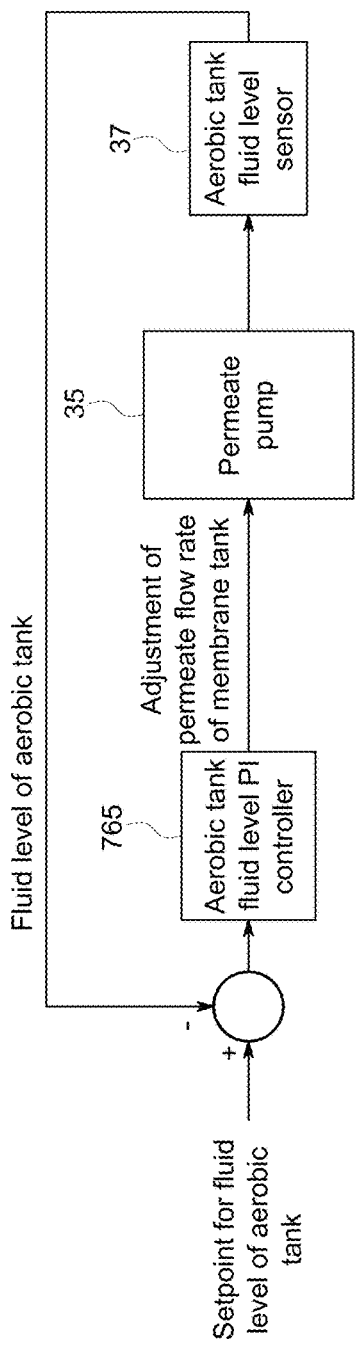
FIG. 33 is a block diagram depicting an aerobic tank fluid level PI controller in accordance with aspects of the present technique.

To realize control objectives, several basic control loops are used in the process: the Dissolved Oxygen (DO) in aerobic tank is controlled by the air blower flow rate (aeration) as shown in FIG. 29, pH levels in aerobic and anoxic tanks are controlled by the chemical flow rates (alkali, e.g. KOH) as shown in FIGS. 30-31, MLSS concentration in the membrane tank is controlled by the purge flow rate as shown in FIG. 32*a*, the aerobic tank fluid level is controlled by the permeate pump flow as shown in FIG. 33, and the total recycle flow is controlled to anoxic tank generally (in some cases the total recycle flow is controlled to aerobic tank and anoxic tank two reactors respectively). These lower level control loops are implemented with single loop PI control structure.

Some of the setpoints of the PI loops listed above are set by a MBR supervisory control system 301 of MBR control system 300 in cascade control configuration and min/max selection logic are used to determine the setpoints for some of the lower level control loops, to realize the ultimate MBR control objectives. Further, the operator control panel 1070 allows for manual adjustment of the setpoints.

The structure of MBR control system 300 is primarily based on feedback mechanism. For prompt response to known or measurable disturbances, feedforward control action is also added to the control structure to make sure the process can respond to disturbances swiftly. A fast response is ideal for an MBR system since the bio-chemical (bacteria growth) is a sensitive process. For the wastewater processing system, the most significant disturbances come from the raw feed variations. Feed characterization or measurement can be used for feedforward control action to overcome the feed variations.

Further, in the MBR control system 300, both anoxic tank recycle line 34 and additional bCOD (e.g. methanol) are used to control the $NO_3$ concentration in the permeate stream—the additional COD is used to augment COD feed for nitrification in the anoxic tank if the feed is lacking COD.

FIG. 29 depicts a control scheme for the dissolved oxygen (DO) within aerobic tank 32. The control scheme is comprised of aerobic tank DO concentration controller 745, aerobic tank aeration 38 (air blower), and aerobic tank 32. In some embodiments, aerobic tank DO concentration controller 745 is a PI controller. In operation, aerobic tank DO concentration controller 745 is provided with the difference between the setpoint for DO in aerobic tank 32 and the measured DO in aerobic tank 32. The DO measurement is provided by an aerobic tank DO sensor 65 situated in aerobic tank 32, aerobic tank DO concentration controller 745 then makes adjustments to the aerobic tank aeration 38 (air blower flow rate), which changes the amount of air provided to aerobic tank 32, such that the measured DO in aerobic tank 32 substantially corresponds with the setpoint for DO in aerobic tank 32. The setpoint for DO in aerobic tank 32 is determined by aerobic tank DO supervisory controller 1040. It is understood that alternatively an operator may also manually manipulate the aerobic tank DO setpoint on the operator control panel 1070.

FIG. 30 depicts a control scheme for the pH level within aerobic tank 32. The control scheme is comprised of aerobic tank pH controller 750, alkali tank 49, and aerobic tank 32. In some embodiments, aerobic tank pH controller 750 is a PI controller. In operation, aerobic tank pH controller 750 is provided with the difference between the setpoint of pH in aerobic tank 32 and the measured pH in aerobic tank 32. The pH measurement is provided by an aerobic tank pH level sensor 66 in aerobic tank 32. Aerobic tank pH controller 750 then makes adjustments to the chemical flow rate from alkali tank 49 (e.g. KOH or another suitable alkali), which changes the pH in aerobic tank 32, such that the measured pH in aerobic tank 32 substantially corresponds with the setpoint for pH level in aerobic tank 32. The setpoint for pH in aerobic tank 32 is determined by an operator on the operator control panel 1070. It is understood that alternatively, the setpoint for pH in aerobic tank 32 may be established by a controller of MBR supervisory control system 301.

FIG. 31 depicts a control scheme for the pH level within anoxic tank 31. The control scheme is comprised of anoxic tank pH controller 755, alkali tank 45, and anoxic tank 31. In operation, anoxic tank pH controller 755 is provided with the difference between the setpoint of pH in anoxic tank 31 and the measured pH in anoxic tank 31. The pH measurement is provided by anoxic tank pH sensor 67 in anoxic tank 31. Anoxic tank pH controller 755 then makes adjustments to the chemical flow rate from alkali tank 45 (e.g. KOH or another suitable alkali), which changes the pH in anoxic tank 31, such that the measured pH in anoxic tank 31 substantially corresponds with the setpoint for pH level in anoxic tank 31. The setpoint for pH in anoxic tank 31 is determined by an operator on the operator control panel 1070. It is understood that alternatively, the setpoint for pH in anoxic tank 31 may be established by a controller of MBR supervisory control system 301.

Figure 32B:
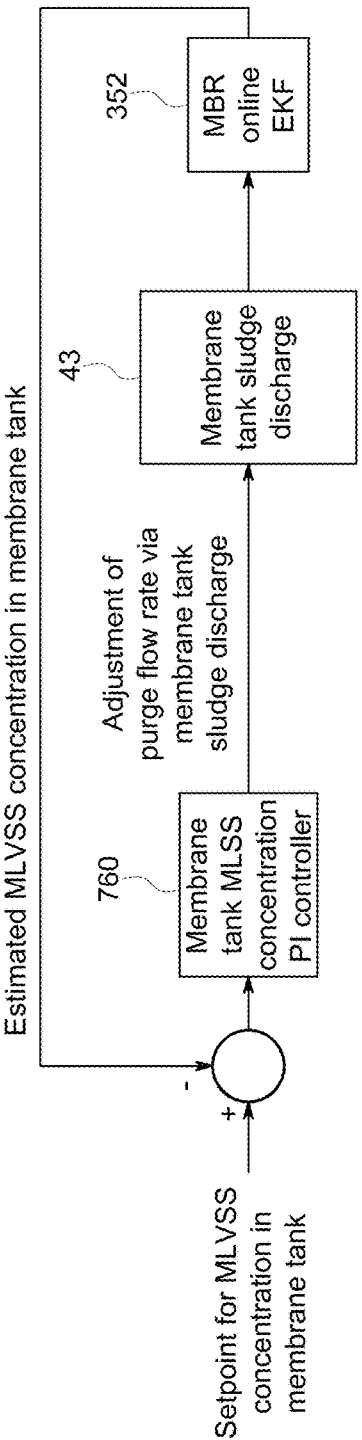
FIG. 32b is a block diagram depicting a control scheme for regulating the MLVSS concentration within MBR membrane tank in accordance with aspects of the present technique.

FIGS. 32a-b depicts a control scheme for the MLSS or MLVSS concentration within membrane tank 33. The control scheme is comprised of membrane tank MLSS concentration PI controller 760, membrane tank sludge discharge 43 of membrane tank 33, and MBR online EKF 352. FIG. 32a depicts an embodiment of membrane tank MLSS concentration PI controller 760 which controls the concentration of MLSS within membrane tank 33. In operation, membrane tank MLSS concentration PI controller 760 is provided with the difference between the setpoint for the MLSS concentration within membrane tank 33 and the estimated MLSS concentration within membrane tank 33. The estimated MLSS concentration within membrane tank 33 is provided by MBR online EKF 352. Membrane tank MLSS concentration PI controller 760 then makes adjustments to the purge flow rate of membrane tank 33 via the membrane tank sludge discharge 43, such that the estimated MLSS concentration within membrane tank 33 substantially corresponds with the setpoint for the MLSS concentration within membrane tank 33. The setpoint for the MLSS concentration within membrane tank 33 is determined by an operator on the operator control panel 1070. It is understood that alternatively, the MLSS concentration within membrane tank 33 may be established by a controller of MBR supervisory control system 301.

In the embodiment shown in FIG. 32b, it is contemplated that membrane tank MLSS concentration PI controller 760 is used to control the MLVSS in membrane tank 33. In such embodiments, membrane tank MLSS concentration PI controller 760 is provided with the difference between the setpoint for the MLVSS concentration within membrane tank 33 and the estimated MLVSS concentration within membrane tank 33. The estimated MLVSS concentration within membrane tank 33 is provided by MBR online EKF 352. Membrane tank MLSS concentration PI controller 760 then makes adjustments to the purge flow rate of membrane tank 33 via the membrane tank sludge discharge 43, such that the estimated MLVSS concentration within membrane tank 33 substantially corresponds with the setpoint for the MLVSS concentration within membrane tank 33. The setpoint for the MLVSS concentration within membrane tank 33 is determined by an operator on the operator control panel 1070. It is understood that alternatively, the MLVSS concentration within membrane tank 33 may be established by a controller of MBR supervisory control system 301. It is contemplated that in other embodiments, a membrane tank MLVSS concentration PI controller carries out the actions performed above in FIG. 32b by membrane tank MLSS concentration PI controller 760. If a membrane tank MLVSS concentration PI controller is present, it will be considered part of the MBR low-level control system 302.

FIG. 33 depicts a control scheme for the fluid level within aerobic tank 32. The control scheme is comprised of aerobic tank fluid level PI controller 765, permeate pump 35, and aerobic tank fluid level sensor 37. In operation, aerobic tank fluid level PI controller 765 is provided with the difference between the setpoint for the fluid level of aerobic tank 32 and the measured fluid level of aerobic tank 32. The measurement of the fluid level in aerobic tank 32 is provided by aerobic tank fluid level sensor 37. Aerobic tank fluid level PI controller 765 then makes adjustments to the flow rate of the membrane tank permeate pump 35, which changes the fluid level in aerobic tank 32, such that the measured fluid level of aerobic tank 32 substantially corresponds with the setpoint for the fluid level of aerobic tank 32. The setpoint for fluid level of aerobic tank 32 is established by an operator on the operator control panel 1070. It is understood that alternatively, the fluid level of aerobic tank 32 may be established by a controller of MBR supervisory control system 301.

Figure 34:
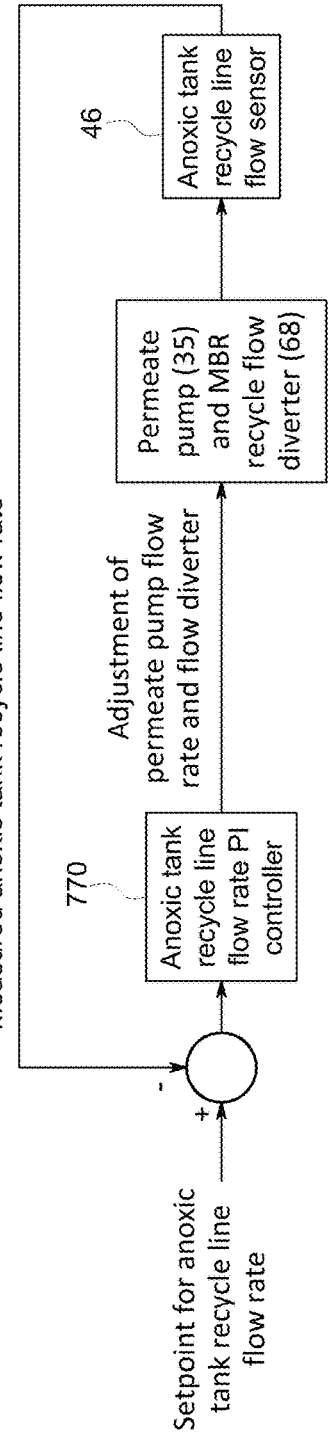
FIG. 34 is a block diagram depicting an anoxic tank recycle line flow rate PI controller in accordance with aspects of the present technique.

FIG. 34 depicts a control scheme for the flow rate of anoxic tank recycle line 34. The control scheme is comprised of anoxic tank recycle line flow rate PI controller 770, permeate pump 35, MBR recycle line flow diverter 68, and anoxic tank recycle line flow sensor 46. In operation, anoxic tank recycle line flow rate PI controller 770 is provided with the difference between the setpoint for anoxic tank recycle line flow rate and the measured anoxic tank recycle line flow rate. The anoxic tank recycle line flow rate is provided by anoxic tank recycle line flow sensor 46 in anoxic tank recycle line 34. Anoxic tank recycle line flow rate PI controller 770 then makes an adjustment to permeate pump 35 and MBR recycle line flow diverter 68, which changes the recycle line flow rate, such that the measured anoxic tank recycle line flow rate substantially corresponds to the setpoint for anoxic tank recycle line flow rate. The MBR recycle line flow diverter 68 changes the ratio of fluid flowing between anoxic tank recycle line 34 and aerobic tank recycle line 36. In some embodiments, the anoxic tank recycle line flow rate setpoint is established by anoxic tank recycle flow supervisory control 1045. It is understood that alternatively, the anoxic tank recycle line flow rate setpoint may be determined by an operator on the operator control panel 1070.

Figure 35:
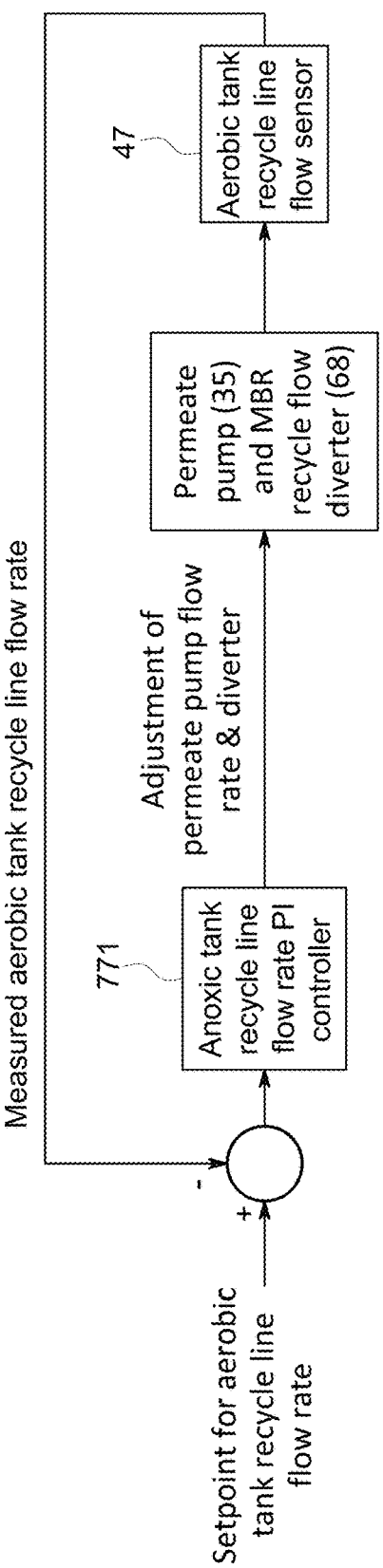
FIG. 35 is a block diagram depicting an aerobic tank recycle line flow rate PI controller in accordance with aspects of the present technique.

FIG. 35 depicts a control scheme for the flow rate of aerobic tank recycle line 36. The control scheme is comprised of aerobic tank recycle line flow rate PI controller 771, permeate pump 35, MBR recycle line flow diverter 68, and aerobic tank recycle line flow sensor 47. In operation, aerobic tank recycle line flow rate PI controller 771 is provided with the difference between the setpoint for aerobic tank recycle line flow rate and the measured aerobic tank recycle line flow rate. The aerobic tank recycle line flow rate is provided by aerobic tank recycle line flow sensor 47 in aerobic tank recycle line 36. Aerobic tank recycle line flow rate PI controller 771 then makes an adjustment to permeate pump 35 and MBR recycle line flow diverter 68, which changes the aerobic tank recycle line flow rate, such that the measured aerobic tank recycle line flow rate substantially corresponds to the setpoint for aerobic tank recycle line flow rate. The MBR recycle line flow diverter 68 changes the ratio of fluid flowing between anoxic tank recycle line 34 and aerobic tank recycle line 36. In some embodiments, the aerobic tank recycle line flow rate setpoint is determined by the MBR recycle line flow diverter 68. It is understood that alternatively, the aerobic tank recycle line flow rate setpoint may be determined by an operator on the operator control panel 1070.

Figure 36:
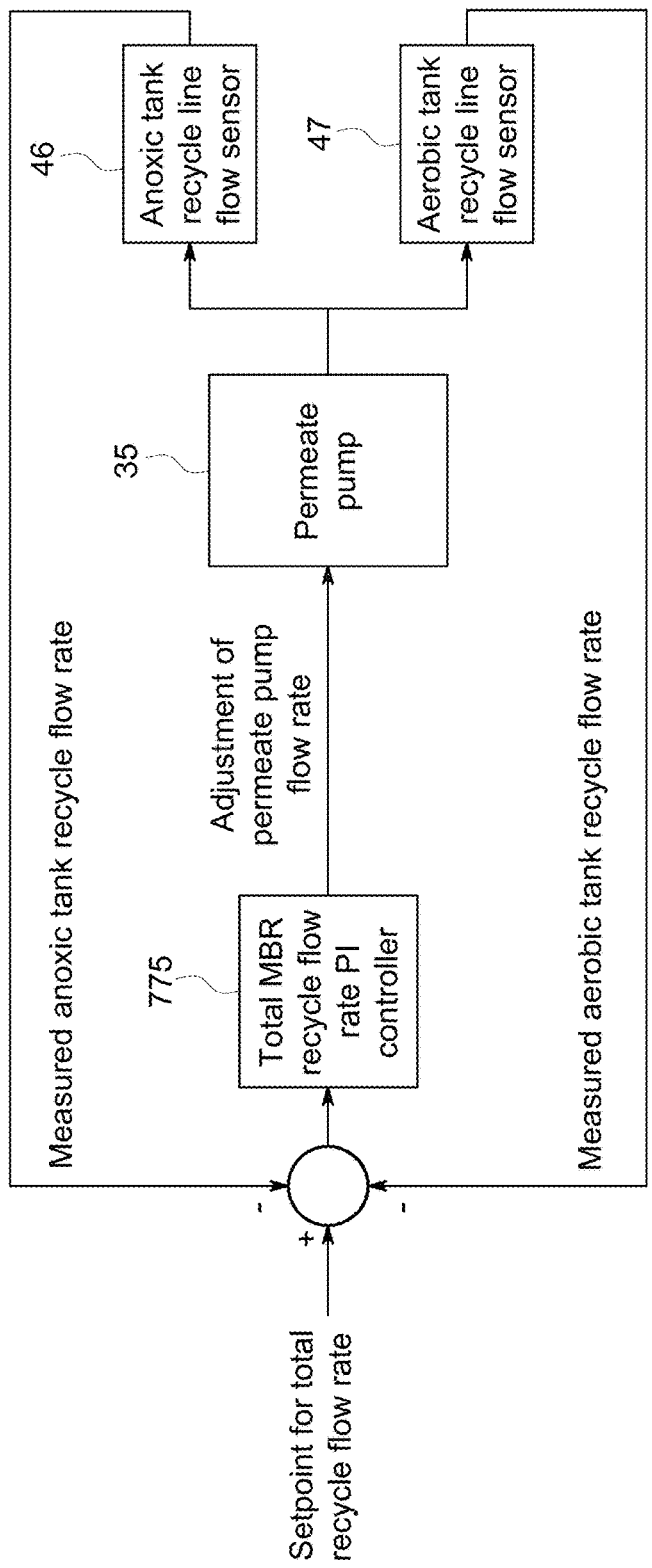
FIG. 36 is a block diagram depicting a total MBR recycle flow rate PI controller in accordance with aspects of the present technique.

FIG. 36 depicts a control scheme for controlling the total recycle flow rate in embodiments of MBR 30 having both anoxic tank recycle line 34 and aerobic tank recycle line 36. The control scheme is comprised of total MBR recycle flow rate PI controller 775, permeate pump 35, anoxic tank recycle line flow sensor 46, and aerobic tank recycle line flow sensor 47. In operation, total MBR recycle flow rate PI controller 775 is provided with the difference between the setpoint for total recycle flow rate and the sum of the measured anoxic tank recycle line flow rate and measured aerobic tank recycle line flow rate. The anoxic tank recycle line flow rate is provided by anoxic tank recycle line flow sensor 46 in anoxic tank recycle line 34. The aerobic tank recycle line flow rate is provided by aerobic tank recycle line flow sensor 47 in aerobic tank recycle line 36. Total MBR recycle flow rate PI controller 775 then makes an adjustment to permeate pump 35, which changes the flow rate of fluid through anoxic tank recycle line 34 and aerobic tank recycle line 36, such that the sum of the recycle flow rates through aerobic tank recycle line 36 and anoxic tank recycle line 34 substantially corresponds to the setpoint for total recycle flow rate. The total recycle flow rate is established by an operator on the operator control panel 1070. It is understood that alternatively, the total recycle flow rate may be determined by a controller of MBR supervisory control system 301.

Figure 37:
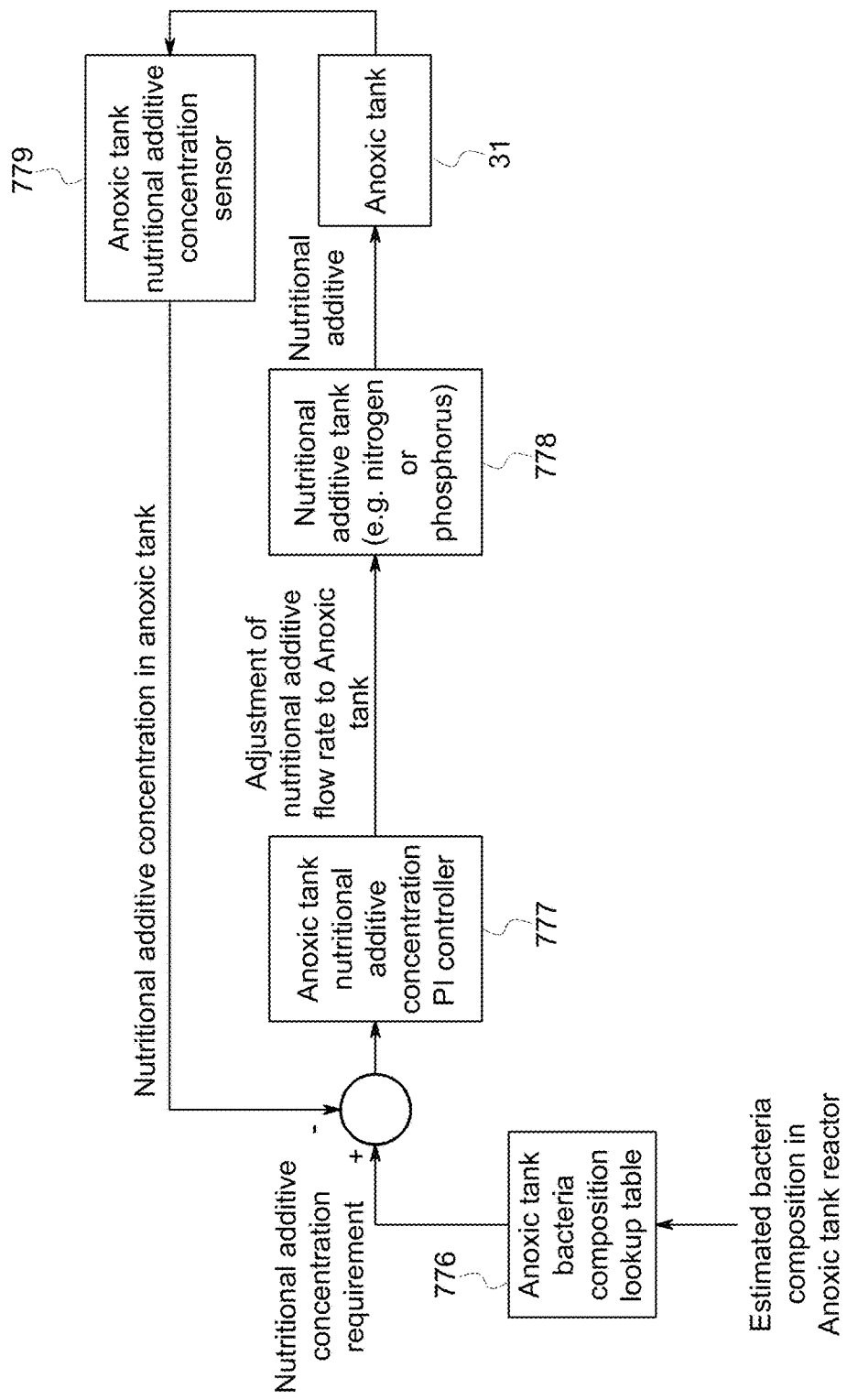
FIG. 37 is a block diagram depicting an anoxic tank nutritional additive concentration controller in accordance with aspects of the present technique.

FIG. 37 shows a scheme for regulating the nutrient concentration within some embodiments of anoxic tank 31 of MBR 30. It is contemplated in some embodiments of MBR 30, the amount and type of nutritional additives, provided to anoxic tank 31 will be determined by the estimated composition of the bacteria contained within anoxic tank 31. It is contemplated that in some embodiments, a anoxic tank nutritional additive concentration controller 777 and anoxic tank nutritional additive tank 778 will be provided for each nutrient of interest for anoxic tank 31. Further, it is contemplated that in some embodiments, all of the additive nutrients for anoxic tank 31 are combined in a single anoxic tank nutritional additive tank 778, accordingly, in those embodiments, only one anoxic tank nutritional additive concentration controller 777 and anoxic tank nutritional additive tank 778 will be present for MBR 30.

In one embodiment, anoxic tank nutritional additive concentration controller 777 is a PI controller. The nutritional additives may include, but are not limited to, nitrogen and phosphorus. The composition of bacteria in anoxic tank 31 will be estimated by MBR online EKF 352. An anoxic tank bacteria composition lookup table 776 is used to ascertain the nutritional additive concentration requirement for the composition of bacteria within anoxic tank 31 and output the concentration requirement for the specific nutritional additive of interest. The concentration of the nutritional additive of interest within anoxic tank 31 is ascertained via direct measurement via anoxic tank additive concentration sensor 779 contained within anoxic tank 31, or MBR online EKF 352. The concentration of the nutritional additive of interest present within anoxic tank 31 is subtracted from the concentration of the nutritional additive requirement to determine if a deficiency exists for the nutrient of interest and the difference is provided to anoxic tank nutritional additive concentration controller 777, which adjusts the flow rate of the nutritional additive of interest flowing from anoxic tank nutritional additive tank 778 into anoxic tank 31.

Accordingly, if a nutrient deficiency exists, nutritional additives are provided to anoxic tank 31 until the nutrient deficiency is rectified. Accordingly, the flow rates of the various nutritional additives of interest provided to anoxic tank 31 from the various anoxic tank nutritional additive tanks 778 are individually adjusted based on the amount of each species of bacteria present within each of anoxic tank 31 and nutrient concentration present within anoxic tank 31, so as not to overfeed or starve the bacteria.

In another embodiment in which all of the additive nutrients for anoxic tank 31 are combined in a single anoxic tank nutritional additive tank 778, the composition of bacteria in anoxic tank 31 will be estimated by MBR online EKF 352. An anoxic tank bacteria composition lookup table 776 is used to ascertain the nutritional additive concentration requirement for the composition of bacteria within anoxic tank 31 and output the concentration requirement for the nutritional additives of interest. The concentration of the nutritional additives of interest within anoxic tank 31 is ascertained via direct measurement via anoxic tank additive concentration sensor 779 contained within anoxic tank 31, or MBR online EKF 352. The concentration of the nutritional additives of interest present within anoxic tank 31 is subtracted from the concentration of the nutritional additive requirement to determine if a deficiency exists for the nutrients of interest and the difference is provided to anoxic tank nutritional additive concentration controller 777, which adjusts the flow rate of the nutritional additives of interest flowing from anoxic tank nutritional additive tank 778 into anoxic tank 31.

Accordingly, if a nutrient deficiency exists, nutritional additives are provided to anoxic tank 31 until the nutrient deficiency is rectified. Accordingly, the flow rate of the nutritional additives of interest provided to anoxic tank 31 is adjusted based on the amount of each species of bacteria present within each of anoxic tank 31 and nutrient concentration present within anoxic tank 31, so as not to overfeed or starve the bacteria.

Figure 38:
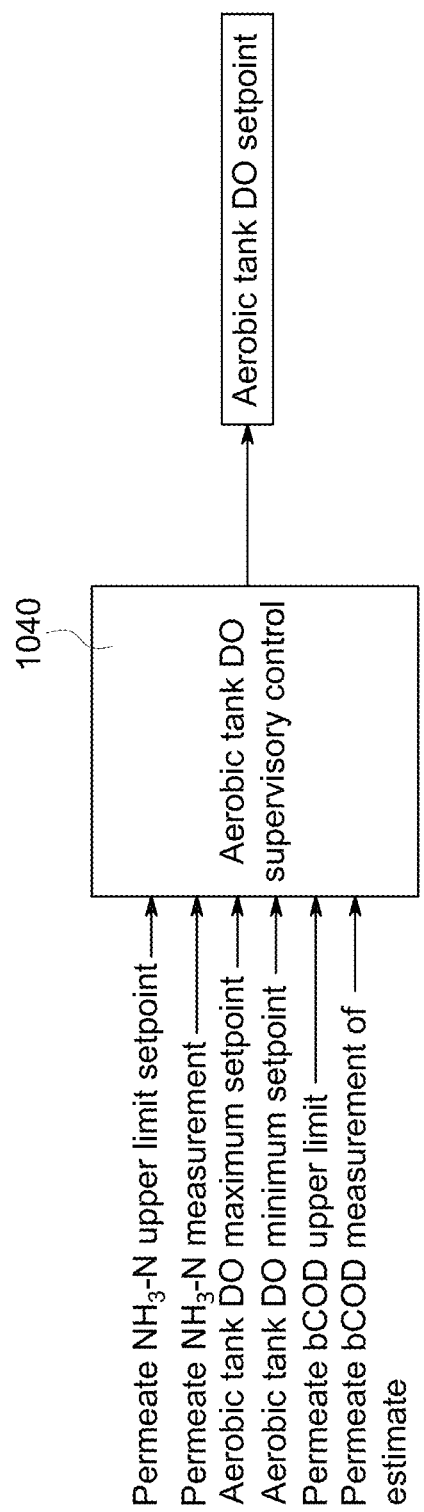
FIG. 38 is a block diagram depicting aerobic tank DO supervisory controller in accordance with aspects of the present technique.

FIG. 38 depicts the aerobic tank DO supervisory controller 1040, which establishes the aerobic tank DO setpoint.

In operation, aerobic tank DO supervisory controller 1040 receives the following inputs: permeate NH3-N upper limit setpoint, permeate NH3-N measurement, permeate bCOD upper limit setpoint, and permeate bCOD measurement or estimate, aerobic tank DO maximum setpoint, aerobic tank DO minimum setpoint. The permeate NH3-N upper limit setpoint permeate bCOD upper limit setpoint, aerobic tank DO maximum setpoint, and aerobic tank DO minimum setpoint are established by the operator on the operator control panel 1070. The permeate bCOD measurement is obtained from a laboratory analysis or estimate is received from MBR online EKF 352. The permeate NH3-N measurement is obtained from an NH3-N sensor in the permeate stream of membrane tank 33. Aerobic tank DO supervisory controller 1040 outputs the aerobic tank DO setpoint, which is connected to the setpoint for Dissolved Oxygen in Aerobic Tank as an input for FIG. 29. The operations that take place within aerobic tank DO supervisory controller 1040 are detailed in FIG. 41.

Figure 39:
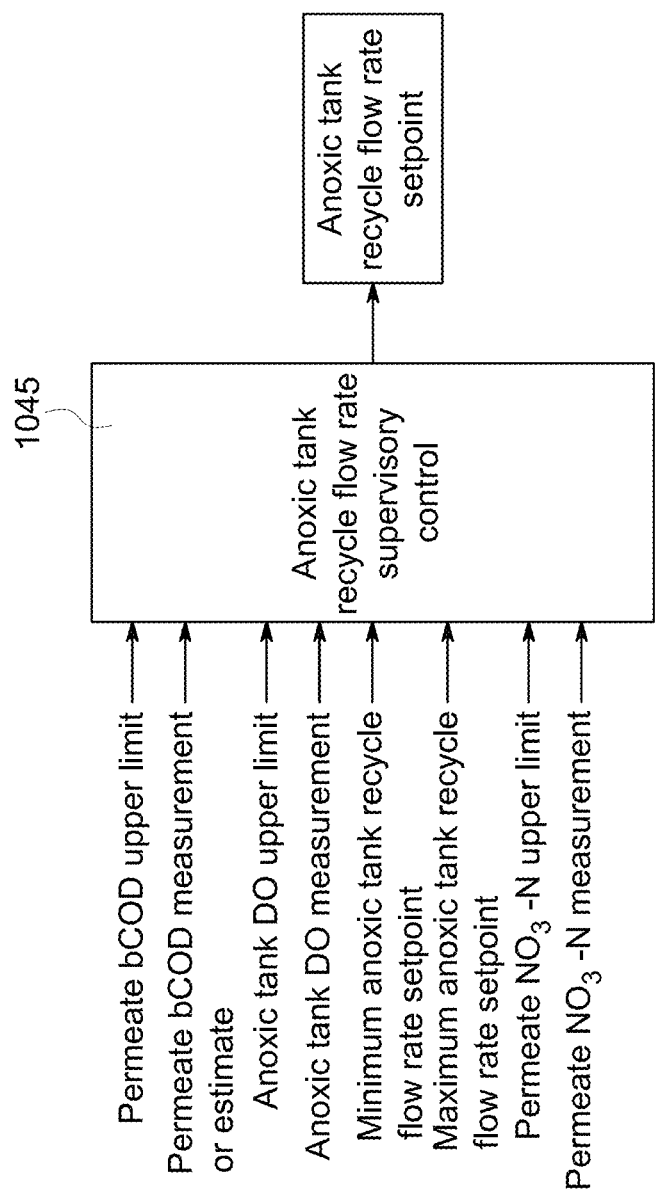
FIG. 39 is a block diagram depicting an anoxic tank recycle flow rate supervisory controller in accordance with aspects of the present technique.

FIG. 39 depicts anoxic tank recycle flow rate supervisory controller 1045. Anoxic tank recycle flow rate supervisory controller 1045 receives the following inputs: permeate bCOD upper limit setpoint, permeate bCOD measurement or estimate, anoxic tank DO upper limit setpoint, anoxic tank DO measurement, permeate NO3-N upper limit setpoint, permeate NO3-N measurement, minimum anoxic tank recycle flow rate setpoint, and maximum anoxic tank recycle flow rate setpoint. The permeate bCOD upper limit setpoint, anoxic tank DO upper limit setpoint, permeate NO3-N upper limit setpoint, minimum anoxic tank recycle flow rate setpoint, and maximum anoxic tank recycle flow rate setpoint are determined by an operator on the operator control panel 1070. The permeate bCOD measurement is obtained from a laboratory analysis (slow manual feedback) or an estimate received in real time from MBR online EKF 352. The anoxic tank DO measurement is obtained from a DO sensor in anoxic tank 31. The permeate NO3-N measurement is obtained from an NH3-N sensor in the permeate stream of membrane tank 33. Anoxic tank recycle flow rate supervisory controller 1045 outputs the anoxic tank recycle flow rate setpoint, which is connected to the Setpoint for Anoxic tank recycle line flow rate as the input of FIG. 34. The operations that take place within anoxic tank recycle flow rate supervisory controller 1045 are detailed in FIG. 42.

Figure 40:
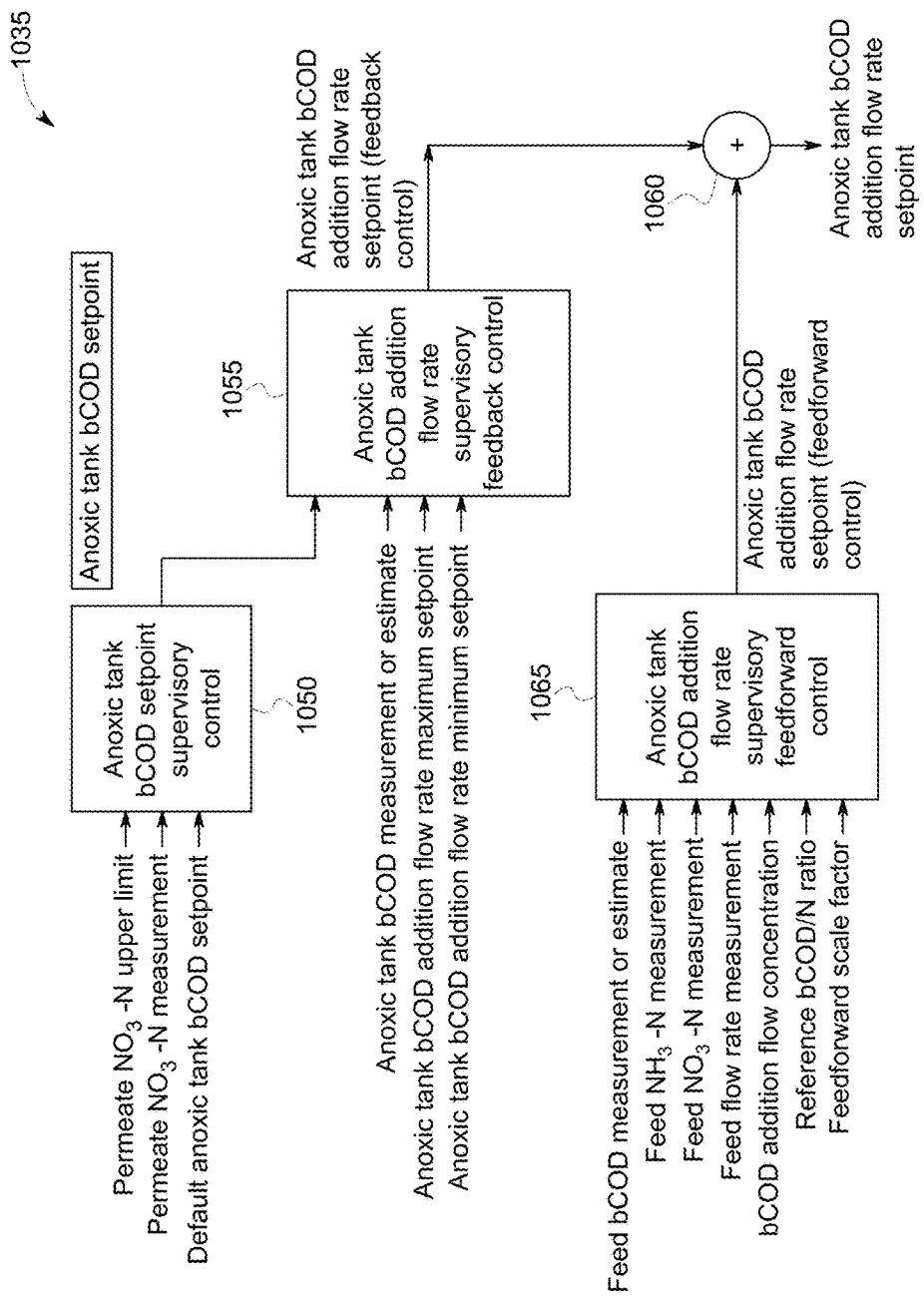
FIG. 40 is a block diagram depicting an anoxic tank biodegradable COD (bCOD) addition flow rate supervisory control scheme in accordance with aspects of the present technique.

FIG. 40 depicts anoxic tank biodegradable COD (bCOD) addition flow rate supervisory control scheme 1035, which is comprised of anoxic tank bCOD setpoint supervisory controller 1050, anoxic tank bCOD addition flow rate supervisory feedback controller 1055, anoxic tank bCOD addition flow rate supervisory feedforward controller 1065, and anoxic tank bCOD addition flow rate summation block 1060.

Anoxic tank bCOD setpoint supervisory controller 1050 receives the following inputs: default anoxic tank bCOD setpoint, permeate NO3-N upper limit setpoint and permeate NO3-N measurement. The permeate NO3-N upper limit setpoint and default anoxic tank bCOD setpoint are determined by an operator on the operator control panel 1070. The permeate NO3-N measurement is obtained from a sensor in the permeate stream of membrane tank 33. Anoxic tank bCOD setpoint supervisory controller 1050 outputs the anoxic tank bCOD setpoint. The operations that take place within anoxic tank bCOD setpoint supervisory controller 1050 are detailed in FIG. 43.

Anoxic tank bCOD addition flow rate supervisory feedback controller 1055 receives the following inputs: anoxic tank bCOD setpoint, anoxic tank bCOD measurement or estimate, anoxic tank bCOD addition flow rate maximum setpoint, and anoxic tank bCOD addition flow rate minimum setpoint. The anoxic tank bCOD setpoint is determined upstream by Anoxic tank bCOD setpoint supervisory controller 1050 or by an operator on the operator control panel 1070. The anoxic tank bCOD addition flow rate maximum setpoint and anoxic tank bCOD addition flow rate minimum setpoint are determined by an operator on the operator control panel 1070. The anoxic tank bCOD measurement is obtained from a laboratory analysis (slow manual feedback control) or estimate is received in real time from MBR online EKF 352. Anoxic tank bCOD addition flow rate supervisory feedback controller 1055 outputs the anoxic tank bCOD addition flow rate (feedback control) setpoint. The operations that take place within anoxic tank bCOD addition flow rate supervisory feedback control 1055 are detailed in FIG. 44.

Anoxic tank bCOD addition flow rate supervisory feedforward controller 1065 receives the following inputs: feed bCOD measurement or estimate at anoxic tank inlet, feed NH3-N measurement at anoxic tank inlet, feed NO3-N measurement at anoxic tank inlet, feed flow rate measurement at anoxic tank inlet, bCOD addition flow rate concentration setpoint, reference COD/N ratio setpoint, and feedforward scale factor setpoint. The bCOD addition flow rate concentration setpoint, reference bCOD/N ratio setpoint, and feedforward scale factor setpoint are determined by an operator on the operator control panel 1070. The feed NH3-N measurement, feed NO3-N measurement, and feed flow measurement are obtained from sensors at the inlet stream of anoxic tank 31. Anoxic tank bCOD addition flow rate supervisory feedforward controller 1065 outputs the anoxic tank bCOD addition flow rate (feedforward control) setpoint. The operations that take place within anoxic tank bCOD addition flow rate supervisory feedback control 1055 are detailed in FIG. 45.

Anoxic tank bCOD addition flow rate summation block 1060 receives the anoxic tank bCOD addition flow rate (feedback control) setpoint from anoxic tank bCOD addition flow rate supervisory feedback controller 1055 and anoxic tank bCOD addition flow rate (feedforward control) setpoint from anoxic tank bCOD addition flow rate supervisory feedforward controller 1065. Anoxic tank bCOD addition flow rate summation block 1060 outputs the anoxic tank bCOD addition flow rate setpoint, which determines the flow rate of bCOD entering anoxic tank 31 from bCOD tank.

Figure 41:
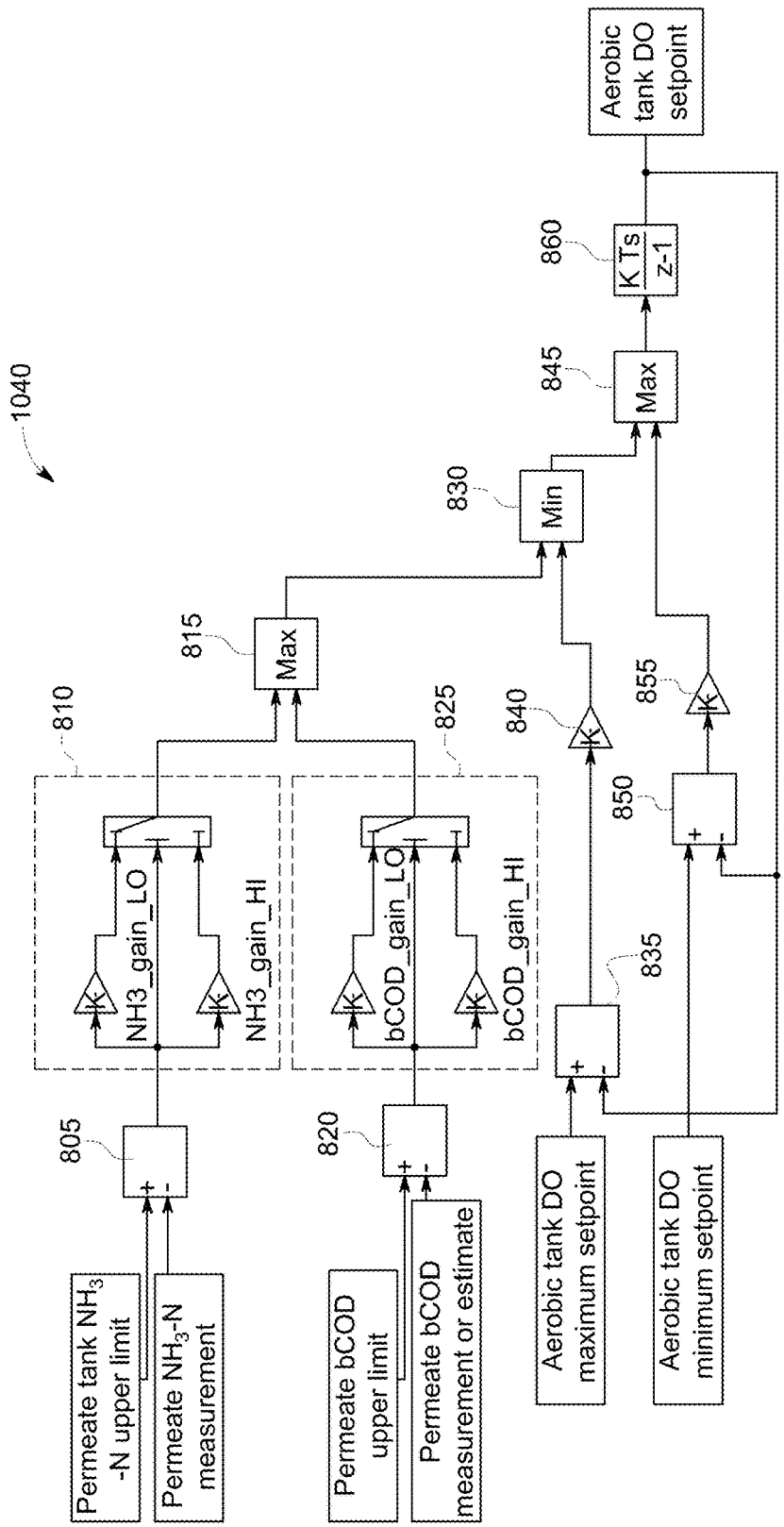
FIG. 41 is a block diagram depicting an aerobic tank DO supervisory controller in accordance with aspects of the present technique.

Aerobic tank DO supervisory controller 1040 is detailed in FIG. 41. In subtraction block 805, the permeate NH3-N measurement is subtracted from permeate NH3-N upper limit and the difference is passed to NH3-N gain scheduling control 810. Depending upon whether the difference between the permeate NH3-N upper limit and permeate NH3-N measurement exceeds a predetermined value established by a person having ordinary skill in the art, either a low gain or a high gain is applied to the output of subtraction block 805 and passed to maximum block 815.

In subtraction block 820, the permeate bCOD measurement or estimate is subtracted from the permeate bCOD upper limit and the difference is passed to bCOD gain scheduling control 825. Depending upon whether the difference between the permeate bCOD measurement or estimate and permeate bCOD upper limit exceeds a predetermined value established by a person having ordinary skill in the art, either a low gain or a high gain is applied to the output of subtraction block 820 and passed to maximum block 815. Maximum block 815 passes the greater of the outputs of bCOD gain scheduling control 825 or NH3-N gain scheduling control 810 to minimum block 830.

In subtraction block 835, the aerobic tank DO setpoint is subtracted from the aerobic tank DO maximum setpoint. Gain block 840 applies a gain to the output of subtraction block 835 and provides an output to minimum block 830. Minimum block 830 ensures that the aerobic tank DO setpoint does not exceed a maximum limit by passing the lesser of the output of gain block 840 or maximum block 815 to maximum block 845.

In subtraction block 850, the aerobic tank DO setpoint is subtracted from the aerobic tank DO minimum setpoint. Gain block 855 applies a gain to the output of subtraction block 850 and provides an output to maximum block 845. The greater of the output from gain block 855 and minimum block 830 is passed by maximum block 845, which ensures that the aerobic tank DO setpoint does not fall below a minimum limit. Integration control is provided to the output of maximum block 845 by discrete-time integrator block 860, which outputs the aerobic tank DO setpoint.

Figure 42:
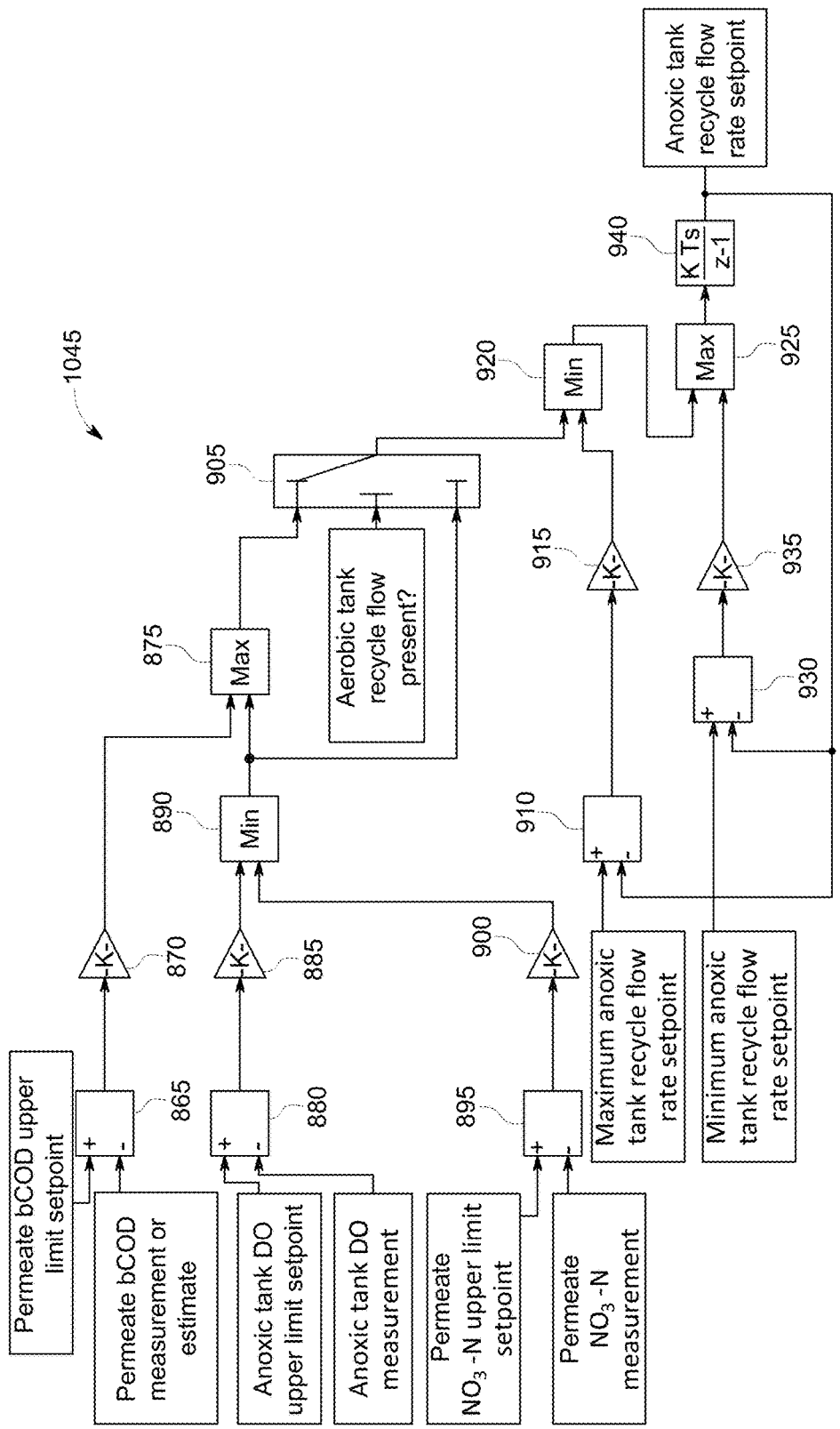
FIG. 42 is a block diagram depicting an anoxic tank recycle flow rate supervisory controller in accordance with aspects of the present technique.

Anoxic tank recycle flow rate supervisory controller 1045 is detailed in FIG. 42. In subtraction block 865, the permeate bCOD measurement or estimate is subtracted from the permeate bCOD upper limit setpoint. Gain block 870 applies a gain to the output of subtraction block 865 (control action for bCOD) and provides an output to maximum block 875. In subtraction block 880, the anoxic tank DO measurement is subtracted from the anoxic tank DO upper limit setpoint. Gain block 885 applies a gain to the output of subtraction block 880 (control action for anoxic tank DO concentration) and provides an output to minimum block 890. In subtraction block 895, the permeate NO3-N measurement is subtracted from the permeate NO3-N upper limit setpoint. Gain block 900 applies a gain to the output of subtraction block 895 (control action for NO3-N level) and provides an output to minimum block 890.

The lesser of the outputs from gain block 885 and gain block 900 are passed by minimum block 890 to maximum block 875 and switch 905. Minimum block 890 ensures that the minimum DO and NO3-N needs are satisfied and balanced in anoxic tank 31. The greater of the output from gain block 870 and minimum block 890 is passed by maximum block 875 to switch 905. Switch 905 passes the output of maximum block 875 to minimum block 920 if recycle is provided to both anoxic tank 31 and aerobic tank 32, otherwise switch 905 passes the output of minimum block 890 to minimum block 920.

In subtraction block 910, the anoxic tank recycle flow rate setpoint is subtracted from the maximum anoxic tank recycle flow rate setpoint and the difference is passed to gain block 915. Gain block 915 applies a gain to the output of subtraction block 910 and provides an output to minimum block 920, which ensures that the anoxic tank recycle flow rate setpoint does not exceed a maximum limit by passing the lesser of the outputs from switch 905 or gain block 915.

In subtraction block 930, the anoxic tank recycle flow rate setpoint is subtracted from the minimum anoxic tank recycle flow rate setpoint and the difference is passed to gain block 935. Gain block 935 applies a gain to the output of subtraction block 930 and provides an output to maximum block 925, which ensures that the anoxic tank recycle flow rate setpoint does not fall below a minimum limit by passing the greater of the outputs from minimum block 920 or gain block 935. Integration control is provided to the output of maximum block 925 by discrete-time integrator block 940, which outputs the anoxic tank recycle flow rate setpoint.

Figure 43:
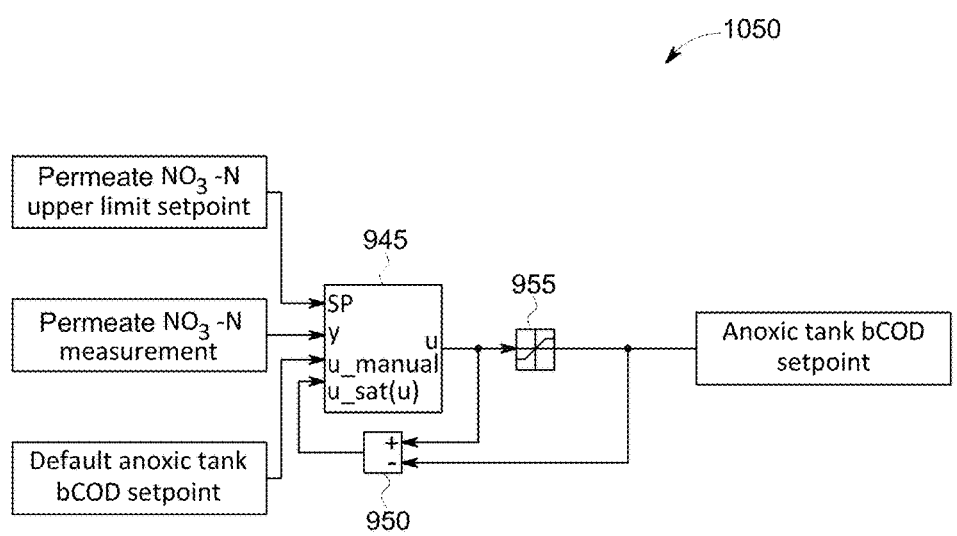
FIG. 43 is a block diagram depicting an anoxic tank bCOD setpoint supervisory controller in accordance with aspects of the present technique.

Anoxic tank bCOD setpoint supervisory controller 1050 is detailed in FIG. 43. Anti-windup PI control 945 receives an anti-windup correction signal from subtraction block 950, permeate NO3-N upper limit setpoint, permeate NO3-N measurement, and default anoxic tank bCOD setpoint. Anti-windup PI control 945 provides an output to anoxic tank bCOD range limiter 955, which outputs the anoxic tank bCOD setpoint. In subtraction block 950, the anoxic tank bCOD setpoint is subtracted from the output of anti-windup PI control 945, and subtraction block 950 provides an anti-windup correction signal to anti-windup PI control 945. The output of anoxic tank bCOD setpoint supervisory controller 1050 is cascaded to the input of the anoxic tank bCOD addition flow rate supervisory feedback controller 1055.

Figure 44:
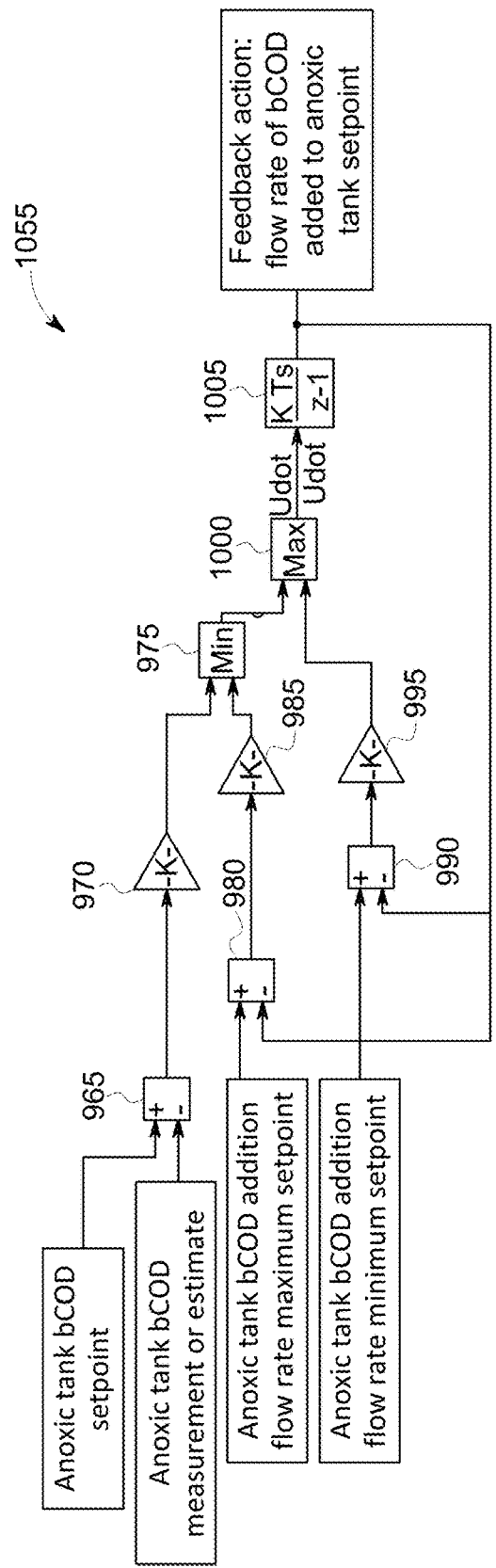
FIG. 44 is a block diagram depicting an anoxic tank bCOD addition flow rate supervisory feedback controller in accordance with aspects of the present technique.

Anoxic tank bCOD addition flow rate supervisory feedback controller 1055 is detailed in FIG. 44. In subtraction block 965, the anoxic tank bCOD measurement or estimate is subtracted from the anoxic tank bCOD setpoint. Gain block 970 applies a gain to the output of subtraction block 965 and provides an output to minimum block 975. In subtraction block 980, the anoxic tank bCOD addition flow rate setpoint (feedback control) is subtracted from the anoxic tank bCOD addition flow rate maximum setpoint. Gain block 985 applies a gain to the output of subtraction block 980 and provides an output to minimum block 975.

In subtraction block 990, the anoxic tank bCOD addition flow rate setpoint (feedback control) is subtracted from the anoxic tank bCOD addition flow rate minimum setpoint. Gain block 995 applies a gain to the output of subtraction block 990 and provides an output to maximum block 1000.

Minimum block 975 ensures that the anoxic tank bCOD addition flow rate setpoint (feedback control) does not exceed a maximum limit by passing the lesser of the output from gain block 970 or gain block 985 to maximum block 1000. The greater of the output from minimum block 975 and gain block 995 is passed by maximum block 1000, which ensures that the anoxic tank bCOD addition flow rate setpoint (feedback control) does not fall below a minimum limit. Integration control is provided to the output of maximum block 1000 by discrete-time integrator block 1005, which outputs the anoxic tank bCOD addition flow rate setpoint (feedback control).

Figure 45:
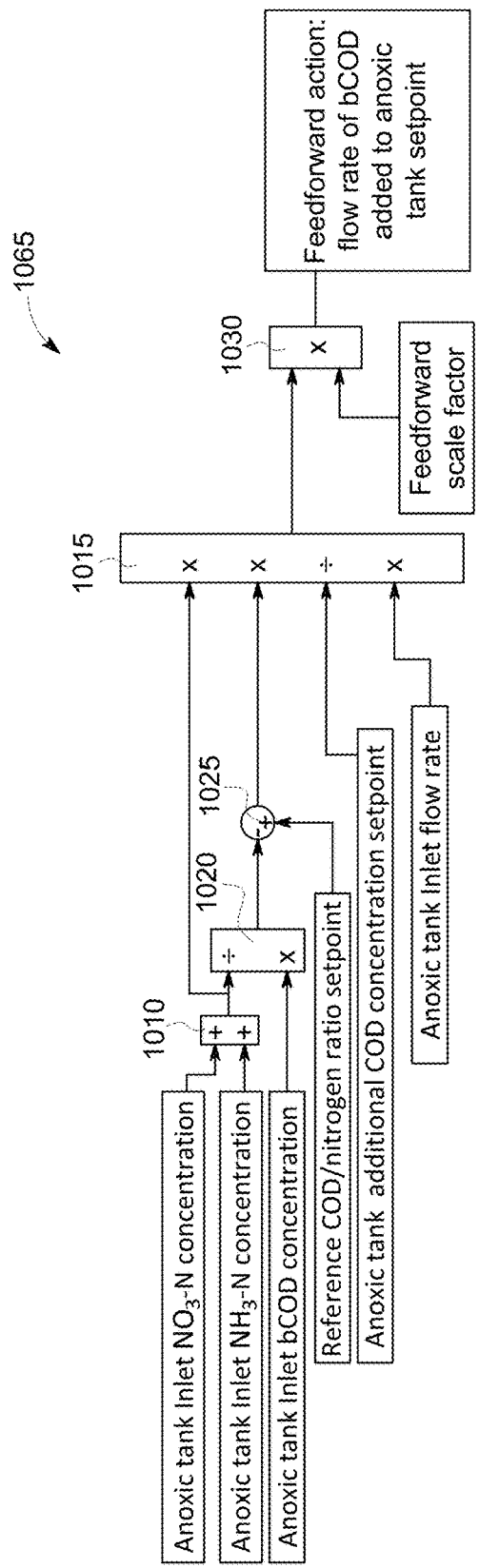
FIG. 45 is a block diagram depicting an anoxic tank bCOD addition flow rate supervisory feedforward controller in accordance with aspects of the present technique.

Anoxic tank bCOD addition flow rate supervisory feedforward controller 1065 is detailed in FIG. 45. In addition block 1010, the anoxic tank inlet NO3-N concentration and anoxic tank inlet NH3-N concentration are added together. The output of addition block 1010 is provided to operation block 1015 and operation block 1020. Operation block 1020 divides the anoxic tank inlet bCOD concentration by the output of addition block 1010. The output of operation block 1020 is provided to block 1025, which subtracts the output of operation block 1020 from the reference bCOD/Nitrogen ratio setpoint. The output of block 1025 is provided to operation block 1015.

In operation block 1015, the output of addition block 1010, the output of block 1025, and the anoxic tank inlet flow rate are multiplied together, and that product is divided by the anoxic tank addition bCOD concentration setpoint. The output of operation block 1015 is provided to block 1030. In block 1030, the output of operation block 1015 is multiplied by the feedforward scale factor, which is to tune the aggressiveness of the feedforward control. The result of block 1030 is the anoxic tank bCOD addition flow rate setpoint (feedforward control). The anoxic tank bCOD addition flow rate setpoint is established by adding the anoxic tank bCOD addition flow rate setpoint (feedback control) to the anoxic tank bCOD addition flow rate setpoint (feedforward control).

Figure 46:
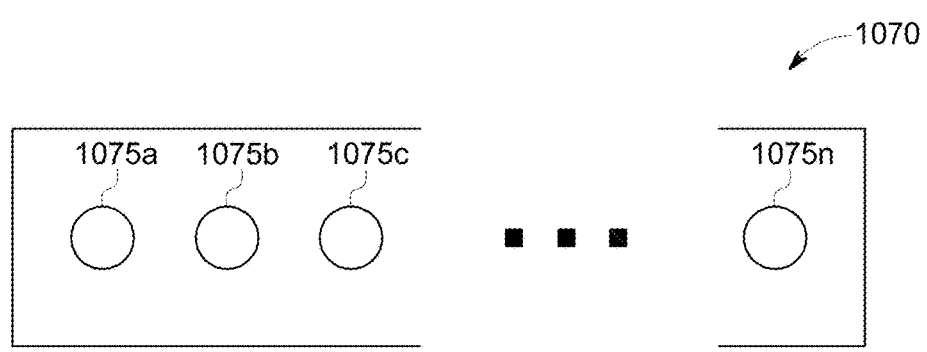
FIG. 46 depicts an operator control panel in accordance with aspects of the present technique.

As can be seen, disclosed in FIGS. 29-45 is an improved method of providing optimal control of MBR 30. The method allows a operator to define optimal setpoints for multiple available control inputs through operator control panel 1070 show in FIG. 46, which includes setpoints for multiple process variables for AD control system 200 setpoints and MBR control system 300 setpoints. Operator panel includes setpoints such as, dissolved oxygen (DO) concentration setpoints, recycling flow from the membrane tank 33 to anoxic tank 31, recycling flow from the membrane tank 33 to aerobic tank 32 and bypassing the anoxic tank, adding additional chemical oxygen demand (COD) concentrations to the anoxic tank, and mixed liquor suspended solids (MLSS) concentration setpoint. Further, the method can automate setpoint adjustment based on monitoring permeate demands, feed flow rate, feed composition, as well as other factors. The optimal setpoints can then be defined by the MBR model discussed above, or obtained by system perturbations. The optimal setpoints are obtained with or without chemical addition for MBR membrane fouling inhibition. Accordingly, AD control system 200 and MBR control system 300 are both comprised of operator control panel 1070. It is understood that in some embodiments, a single operator control panel 1070 can provide setpoints for both AD control system 200 and MBR control system 300. Further, in other embodiments, AD control system 200 includes an operator control panel 1070, and MBR control system 300 includes a operator control panel 1070.

In practice, the proposed method regulates the setpoints of the operational variables controlled in MBR control system 300, such as permeate control, RAS control, DO control, and additional COD control, and identifies their optimal values.

The MBR control system 300 acts to regulate permeate quality of MBR 30 (concentration of bCOD, $NH_3$—N, $NO_3$—N in the output), and to maintain the concentration below a maximum specification limit. The MBR control system 300 also minimize aeration (energy use) and chemical use (pH regulation). These controls are maintained by calculating optimal set points for multiple control inputs.

As shown in FIGS. 38-45, the MBR supervisory control system 301 utilizes both maximum values, minimum values, and current feedback to calculate optimal set points. Specifically, the maximum value for permeate bCOD, the current value for permeate bCOD, the maximum value for permeate NH3-N, the current value for permeate NH3-N, the maximum value for permeate NO3-N, the current value for permeate NO3-N, the maximum value for anoxic tank DO, and the current value for anoxic tank DO are used in MBR supervisory control system 301 to calculate the optimal operation to satisfy the setpoints for permeate bCOD, NH3-N, and NO3-N. Specifically, MBR supervisory control system 301 utilizes these limits and the max/min signal selection logic to enable the MBR supervisory control system 301 to calculate the optimal setpoints for the lower control loops, therefore optimal operation condition for the process, which in turn, regulates permeate quality and maintain it below the maximum specification limit, and minimizes aeration and chemical use.

As can be seen, MBR control system 300 is comprised of a MBR supervisory control system 301 and a MBR low-level control system 302. MBR supervisory control system 301 is comprised of operator control panel 1070, aerobic tank DO supervisory controller 1040, anoxic tank recycle flow supervisory controller 1045, and anoxic tank bCOD addition flow supervisory control scheme 1035.

Anoxic tank bCOD addition flow supervisory control scheme 1035 is comprised of anoxic tank bCOD setpoint supervisory controller 1050, Anoxic tank bCOD addition flow rate supervisory feedback controller 1055, and Anoxic tank bCOD addition flow rate supervisory feedforward controller 1065.

Further, MBR low-level control system 302 is comprised of aerobic tank fluid level PI controller 765, aerobic tank pH controller 750, anoxic tank pH controller 755, anoxic tank recycle line flow rate PI controller 770, aerobic tank recycle line flow rate PI controller 771, total MBR recycle flow rate PI controller 775, aerobic Tank DO concentration controller 745, membrane tank MLSS concentration controller 760, and anoxic tank nutritional additive concentration controller 777.

Additionally, AD control system 200 is comprised of an AD supervisory control system 201 and an AD low-level control system 202. AD supervisory control system 201 is comprised of operator control panel 1070, AD reactor pH supervisory controller 700, PA reactor pH supervisory controller 701, and PA:AD overall recycle flow ratio supervisory controller 720.

AD reactor pH supervisory controller 700 is comprised of AD reactor nonlinear PI pH controller 705 and AD reactor P alkalinity controller 710. PA reactor pH supervisory controller 701 is comprised of PA reactor nonlinear PI pH controller 706 and PA reactor P alkalinity controller 711. PA:AD overall recycle flow ratio supervisory controller 720 is comprised of PA:AD recycle ratio controller 725, and PA reactor and AD reactor recycle flow rate controller 730.

Further, AD low-level control system 202 is comprised of AD reactor biomass concentration controller 735, PA reactor fluid level controller 737, PA reactor nutritional additive concentration controller 51, and AD reactor nutritional additive concentration controller 61.

While preferred embodiments of the present invention have been described, it should be understood that the present invention is not so limited and modifications may be made without departing from the present invention. The scope of the present invention is defined by the appended claims, and all devices, processes, and methods that come within the meaning of the claims, either literally or by equivalence, are intended to be embraced therein.

While this invention has been described in conjunction with the specific embodiments described above, it is evident that many alternatives, combinations, modifications and variations are apparent to those skilled in the art. Accordingly, the preferred embodiments of this invention, as set forth above are intended to be illustrative only, and not in a limiting sense. Various changes can be made without departing from the spirit and scope of this invention. Therefore, the technical scope of the present invention encompasses not only those embodiments described above, but also all that fall within the scope of the appended claims.

This written description uses examples to disclose the invention, including the best mode, and also to enable any person skilled in the art to practice the invention, including making and using any devices or systems and performing any incorporated processes. The patentable scope of the invention is defined by the claims, and may include other examples that occur to those skilled in the art. These other examples are intended to be within the scope of the claims if they have structural elements that do not differ from the literal language of the claims, or if they include equivalent structural elements with insubstantial differences from the literal language of the claims.

What is claimed is:

1. A method of monitoring and controlling the operating conditions of an anaerobic digester (AD), comprising:
providing an AD;
monitoring said AD, wherein said monitoring comprises:
providing an AD offline extended Kalman filter (EKF) having an offline dynamic model of said AD, providing an AD online EKF having an online dynamic model of said AD; wherein said offline and said online dynamic models of said AD are comprised of states, process material balances, energy balances, bio-chemical reaction kinetics, estimated parameters, and adapted model parameters; wherein said adapted model parameters are a subset of said estimated parameters;
providing historical operation data for said AD, wherein said historical operation data is comprised of historical measured input data, historical measured output data, and historical laboratory analysis data;
identifying said estimated parameters of said offline dynamic model of said AD using said AD offline EKF and said historical operation data for said AD;
importing said estimated parameters from said offline dynamic model of said AD into said online dynamic model of said AD;
providing real time operation data for said AD to said AD online EKF, wherein said real time operation data is comprised of real time measured input data and real time measured output data of said AD;
updating said adapted model parameters of said online dynamic model of said AD and estimating one or more model based inferred variables of said AD using said AD online EKF, said online dynamic model of said AD, said real time measured input data of said AD, and said real time measured output data of said AD; and
providing one or more of said adapted model parameters of said online dynamic model of said AD and said model based inferred variables of said AD to an operator of said AD;
wherein limits are applied to one or more of said estimated parameters and said adapted model parameters; wherein constraints are applied to one or more of said model based inferred variables;
controlling said AD, wherein said controlling comprises:
providing an AD control system;
wherein said AD is comprised of an AD reactor and optionally a PA reactor; wherein said AD control system uses one or more of said real time measured input data of said AD, said real time measured output data of said AD, said estimated parameters of said online dynamic model of said AD, or said model based inferred variables of said AD to control at least one of a nutritional additive concentration of said AD reactor, a nutritional additive concentration of said PA reactor, AD reactor pH, PA reactor pH, biomass concentration of said AD reactor, fluid level of said PA reactor, or a recycle flow rate of said AD;
wherein said AD control system is comprised of an AD supervisory control system and an AD low-level control system.

2. The method of claim 1, wherein said AD is comprised of an AD reactor.

3. The method of claim 2, wherein said AD reactor is a continuously stirred tank reactor (CSTR), upflow anaerobic sludge blanket reactor (UASB), expanded granular sludge bed reactor (EGSB), mixed bed, moving bed, low-rate, or high-rate reactor.

4. The method of claim 2, wherein said AD is further comprised of a pre-acidification (PA) reactor, wherein said AD reactor and said pre-acidification reactor are modeled separately in both of said online and offline dynamic models of said AD.

5. The method of claim 2, wherein said AD is comprised of a mixing stage and at least one recycle line.

6. The method of claim 5, wherein said at least one recycle line of said AD is a pre-acidification reactor recycle line or an AD reactor recycle line.

7. The method of claim 1, wherein materials for said material balances in said online and offline dynamic models of said AD are comprised of insoluble organics, soluble substrates, volatile fatty acids, biomass, inorganic carbon and alkalinity.

8. The method of claim 7, wherein said insoluble organics is comprised of carbohydrates, protein and fat; wherein said soluble substrate and VFA include at least one of sugars, long chain fatty acids (LCFA), amino acids, acetate acid, or propionate acid; wherein said biomass includes biomass for acedogenesis, acetogenesis, acetoclastic methanogenesis and hydrogen methanogenesis bio-chemical processes.

9. The method of claim 7, wherein said inorganic carbon is comprised of at least one of carbon dioxide ($CO_2$), carbonate, or bicarbonate.

10. The method of claim 7, wherein said alkalinity is comprised of alkalinity associated with bicarbonate, VFA, added alkali, and generation of ammonia and hydrogen sulfide.

11. The method of claim 1, wherein said bio-chemical reaction kinetics in said online and offline dynamic models of said AD are comprised of at least one of insoluble organics hydrolysis, acedogenesis, acetogenesis, acetoclastic methanogenesis, or a hydrogen methanogenesis process.

12. The method of claim 1, wherein said AD is further comprised of a PA reactor, wherein said historical operation data of said AD and said real time operation data of said AD are comprised of at least one of raw influent pH, raw influent temperature, raw influent flow rate, raw influent total organic carbon (TOC), raw influent total inorganic carbon (TIC), added alkali flow rate, PA reactor fluid level, AD feed flow rate, raw influent soluble chemical oxygen demand (SCOD), raw influent total chemical oxygen demand (TCOD), raw influent soluble bio-chemical oxygen demand (SBOD), raw influent volatile suspended solids (VSS), raw influent total suspended solids (TSS), raw influent soluble inorganic nitrogen, raw influent VFA, added alkali concentration, PA reactor pH, PA effluent TOC, PA effluent TIC, AD biogas flow rate, AD biogas methane ($CH_4$) concentration, AD Biogas $CO_2$ concentration, AD reactor pH, AD effluent TOC, AD effluent TIC, AD effluent VFA, AD effluent alkalinity, AD reactor mixed liquor volatile suspended solids (MLVSS), AD effluent TCOD, AD effluent SCOD, AD effluent VSS, or AD effluent TSS.

13. The method of claim 1, wherein said AD is further comprised of a PA reactor, wherein said estimated parameters and said adapted model parameters of said offline dynamic model of said AD and said online dynamic model of said AD are comprised of at least one of PA reactor composite fraction of carbohydrate, PA reactor composite fraction of fat, PA reactor composite fraction of protein, PA reactor fraction of insoluble convertible to SBOD, PA reactor acedogenthese reaction coefficient, PA reactor biomass decay rate, PA reactor insoluble hydrolysis reaction coefficient, PA reactor insoluble flow out coefficient, PA reactor $CO_2$ escape coefficient, AD reactor composite fraction of carbohydrate, AD reactor composite fraction of fat, AD reactor composite fraction of protein, AD reactor fraction of insoluble convertible to SBOD, AD reactor acedogenthese reaction coefficient, AD reactor acetogenesis reaction coefficient, AD reactor acetoclastic methanogenesis reaction coefficient, AD reactor hydrogen methanogenesis reaction coefficient, AD reactor biomass decay rate, PA reactor insoluble hydrolysis reaction coefficient, or PA reactor insoluble flow out coefficient.

14. The method of claim 1, wherein at least one of said estimated parameters of said offline dynamic model of said AD and said model based inferred variables of said online dynamic model of said AD are estimated with confidence intervals.

15. The method of claim 1, wherein said AD is further comprised of a PA reactor, wherein said model based inferred variables of said online dynamic model of said AD are comprised of at least one of the following unmeasured inputs or outputs of said AD: raw influent insoluble COD, raw influent insoluble inert COD, raw influent soluble inert COD, raw influent SBOD saccharide, raw influent SBOD LCFA, raw influent SBOD amino acid, raw influent propionate acid, raw influent acetate acid, raw influent inorganic carbon content, raw influent alkalinity, raw influent inorganic nitrogen, raw influent SCOD, raw influent TCOD, raw influent SBOD, PA reactor alkalinity, PA reactor VFA, PA reactor temperature, PA reactor SCOD, PA reactor TCOD, PA reactor SBOD, AD reactor alkalinity, AD reactor VFA, AD reactor temperature, AD reactor SCOD, AD reactor SBOD, AD reactor acedogenthese biomass, AD reactor acetogenesis biomass, AD reactor acetoclastic methanogenesis biomass, AD reactor hydrogen methanogenesis biomass, AD reactor insoluble COD, AD reactor insoluble inert COD, AD reactor soluble inert COD, AD reactor SBOD saccharide, AD reactor SBOD LCFA, AD reactor SBOD amino acid, AD reactor propionate acid, AD reactor acetate acid, AD reactor inorganic carbon content, AD reactor alkalinity, AD reactor inorganic nitrogen, AD reactor SCOD, AD reactor TCOD, AD reactor SBOD, SCOD conversion rate, $CH_4$ conversion efficiency, or recycle flow rate.

16. The method of claim 1, further comprising tuning said adapted model parameters of said online dynamic model of said AD using different weights for said real time operation data and a prior knowledge of measurement accuracy of said real time operation data.

17. The method of claim 1, further comprising adjusting said adapted model parameters of said online dynamic model of said AD by one or both of:
calculating model predicted outputs of said AD using said AD online EKF, said online dynamic model of said AD, said real time measured input data of said AD, and said real time measured output data of said AD, comparing said measured output data of said AD and said model predicted outputs of said AD, and updating said adapted model parameters of said online dynamic model of said AD such that said real time measured output data of said AD substantially correspond with said model predicted outputs of said AD; or
periodically re-identifying said estimated parameters of said offline dynamic model of said AD using said AD offline EKF and said historical operation data for said AD, and importing said estimated parameters from said offline dynamic model of said AD into said online dynamic model of said AD.

18. The method of claim 1, wherein at least one of said monitoring said AD or said controlling said AD is performed using a computer.

19. The method of claim 1, wherein controlling said nutritional additive concentration of said AD prevents biomass overfeeding and starvation, wherein controlling said nutritional additive concentration of said PA reactor prevents biomass overfeeding and starvation, wherein controlling said AD reactor pH minimizes alkali dosing, wherein controlling said PA reactor pH minimizes alkali dosing, wherein controlling said biomass concentration of said AD reactor offsets biomass inhibition and saves alkali, wherein controlling a recycle flow rate of said PA reactor minimizes alkali dosing and maintains fluid level of said PA reactor, and wherein controlling a recycle flow rate of said AD reactor maximizes COD conversion and biogas generation.

20. The method of claim 1, wherein said AD supervisory control system is comprised of at least one of an AD reactor pH supervisory controller, a PA reactor pH supervisory controller, or an PA:AD overall recycle flow ratio supervisory controller.

21. The method of claim 20, wherein said AD reactor pH supervisory controller is comprised of an AD reactor nonlinear Proportion-Integration (PI) pH controller and an AD reactor Proportion (P) alkalinity controller in a cascaded configuration.

22. The method of claim 20, wherein said PA reactor pH supervisory controller is comprised of a PA reactor nonlinear PI pH controller and a PA reactor P alkalinity controller in a cascaded configuration.

23. The method of claim 20, wherein said PA:AD overall recycle flow ratio supervisory controller is comprised of a PA:AD recycle ratio controller, and a PA reactor and AD reactor recycle flow rate controller.

24. The method of claim 1, wherein said AD low-level control system is comprised of at least one of an AD reactor biomass concentration controller, a PA reactor fluid level controller, a PA reactor nutritional additive concentration controller, or an AD reactor nutritional additive concentration controller.

25. The method of claim 20, wherein at least one of said AD reactor pH supervisory controller or said PA reactor pH supervisory controller uses one or more of said model based inferred variables of said AD.

26. The method of claim 25, wherein said model based inferred variables of said AD include PA alkalinity and/or AD alkalinity.

27. The method of claim 20, wherein at least one of said AD reactor pH supervisory controller or said PA reactor pH supervisory controller has a feedforward control action; wherein said feedforward control action uses one or more of said a model based inferred variables of said AD.

28. The method of claim 27, wherein said model based inferred variables of said AD includes is raw influent alkalinity.

29. The method of claim 24, wherein at least one of said AD reactor biomass concentration controller, said PA reactor nutritional additive concentration controller, and said AD reactor nutritional additive concentration controller uses at least one of said estimated parameters of said online dynamic model of said AD or said model based inferred variables of said AD.

30. The method of claim 29, wherein said estimated parameters of said online dynamic model of said AD or said model based inferred variables of said AD is at least one of reaction coefficients and biomass concentrations for hydrolysis, acedogenthese, acetogenesis, acetoclastic methanogenesis, or hydrogen methanogenesis processes.

31. The method of claim 20, wherein said AD reactor pH supervisory controller is comprised of an AD reactor nonlinear PI pH controller and a PA reactor P alkalinity controller in a cascaded configuration.

32. The method of claim 7, wherein said insoluble organics is comprised of carbohydrates, protein and fat; wherein said soluble substrate and VFA includes sugars, long chain fatty acids (LCFA), amino acids, acetate acid, or propionate acid; wherein said biomass includes biomass for acedogenesis, acetogenesis, acetoclastic methanogenesis, and hydrogen methanogenesis bio-chemical processes.

33. The method of claim 7, wherein said inorganic carbon is comprised of $CO_2$, carbonate, or bicarbonate.

34. The method of claim 1, wherein said bio-chemical reaction kinetics in said online and offline dynamic models of said AD are comprised of insoluble organics hydrolysis, acedogenesis, acetogenesis, acetoclastic methanogenesis, and a hydrogen methanogenesis process.

35. The method of claim 1, wherein said AD is further comprised of a PA reactor, wherein said historical operation data of said AD and said real time operation data of said AD are comprised of raw influent pH, raw influent temperature, raw influent flow rate, raw influent TOC, raw influent TIC, added alkali flow rate, PA reactor fluid level, AD feed flow rate, raw influent SCOD, raw influent TCOD, raw influent SBOD, raw influent VSS, raw influent TSS, raw influent soluble inorganic nitrogen, raw influent VFA, added alkali concentration, PA reactor pH, PA effluent TOC, PA effluent TIC, AD biogas flow rate, AD biogas $CH_4$ concentration, AD Biogas $CO_2$ concentration, AD reactor pH, AD effluent TOC, AD effluent TIC, AD effluent VFA, AD effluent alkalinity, AD reactor MLVSS, AD effluent TCOD, AD effluent SCOD, AD effluent VSS, or AD effluent TSS.

36. The method of claim 1, wherein said AD is further comprised of a PA reactor, wherein said estimated parameters and said adapted model parameters of said offline dynamic model of said AD and said online dynamic model of said AD are comprised of PA reactor composite fraction of carbohydrate, PA reactor composite fraction of fat, PA reactor composite fraction of protein, PA reactor fraction of insoluble convertible to SBOD, PA reactor acedogenthese reaction coefficient, PA reactor biomass decay rate, PA reactor insoluble hydrolysis reaction coefficient, PA reactor insoluble flow out coefficient, PA reactor $CO_2$ escape coefficient, AD reactor composite fraction of carbohydrate, AD reactor composite fraction of fat, AD reactor composite fraction of protein, AD reactor fraction of insoluble convertible to SBOD, AD reactor acedogenthese reaction coefficient, AD reactor acetogenesis reaction coefficient, AD reactor acetoclastic methanogenesis reaction coefficient, AD reactor hydrogen methanogenesis reaction coefficient, AD reactor biomass decay rate, PA reactor insoluble hydrolysis reaction coefficient, and PA reactor insoluble flow out coefficient.

37. The method of claim 1, wherein said AD is further comprised of a PA reactor, wherein said model based inferred variables of said online dynamic model of said AD are comprised of the following unmeasured inputs or outputs of said AD: raw influent insoluble COD, raw influent insoluble inert COD, raw influent soluble inert COD, raw influent SBOD saccharide, raw influent SBOD LCFA, raw influent SBOD amino acid, raw influent propionate acid, raw influent acetate acid, raw influent inorganic carbon content, raw influent alkalinity, raw influent inorganic nitrogen, raw influent SCOD, raw influent TCOD, raw influent SBOD, PA reactor alkalinity, PA reactor VFA, PA reactor temperature, PA reactor SCOD, PA reactor TCOD, PA reactor SBOD, AD reactor alkalinity, AD reactor VFA, AD reactor temperature, AD reactor SCOD, AD reactor SBOD, AD reactor acedogenthese biomass, AD reactor acetogenesis biomass, AD reactor acetoclastic methanogenesis biomass, AD reactor hydrogen methanogenesis biomass, AD reactor insoluble COD, AD reactor insoluble inert COD, AD reactor soluble inert COD, AD reactor SBOD saccharide, AD reactor SBOD LCFA, AD reactor SBOD amino acid, AD reactor propionate acid, AD reactor acetate acid, AD reactor inorganic carbon content, AD reactor alkalinity, AD reactor inorganic nitrogen, AD reactor SCOD, AD reactor TCOD, AD reactor SBOD, SCOD conversion rate, $CH_4$ conversion efficiency, and recycle flow rate.

38. The method of claim 1, further comprising adjusting said adapted model parameters of said online dynamic model of said AD by:
calculating model predicted outputs of said AD using said AD online EKF, said online dynamic model of said AD, said real time measured input data of said AD, and said real time measured output data of said AD, comparing said measured output data of said AD and said model predicted outputs of said AD, and updating said adapted model parameters of said online dynamic model of said AD such that said real time measured output data of said AD substantially correspond with said model predicted outputs of said AD; and
periodically re-identifying said estimated parameters of said offline dynamic model of said AD using said AD offline EKF and said historical operation data for said AD, and importing said estimated parameters from said offline dynamic model of said AD into said online dynamic model of said AD.

39. The method of claim 1, further comprising controlling said AD, wherein said controlling comprises:
providing an AD control system;
wherein said AD is comprised of an AD reactor and a PA reactor; wherein said AD control system uses said real time measured input data of said AD, said real time measured output data of said AD, said estimated parameters of said online dynamic model of said AD, and said model based inferred variables of said AD to control at least one of a nutritional additive concentration of said AD reactor, a nutritional additive concentration of said PA reactor, AD reactor pH, PA reactor pH, biomass concentration of said AD reactor, fluid level of said PA reactor, and a recycle flow rate of said AD.

40. The method of claim 1, wherein said AD supervisory control system is comprised of an AD reactor pH supervisory controller, a PA reactor pH supervisory controller, and an PA:AD overall recycle flow ratio supervisory controller.

41. The method of claim 1, wherein said AD low-level control system is comprised of an AD reactor biomass concentration controller, a PA reactor fluid level controller, a PA reactor nutritional additive concentration controller, and an AD reactor nutritional additive concentration controller.

42. The method of claim 40, wherein said AD reactor pH supervisory controller and said PA reactor pH supervisory controller uses one or more of said model based inferred variables of said AD.

43. The method of claim 40, wherein said AD reactor pH supervisory controller and said PA reactor pH supervisory controller has a feedforward control action; wherein said feedforward control action uses one or more of said model based inferred variables of said AD.

44. The method of claim 20, wherein said AD reactor pH supervisory controller and said PA reactor pH supervisory controller uses one or more of said model based inferred variables of said AD.

45. The method of claim 20, wherein said AD reactor pH supervisory controller and said PA reactor pH supervisory controller has a feedforward control action; wherein said feedforward control action uses one or more of said model based inferred variables of said AD.

* * * * *